(12) United States Patent
Li et al.

(10) Patent No.: US 9,918,480 B2
(45) Date of Patent: Mar. 20, 2018

(54) COMPOSITIONS AND METHODS TO SELECTIVELY CONTROL INVASIVE SPECIES

(71) Applicant: STEPHEN F. AUSTIN STATE UNIVERSITY, Nacogdoches, TX (US)

(72) Inventors: Shiyou Li, Nacogdoches, TX (US);
Ping Wang, Nacogdoches, TX (US);
Wei Yuan, Nacogdoches, TX (US);
Zushang Su, Nacogdoches, TX (US);
Steven H. Bullard, Nacogdoches, TX (US)

(73) Assignee: Stephen F. Austin State University, Nacogdoches, TX (US)

( * ) Notice: Subject to any disclaimer, the term of this patent is extended or adjusted under 35 U.S.C. 154(b) by 0 days.

(21) Appl. No.: 14/889,184

(22) PCT Filed: May 5, 2014

(86) PCT No.: PCT/US2014/036837
§ 371 (c)(1),
(2) Date: Nov. 5, 2015

(87) PCT Pub. No.: WO2014/182627
PCT Pub. Date: Nov. 13, 2014

(65) Prior Publication Data
US 2016/0081353 A1    Mar. 24, 2016

Related U.S. Application Data

(60) Provisional application No. 61/819,713, filed on May 6, 2013.

(51) Int. Cl.
| | | |
|---|---|---|
| A01N 43/90 | (2006.01) | |
| A01N 63/02 | (2006.01) | |
| A01N 65/00 | (2009.01) | |
| A01N 65/04 | (2009.01) | |
| A01N 37/02 | (2006.01) | |
| A01N 65/40 | (2009.01) | |
| A01N 65/18 | (2009.01) | |
| A01N 65/08 | (2009.01) | |

(52) U.S. Cl.
CPC .............. *A01N 65/04* (2013.01); *A01N 37/02* (2013.01); *A01N 43/90* (2013.01); *A01N 63/02* (2013.01); *A01N 65/00* (2013.01); *A01N 65/08* (2013.01); *A01N 65/18* (2013.01); *A01N 65/40* (2013.01)

(58) Field of Classification Search
None
See application file for complete search history.

(56) References Cited

U.S. PATENT DOCUMENTS

| | | | | |
|---|---|---|---|---|
| 8,173,578 | B1 * | 5/2012 | Walker | A01N 63/04 504/117 |
| 2010/0317518 | A1 | 12/2010 | Stevens | 424/406 |
| 2013/0079227 | A1 | 3/2013 | Heilman | 504/150 |
| 2016/0002279 | A1 * | 1/2016 | Li | A61K 31/122 514/25 |

FOREIGN PATENT DOCUMENTS

| | | |
|---|---|---|
| CN | 103004892 A | 4/2013 |
| CN | 103039535 A | 4/2013 |
| WO | WO/14/133811 | 9/2014 |

OTHER PUBLICATIONS

Barrett, "Waterweed Invasions", Scientific American 260: 90-92 (1989).*
Amaranthus palmeri, FNA. 4:412-418, http://www.efloras.org/florataxon.aspx?flora_id=1&taxon_id=242415653, accesed Jan. 6, 2016.
Ascunce, et al., "Global invasion history of the fire ant solenopsis invicta" Science. 331:1066-8, 2011.
Atrichum angustatum, FNA. 27:148-153, http://www.efloras.org/floratacon.aspx?flora_id=1&taxon_id=200002603, accessed Jan. 6, 2016.
Barrett, "Waterweed Invasions." Scientific American. 90-7, 1989.
Bennett, et al., "Glyphosate-resistant johnsongrass in mid-south" Delta Farm Press. http://deltafarmpress.com/glyphosate-resistant-johnsongrass-mid-south accessed Jan. 6, 2016.
Burks, et al., "Nymphoides cristata—snowflakes in sunny Florida." Aquatics. 24(2):8-10, accessed Jan. 6, 2016.
Capinera, Differentiation of Nymphal instars in Schistocerca americana (orthoptera: acrididae). Florida Entomolgist. 76(1):175-9, 1998.
D'Abrosca, et al., "structure elucidation and phytotoxicity of C13 nor-isoprenoids from Cestrum parqui" Phytochemistry. 65:497-505, 2004.
DellaGreca, et al, "Isolation and phytotoxicity of apocarotenoids from Chenopodium album" J Nat Prod. 67:1492-5, 2004.

(Continued)

*Primary Examiner* — Robert A Wax
*Assistant Examiner* — Thor Nielsen
(74) *Attorney, Agent, or Firm* — Norton Rose Fulbright US LLP

(57) ABSTRACT

Methods and compositions for controlling the growth of an invasive species by application of a composition comprised of a natural pesticide derived from a species to the invasive species, especially endocides. Disclosed herein are methods and compositions for controlling the growth of a first invasive species by application of a composition comprising a natural pesticide derived from a second invasive species to the first invasive species. In some embodiments, the invasive species is an invasive species with glands as the primary accumulation sites of autotoxic chemicals. The first and second invasive species may be the same or they may be different. In some embodiments, the natural pesticide may be an endocide. An endocide (endogenous biocide) is a biocide derived from an endogenous bioactive agent (e.g., a secondary metabolite) that does not cause apparent poison in normal growth of the producing species but will poison or inhibit and even eliminate the parent species when induced in producing species.

20 Claims, 35 Drawing Sheets

(56) References Cited

OTHER PUBLICATIONS

Ding, et al., "Assessing potential biological control of the invasive plant, tree-of-heaven, Ailanthus altissima" Biocontrol Sci and Technol. 16:547-588, 2006.
Everest, "Kudzu in Alabama: History, Uses and Control" Alabama Cooperative Extension Syste, ANR-65, 1999.
Greenlee & Harrison, "Development of respiratory function in the American locust" J Exp Biol. 207:497-508, 2004.
Hanula, et al., "Chinese privet (*Ligustrum sinense*) removal and its effect on native plant communication of riparian forests" Invasive plant science and managmenet. 2:292-300, 2009.
Harrington & Miller, "Effects of applicatio nrate, timing, and formulation of glyphosate and triclopyr on control of Chines privet" Weed Technol. 19:47-54, 2005.
International Preliminary Report on Patentability in International Application No. PCT/US2014/036837 dated Nov. 19, 2015.
International Search Report and Written Opinion in International Application No. PCT/US2014/036837 dated Sep. 23, 2014.
Kunz, et al., "Warm-season forages for free-ranging white-tailed beer in south Texas." The Texas J of Agricult and Nat Res. 22:7-16, 2009.
Leonard, "Monsanto's Baned: The evil pigweed." http://www.salon.com/2008/08/27/monsantos_bane/ 2008.
Li, et al., "Cytotoxic compounds from invasive giant salvinia (*Salvinia molesta*) against human tumor cells." Bioorganic & Medicinal Chemistry Letters. 23:6682-7, 2013.
Lorenzi & Jeffery, "Weeds of the United States and their Control" Published by Van Nostrand Reinhold Company, NY. 1987.
McWhorter, et al., "History, Biology and Control of Johnsongrass" Rev Weed Sci. 4:85-171, 1989.
Mitchell, "Surface-floating aquatic macrophytes" pp. 109-124, 1985.
Mitchell, et al., "Managing yaupon with fire and herbicides in the texas post oak savannah." University of Nebraska—Lincoln. USDA-ARS/UNL Faculty. 2005.
Perez & Trujillo, "Absolute structures of two new C13-norisoprenoids from Apollonias barbujana" J Nat Prod. 59:69-72, 1996.
Popovici, et al., "An allelochemical from Myrica gale with strong phytotoxic activity against highly invasive fallopia x bohemica taxa." Molecules. 16:2323-33, 2011.
Powles, "Evolved glyphosate-resistant weeds around the world: lessons to be learnt" Ped Manag Sci. 64:360-65, 2008.
Shao, et al., "Phytotoxic effects and a phytotoxin from the invasive plant xanthium italicum moretti" Molecules. 17:4037-46, 2012.
Squitier, "American grasshopper, Schistocerca americana." The University of Florida. EENY-004, Published: 1996, revised: 2005.
Tveten, Wildflowers of Houston and Southeast Texas. UT Press, Austin. 1993.
Vila-Aiub, et al., "Evolution of glyphosate-resistant Johnsongrass in glyphosate-resistant soybean" Weed Sci. 55(6):566-71, 2007.
Wenger, "The sprouting of sweetgum in relation to season of cutting and carbohydrate content" Plant Physiology. 35-49, 1951.
Willey & Langeland, Aquatic weeds: crested floating heart. The University of Florida. SS-AGR-344, published: 2011, reviewed: 2014.
Anonymous, "SFA Researchers discover cancer-treating potential of invasive plant," News-SFASU, Jul. 11, 2011.
Chantiratikul, et al., "Antioxidant activitives and phenolic contents of extracts from *Salvinia molesta* and *Eichornia crassipes*" Res J Biol Sci. 4(1):1113-1117, 2009.
Chen, et al., "Defensive Chemistry of tawny crazy ants" Toxicon. 76:160-166, 2013.
Choudhary, et al., "Phenolic and other constituents of fresh water fern *Salvinia molesta*" Phytochemistry. 69:1018-23, 2008.
First Office action in Chinese application No. 2014800244856 dated Nov. 2, 2016.
Mithraja, et al., "Phytochemical studies on *Azolla pinnata* R. Br., *Marsilea minuta* L. and *Salvinia molesta* Mitch" Asian Pacific J Trop Biomed. S26-S29, 2011.
Search Report and Written Opinion in European Application No. 14794280 dated Sep. 20, 2016.
Search report in Chinese application No. 2014800244856 dated Oct. 25, 2016.
Singh, et al., Autotoxicity: Concept, Organisms, and Ecological Significance: Crit Rev Plant Sci. 18(6):757-72, 1999.

* cited by examiner $R_1=OH, R_2=\beta-H$ or
$R_1=\alpha-H, R_2=OH$

| Position | β-anomer | | α-anomer | |
|---|---|---|---|---|
| | $\delta_C$ | $\delta_H$ | $\delta_C$ | $\delta_H$ |
| 2 | 158.3 | | 158.4 | |
| 3 | 110.3 | | 110.2 | |
| 4 | 129.7 | | 129.7 | |
| 5 | 114.9 | | 114.8 | |
| 6 | 130.0 | 7.70 (1H,d, J=8.2 Hz) | 130.0 | 7.70 (1H,d, J=8.2 Hz) |
| 7 | 112.1 | 6.82 (1H,d, J=8.2Hz) | 112.1 | 6.82 (1H,d, J=8.2 Hz) |
| 8 | 148.8 | | 148.8 | |
| 9 | 143.5 | | 143.5 | |
| 10 | 168.7 | | 168.7 | |
| 11 | 168.1 | | 168.1 | |
| 1' | 121.6 | | 121.6 | |
| 2' | 121.5 | 7.39 (1H,dd, J=8.5 and 1.8 Hz) | 121.4 | 7.39 (1H,dd, J=8.5 and 1.8 Hz) |
| 3' | 116.8 | 6.84 (1H,d, J=8.5Hz) | 116.8 | 6.84 (1H,d, J=8.5Hz) |
| 4' | 149.4 | | 149.4 | |
| 5' | 146.8 | | 146.8 | |
| 6' | 115.7 | 7.45 (1H,d, J=1.8Hz) | 115.7 | 7.45 (1H,d, J=1.8Hz) |
| Glc-1" | 98.6 | 4.57 (1H, d, J=7.8 Hz) | 94.4 | 5.14 (1H, d, J=3.7 Hz) |
| Glc-2" | 76.7 | 3.27 (1H, dd, J=7.8 and 9.2 Hz) | 74.2 | 3.51(1H, dd, J=3.7 and 9.2 Hz) |
| Glc-3" | 74.5 | 3.57 (1H. dd, J=9.6 and 9.2 Hz) | 71.6 | 3.83 (1H, t, J=10.1 Hz) |
| Glc-4" | 77.8 | 5.30(1H, t, J=9.6 Hz) | 78.4 | 5.24 (1H, t, J=9.6 Hz) |
| Glc-5" | 68.9 | 3.78 (1H, td, J=10.5 and 4.1 Hz) | 64.4 | 4.24 (1H, td, J=10.5 and 4.1 Hz) |
| Glc-6" | 65.8 | 3.94 (1H, t, J=11.0 Hz)<br>5.04 (1H, dd, J=10.3 and 4.1 Hz) | 66.4 | 3.91 (1H, t, J=11.0 Hz)<br>4.97(1H, dd, J=10.3 and 4.1 Hz) |

[a] The assignment was based upon COSY, HSQC, and HMBC experiments.

FIG. 10

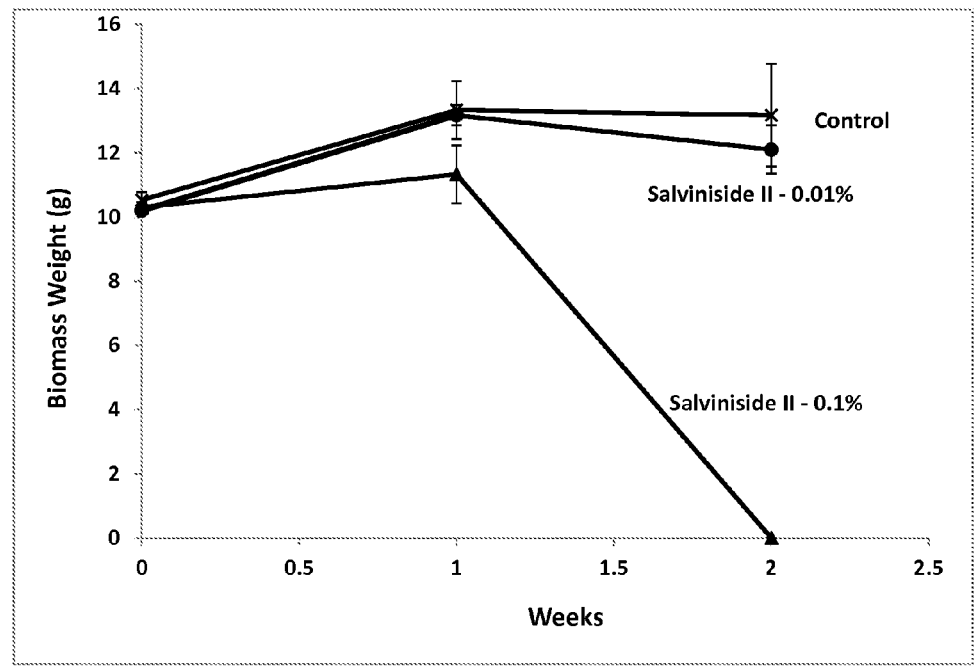

FIG. 11

| Sample | Concentration (ppm) | | | | | | |
|---|---|---|---|---|---|---|---|
| | Al 167.079 {502} (Axial) | Ag 328.068 {103} (Axial) | As 189.042 {478} (Axial) | Ba 455.403 {74} (Axial) | Ca 315.887 {107} (Radial) | Cd 228.802 {447} (Axial) | Co 238.892 {141} (Axial) |
| Detection Limit | 0.000131 | 0 | 0.018095 | 0.019556 | 0.08355 | 0.001159 | 0.008098 |
| Dried plant matter of giant salvinia | 2590.174 | N.D. | 0.406585 | 167.3372 | 2484.59 | N.D. | N.D. |
| Powder of water extract from the dried matter of giant salvinia | 27.24901 | 208.6338 | 5.929026 | 1023.409 | 21087.45 | 0.16047 | N.D. |
| Precipitated salts from water extract | 1.638688 | 297.7474 | N.D. | 68.61493 | 10785.6 | 0.032935 | 0.517186 |

Note: N.D.: not detected.

| Sample | Concentration (ppm) | | | | | | |
|---|---|---|---|---|---|---|---|
| | Cr 283.563 {119} (Axial) | Cu 324.754 {104} (Axial) | Fe 259.940 {130} (Axial) | Hg 194.227 {473} (Axial) | K 766.490 {44} (Radial) | Mg 279.553 {120} (Radial) | Mn 257.610 {131} (Axial) |
| Detection Limit | 0.002003 | 0.00129 | 0.001489 | 0.003028 | 0.50856 | 0.001998 | 0.000219 |
| Dried plant matter of giant salvinia | 1.447096 | 2.089414 | 10.54264 | N.D. | 7124.003 | 3570.896 | 803.5884 |
| Powder of water extract from the dried matter of giant salvinia | 0.883666 | 5.310525 | 228.0387 | N.D. | 159989 | 15735.46 | 980.4232 |
| Precipitated salts from water extract | 0.108073 | 0.365211 | N.D. | N.D. | 26450.6 | 4825.299 | 5.5261 |

Note: N.D.: not detected.

| Sample | Concentration (ppm) | | | |
|---|---|---|---|---|
| | Mo 202.030 {467} (Axial) | Na 589.592 {57} (Radial) | Pb 220.353 {453} (Axial) | Zn 213.856 {457} (Axial) |
| Detection Limit | 0.00648 | 0.244719 | 0.012542 | 0.000277 |
| Dried plant matter of giant salvinia | N.D. | 5648.046 | -0.32127 | N.D. |
| Powder of water extract from the dried matter of giant salvinia | 0.039819 | 89817.5 | 2.515505 | 166.7952 |
| Precipitated salts from water extract | N.D. | 291131.9 | 7.828878 | 0.86571 |

Note: N.D.: not detected.

FIG. 25

COMPOSITIONS AND METHODS TO SELECTIVELY CONTROL INVASIVE SPECIES

CROSS-REFERENCE TO RELATED APPLICATIONS

This application is a national phase application under 35 U.S.C. § 371 of International Application No. PCT/US2014/036837, which claims the benefit of priority of U.S. Provisional Application No. 61/819,713, filed May 6, 2013. The entire contents of each of the above-referenced disclosures are hereby incorporated by reference.

BACKGROUND OF THE INVENTION

A. Field of the Invention

The present invention relates generally to the fields of Biology and Chemistry. More particularly, it concerns compositions and methods for controlling the growth of invasive species by endocides.

B. Description of Related Art

Invasive species are major threats to agriculture, natural environments, and public health (Ascunce et al. 2011). The estimated annual damage from invasive species worldwide totals more than $1.4 trillion—five percent of the global economy (The Nature Conservancy, 2013). The principle of the current management strategies of invasive species in the world is mainly restricted to eliminate or eradicate the species by using synthetic herbicide, biological or mechanical applications. Such control measures of invasive species are difficult and often very expensive (Beck et al. 2008). Controlling invasive species and the associated economic and environmental damages amounts to more than $138 billion per year (Pimentel et al. 1999). More than $500 million is spent on residential exotic weed control and an additional $1 billion is invested in non-indigenous weed control on golf courses (Pimentel et al. 1999). In addition to huge expenditures, effectiveness decreases as more species develop resistance to herbicides and public environmental concerns regarding chemical and biological applications increase, it requires a novel philosophy to successfully control the noxious invasive species.

Five of the most aggressive and noxious species in the southeastern United States are representative of different groups of invasive species. They include one fern species: giant *salvinia* (*Salvinia molesta* D. S. Mitchell) (family Salviniaceae) from the phyllum Pteridophyta of the kingdom Plantae, two flowering plant species: Brazilian pepper tree (*Schinus terebinthifolius* Raddi) (family Anacardiaceae) from the order Sapindales and Chinese tallow tree (*Triadica sebifera* (L.) Small) (family Eurphorbiaceae) from the order Malpighiales of the phyllum Flowering Plants of the kingdom Plantae, and two insect species: the red imported fire ant (*Solenopsis invicta* Buren) (family Formicidae) from the superorder Endopterygota and the subterranean termite (*Reticulitermes flavipes* (Kollar)) (family Rhinotermitidae) of superorder Exopterygota of the phylum Arthropoda of the kingdom Animalia. Of these species, giant *salvinia* is an aquatic species and the others are terrestrial species.

*Salvinia* Séguier is a genus of floating ferns belonging to the family Salviniaceae Reichenbach and has 10-14 species in the world, particularly in the tropics. *Salvinia molesta* D. S. Mitchell, known as giant *salvinia*, water fern, or kariba weed, is native to Brazil. Since 1939, it has invaded lake and river systems in warm climates in the world (Room et al. 1990). At present, giant *salvinia* is one of the most widespread and environmentally, economically and socially destructive invasive plant species (Schooler et al. 2011). In addition, giant *salvinia* provides habitat for snails that are intermediate hosts for *Schistosoma* sp. which parasitize the human intestinal and urinary tracts. The parasitic disease schistosomiasis is also known as snail fever, *bilharzia*, or bilharziosis, is the second most socioeconomically devastating parasitic disease after malaria.

Giant *salvinia* is able to double in number and biomass in less than three days under optimal condition and forms dense mats over still waters (Barrett 1989). The plant can regenerate vegetatively even after severe damage or drying for days (Finlayson 1984; Room and Thomas 1986). The explosive growth of *S. molesta* adversely affects the natural ecological system of the infested region, and it also causes considerable economic damage and sanitation problems. Dense mats of *S. molesta* reduce dissolved oxygen levels and block all sunlight from penetrating the infested water body. Thus, macrophytes and microscopic algae that form the base of the food chain may die off (Room et al. 1990). The creatures that feed on these may die, too, and so on up the food chain. This pest threatens cultivated aquatic crops, and it can clog irrigation and drinking water lines and foul hydroelectric plants. *Salvinia*-infested waters cannot be used for boating or other recreational purposes (USDA 2000). Biological, mechanical, and herbicidal control of invasive giant *salvinia* is very expensive and has not been successful. Since 1980, the tiny *salvinia* weevil (*Cyrtobagous salviniae*, Curculionidae) has been introduced into most regions where giant *salvinia* has invaded (Julien et al. 2009). The weevil is a strict specialist with adults feeding on *salvinia* buds; the plant is highly susceptible to the insects and thus the weevil has successfully controlled *salvinia* for years in some regions. But recently it was found that the biological control is incomplete and fitful associated with stochastic flooding events and thus is unpredictable (Schooler et al. 2011). Other attempts to control and eradicate *S. molesta* through herbicides and mechanical means have failed to achieve their purpose and may cause environmental backlashes due to the introduction of chemicals or bioagents into the environment (Abbasi and Nipaney 1986).

Brazilian pepper tree (*Schinus terebinthifolius* Raddi) (family Anacardiaceae) is an evergreen shrub or tree (up to 12 m in height) native to South America and was introduced to North America in the 1800s as an ornamental plant. Like poison ivy or sumac of the same family, this species may also cause dermatitis to people with sensitive skin and even respiratory problems during its bloom period. Brazilian pepper tree has extensively infested landscapes in Florida and south Texas and it produces a dense canopy that shades out other plants particularly native species. It is reported that its aqueous extract inhibited the growth and germination of native Florida plants (Morgan and Overhlt 2005). The invasiveness of Brazilian pepper tree can be attributed to its high seed production, high germination rates and dispersal by birds and mammals. Currently, small pepper tree seedlings are controlled by digging or pulling and also by the application of herbicides.

Chinese tallow tree (*Triadica sebifera* (L.) Small) (family Eurphorbiaceae) is native to China and is now a very invasive species in the southeastern United States. A mature tree may annually produce an average of 100,000 seeds that are spread mainly by birds and water (Jubinsky and Anderson 1996). Under the parent tree, there maybe approximately 15 seedlings per square meter, and its relative frequency of tallow seedlings was greater than that of all species except for sweetgum (*Liquidambar styraciflua* L.). Various measures, including manual and mechanical, environmental/cultural, chemical, and biological methods have been used to control this invasive species.

Since its introduction from its native South American range in the 1930s, the red imported fire ant (*Solenopsis invicta* Buren) (family Formicidae) has rapidly widespread throughout the southern United States. It has also recently invaded other regions of the world, including the Caribbean, Mexico, Australia, New Zealand, Malaysia, Singapore, and China (Chen et al. 2009; Ascunce et al. 2011). Unlike other insects in Hymenoptera, the red imported fire ant contains a small fraction of proteins in its venom. About 95% of the fire ant venom consists of alkaloids (primarily 2-methyl-6-alkyl or alkenyl piperidines), which are responsible for the immediate hive formation and the development of the sterile pustule at the sting site (Chen et al. 2009; Hoffman 2010). The pest detrimentally impacts human health, livestock, wildlife, crops, machinery, and electrical equipment (Morrison et al. 2004). The estimated cost of control, medical treatment, and damage to property by fire ant in the United States alone is more than $6 billion annually (Ascunce et al. 2011). An effective measure for control is needed for both ecological and economic reasons.

Eastern subterranean termite (*Reticulitermes flavipes* (Kollar)) (family Rhinotermitidae) is the most common termite found in North America. This native termite is one of the most economically important wood destroying pests in the United States and it causes billions of dollars in home damage each year. Currently, termite management includes reducing the potential for termite infestation, preventing entry, and chemical control.

The use of defensive chemicals is commonly reported throughout the plant and animal kingdoms. It is known that exceptional success of some invasive species is because they produce toxic secondary metabolites and have negative allelopathic effects on neighboring plants or to protect themselves from microbial attacks and insect/animal herbivory (Quintana et al. 2008; Paudel 2009). Studies on defensive or allelopathic effects of chemicals are mainly to inter-species. Autotoxicity (autointoxication or intraspecific allelopathy in plants) has not been well investigated although it has been hypothesized to exist since the 1970s (McKey 1974; Fowden and Lea 1979; Li et al. 2010). The term was used in plants when a species releases toxic substances into the environmenmt that inhibit or delay germination and growth of the same species (Chou and Lin 1976; Singh et al. 1999). There are few autotoxicity reports in crops and weeds and resulting soil sickness and replanting problems (Singh et al. 1999). These reported autotoxic chemicals had broad-spectrum allelopathic effects and were more effectively inhibited in non-closely-related species in other genera, families or orders than in the parent species (Abdul-Rahman and Habib 1989; Heisey 1999; Batish et al. 2002). However, many of these reports are general allelopathy rather than autotoxicity cases. For example, the effective concentrations of momilactone A and B from rice (*Oryza sativa* L.) (family Poaceae) to inhibit the seedlings of rice cultivars were 100 and 333 times, respectively of those to inhibit four species of Brassicaceae, Asteraceae, and Fabaceae and five weed grass species of Poaceae (Kato-Noguchi and Ota 2013). Leaf extracts from *Leucaena leucocephala* de Wit. (family Fabaceae) had significant toxic effects on crop or tree species belonging to other genera of Fabaceae or other families but were not toxic to *L. leucocephala* seedlings (Chou and Kuo 1986). Minosine isolated from *L. leucocephala* had more potent inhibitory activity on the seedlings of five species of Brassicaceae, Asteraceae, Fabacreae, and Poaceae but did not show any inhibition on the producing plants at 100 mg/L (Xuan et al. 2006). Leaf and flower extracts of ragweed (*Parthenium hysterophorus* L.) (family Asteraceae) inhibited the germination and growth of several species in Brassicaceae, Fabaceae, and Poaceae although they showed autotoxic effects to the producing plants (Picman and Picman 1984; Javaid et al. 2007). Alfalfa (*Medicago sativa* L.) (family Fabaceae) is one of the most extensive investigated and well-known autotoxicity species. It was reported that alfalfa extracts and its phenolics or saponins showed autotoxic effects on seedling growth of alfalfa and allelopathic effects on several crop and weed species of Fabaceae, Poaceae, and Brassicaceae (Wyman-Simpson et al. 1991; Chon et al. 2002). However, alfalfa allelopathy seems to be more severe than autotoxicity (Hedge and Miller 1990). Such non-selectivity or low toxicity of the reported autotoxic chemicals to the parent species over other species limited the development of biocide to selectively control an invasive species. In fact, it has been widely believed that a species can avoid self-toxicity by its endogenous cytotoxic metabolites (Baldwin and Callahan 1993; Wang 1996; Gog et al. 2005; Sirikantaramas et al. 2008a, b). Therefore, studies in autotoxicity have been primarily focused on avoidance of autotoxicity and detoxification mechanisms. To date there is no method or product developed to use any autotoxic chemicals to selectively control the invasive parent species.

SUMMARY OF THE INVENTION

Disclosed herein are methods and compositions for controlling the growth of a first invasive species by application of a composition comprising a natural pesticide derived from a second invasive species to the first invasive species. In some embodiments, the invasive species is an invasive species with glands as the primary accumulation sites of autotoxic chemicals. The first and second invasive species may be the same or they may be different.

In some embodiments, provided are methods of controlling the growth of an invasive species comprising applying a composition comprising a natural pesticide to the invasive species, wherein the natural pesticide is derived from an invasive species. Any measure of decreased growth or reproduction of the invasive species is contemplated. In some embodiments, the growth of the invasive species may be slowed or halted. In some embodiments, the invasive species may be eliminated. In some embodiments, the growth of the invasive species is halted within 1, 2, 3, 4, 5, 6, 7 days, 1, 2, 3, 4, or 5 weeks, 1, 2, 3, 4, 5, 6, 7, 8, 9, 10, 11, or 12 months or more. In some embodiments, the growth of the invasive species is halted within 1 week or 1 month. In some embodiments, the growth of the invasive species is halted for at least 1, 2, 3, 4, or 5 weeks, 1, 2, 3, 4, 5, 6, 7, 8, 9, 10, 11, or 12 months, 1, 2, 3, 4, 5, 6, 7, 8, 9, 10 years or more. In some embodiments, the growth of the invasive species is halted for at least 1 year.

In some embodiments, the natural pesticide may be an endocide. An endocide (endogenous biocide) is a biocide derived from an endogenous bioactive agent (e.g., a secondary metabolite) that does not cause apparent poison in normal growth of the producing species but will poison or inhibit and even eliminate the parent species when induced in producing species. It can selectively eliminate the parent species (and possibly its closely-related species) when externally applied. The dead tissues of the species caused by an endocide will enhance the endocidal function to the species. The endocide may have effects especially in the species with glands as accumulation sites of autotoxic chemicals. An endocide may have effects in all or some growth stages of the species (e.g., primary, secondary, and tertiary stages) and in all or selective tissues (vegetative or reproductive tissues).

Application of endocides at low concentrations (dosages) may be used in control a selected part (e.g., a specific cell(s), tissue(s), or organ(s)) of the producing species. Application of endocides at low concentrations (dosages) may produce abnormal morphogenesis. In some embodiments, the endocides may induce mutations. In some embodiments, the induced mutations may be used to produce desirable genotypes. In some embodiments, the induced biosynthesis of endogenous autotoxic chemicals by a method intended to stimulate gland development may also produce abnormal morphogenesis, mutations, and desirable genotypes.

In some embodiments, the endocide is an extract from the invasive species to be controlled. In some embodiments, the endocide is a fraction of extract from the invasive species to be controlled. In some embodiments, the endocide is dry matter from the invasive species to be controlled. In some embodiments, the endocide is fresh matter from the invasive species to be controlled. The natural pesticide "derived from a species" may be any composition or compound originally obtained from a species, even if further modified. It also encompasses synthetic compounds that are equivalent to the compounds derived from the species or derivatives thereof.

In some embodiments, the natural pesticide is derived from a second, distinct species of invasive species. In some embodiments, the natural pesticide is a compound isolated from the second invasive species.

The natural pesticides may be any appropriate material. In some embodiments, the natural pesticide is the dry or fresh matter. In some embodiments, the natural pesticide is an extract or fraction thereof. In some embodiments, the extract is an aqueous or organic extract or fraction thereof. In some embodiments, the extract is a dry or solubilized extract. In some embodiments, the natural pesticide is dry matter. In some embodiments, the intact dry matter is used for production of the natural pesticides. In some embodiments, the dry matter is ground or processed. In some embodiments, the natural pesticide is a concentrated extract or fraction from dry matter. In some embodiments, the natural pesticide is fresh matter. In some embodiments, the intact fresh matter is used for production of the natural pesticides. In some embodiments, the fresh matter is chopped or blended. In some embodiments, the natural pesticide is an extract (juice) obtained directly from chopped, blended, or/and expressed fresh matter. In some embodiments, the natural pesticide is a concentrated extract juice from chopped, blended, or/and expressed fresh matter. In some embodiments, the natural pesticide is a diluted extract juice from chopped, blended, or/and expressed fresh matter. In some embodiments, the natural pesticide is a compound isolated from the species of invasive species to be controlled. In some embodiments, the natural pesticide is a compound isolated from a second species of invasive species.

In some embodiments, the natural pesticide is ground dried matter in a water-penetrating bag. In some embodiments, the bag material is fabric, nylon, plastic, compostable, or biodegradable. In some embodiments, the natural pesticide is ground dried species matter in compressed form (e.g., compressed brick or pie ("tea brick")) without a bag. The tea brick can be prepared under appropriate moisture (7-15%), temperature (50-90° C.), and pressure (250-500 kPa). It may float around or on the surface of the invasive species to be controlled and may break down and dissolve in the water within a few minutes after contact with water is made. It may mix with local soils to prepare a sinkable tea brick which can contact water quickly and be more effective.

In some embodiments, production of extract from the dried species matter may include processes of fresh matter collection of harvest, drying, grounding, extraction, filtration, concentrating, formula preparation, and spray application. In some embodiments, extraction is aqueous or organic solvent extraction, distillation, infusion, decoction, or percolation.

In some embodiments, production of extract (juice) from fresh species matter may include processes of fresh matter collection or harvest, shredding or pulping, extraction, filtration, formula preparation, and spray application. In some embodiments, extraction an expression method (e.g., hydraulic pressing, screw pressing, expeller pressing, sponge expression, abrasion, and Écuelle à piquer).

The natural pesticide may have selective activity against the invasive species to be controlled over other species. The selectivity is more significant when the natural pesticide is an extract. In some embodiments, the natural pesticide may have selective activity against the invasive species to be controlled and its closely-related species over other species. In some embodiments, the closely-related species is a species within the same genus. In some embodiments, the closely-related species is a species within the same family. In some embodiments, the closely-related species is a species within the same order. In some embodiments, a composition comprising the natural pesticide can eliminate or inhibit the invasive species. In some embodiments, a composition comprising the natural pesticide can eliminate or inhibit the invasive species and its closely-related species (e.g., a species of the same order) of the invasive species. In some embodiments, a composition comprising the natural pesticide does not inhibit or slightly inhibit a native species that is not in the genus, family, or order of the invasive species. In some embodiments, a composition comprising the natural pesticide does not inhibit or slightly inhibit an invasive species that is not in the genus, family, or order of the invasive species.

In some embodiments, the natural pesticide is a compound of formula:

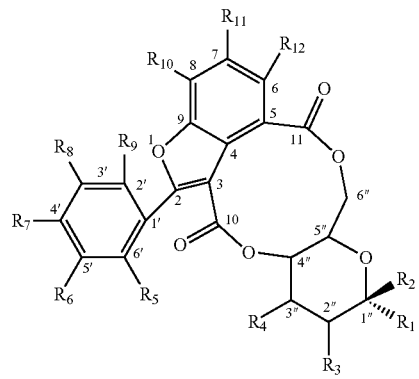

wherein each $R_1$, $R_2$, $R_3$, $R_4$ is independently —H, —OH, -halogen, —$NH_2$, —COOH, —C(O)$NH_2$, —SH, —S(O)$NH_2$, —S(O)$_2NH_2$, —OCH$_2$OR$_{13}$, —OC(O)R$_{13}$, —OC(O)OR$_{13}$, —OC(O)NR$_{13}$, —OP(O)(OR$_{13}$)$_2$, —SR$_{13}$, —S(O)$_2$NHR$_{13}$, —OP(O)(OR$_{13}$)$_2$, —SOR$_{13}$, —S(O)$_2$R$_{13}$, —NHC(O)R$_{13}$, —NHSOR$_{13}$, NHS(O)$_2$R$_{13}$, —OPO(OR$_{14}$)$_2$, —O-arylPO(OR$_{14}$)$_2$, or —O— alkylaryl-PO(OR$_{14}$)$_2$, —NHR$_{13}$, —N(R$_{13}$)$_2$, —C(S) R$_{13}$, —OR$_{13}$, Each R$_5$, R$_6$, R$_7$, R$_8$, R$_9$, R$_{10}$, R$_{11}$, R$_{12}$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$-C$_{10}$ (oxy)alkyl, —C$_1$-C$_{10}$ alky, —C$_1$-C$_{10}$ alkoxy, —C$_1$-C$_{10}$ (hydroxyl)alkyl, —C$_1$-C$_{10}$ (amino)alkyl, —C$_1$-C$_{10}$ (halo)alkyl, —C$_2$-C$_{10}$ alkenyl, —C$_2$-C$_{10}$ (aryl)alkyl, —CH$_2$OR$_{13}$, —OCH$_2$OR$_{13}$, —OC(O)R$_{13}$, —C(O)R$_{13}$, —OC(O)OR$_{13}$, —OC(O)NR$_{13}$, —C(O)OR$_{13}$, —C(O)NR$_{13}$, —OP(O)(OR$_{13}$)$_2$, —SR$_{13}$, —S(O)$_2$NHR$_{13}$, —C(O)NR$_{13}$, —OP(O)(OR$_{13}$)$_2$, —SR$_{13}$, —S(O)$_2$NHR$_{13}$, —SOR$_{13}$, —S(O)$_2$R$_{13}$, —NHC(O)R$_{13}$, —NHSOR$_{13}$, NHS(O)$_2$R$_{13}$, —OPO(OR$_{14}$)$_2$, —O-arylPO(OR$_{14}$)$_2$, or —O— alkylaryl-PO(OR$_{14}$)$_2$, -isocyanate, -azido, and R$_{14}$ is —H, —C$_1$-C$_{10}$ alkyl, C$_7$-C$_{13}$ arylalkyl, C$_1$-C$_{10}$ aminoalkyl, C$_1$-C$_{10}$ haloalkyl, C$_1$-C$_{10}$ hydroxyalkyl, C$_1$-C$_{10}$ alkoxy, -isocyanate, -azido, -imino, -thio, and R$_{13}$ is —H, —C$_1$-C$_{10}$ alkyl, —(C$_3$-C$_7$) cycloalkyl, —C$_1$-C$_{10}$ (halo)alkyl, -aryl, —C$_2$-C$_{10}$ alkenyl, —C$_2$-C$_{10}$, —C$_2$-C$_{10}$ alkynyl, —C$_1$-C$_{10}$ (aryl)alkyl, —C$_2$-C$_{10}$ (aryl)alkenyl, —C$_2$-C$_{10}$ (aryl)alkynyl, —C$_1$-C$_{10}$ (hydroxyl)alkyl, —C$_1$-C$_{10}$ alkoxy, —C$_1$-C$_{10}$ (amino)alkyl, -isocyanate, -azido, -imino, -thio, -alkenyloxy, -alkynyloxy, -aryloxy, -aralkoxy, -heteroaryloxy, -acyloxy, -alkoxyamino, -alkenylamino, -alkynylamino, -arylamino, -aralkylamino, -heteroarylamino, -alkylsulfonylamino, -heterocycloalkyl, -heteroaryl.

In some embodiments, the natural pesticide is a compound of formula:

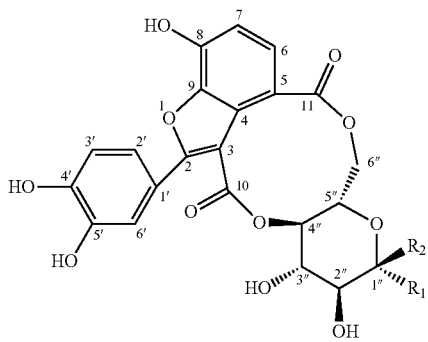

wherein R$_1$ is OH or α-H; and R$_2$ is β-H or OH. In some embodiments, R$_1$=OH, R$_2$=β-H. In some embodiment, R$_1$=α-H, R$_2$=OH. In some embodiments, R$_1$=OH, R$_2$=OH. In some embodiment, R$_1$=α-H, R$_2$=β-H. These compounds may be extracted and isolated from plant material or may be chemically synthesized.

The invasive species may be any appropriate invasive plant. In some embodiments, the invasive plant is an aquatic plant. In some embodiments, the invasive aquatic plant is *Salvinia adnata* Desvaux, *S. auriculata* Aublet, *S. biloba* Raddi, *S. cucullata* Roxb. ex Bory, *S. cyathiformis* Maxon, *S. hastate* Desvaux, *S. herzogii* de la Sota, *S. martynii* Kopp, *S. minima* Baker, *S. molesta*, *S. natans* (L.) Allioni, *S. nymphellula* Desvaux, *S. oblongifolia* Martius, *S. radula* Baker, *S. rotundifolia* Willd., *S. sprucei* Kuhn, *Azolla caroliniana* Willd. (family Azollaceae, sometimes the genus *Azolla* Lam. was placed in the family Salviniace), *A. circinate* Oltz & Hall, *A. cristata* Kaulf., *A. filiculoides* Lam., *A. japonica* Franch. & Say., *A mexicana* C. Presl, *A. microphylla* Kaulf., *A. nilotica* Decne. ex Mett., *A. pinnata* R. Br., *A. rubra* R. Br., *Lemna minuta* Kunth (family Araceae), *Alternanthera philoxeroides* (Matt.) Griseb. (family Amaranthaceae), *Colocasia esculenta* (L.) Schott (family Araceae), *Eichharnia crassipes* (Martius) Solms (family Pontederiaceae), *Hydrilla verticillate* (L. f.) Royle (family Hydrocharitaceae), *Hygrophila polysperma* Anderson (family Acanthaceae), *Hymenachne amplexicaulis* (Rudge) Nees (family Poaceae), *Ipomoea aquatica* Forssk (family Convolvulaceae), *Myriophyllum spicatum* L. (family Haloragaceae), *Panicum repens* L. (family Poaceae), *Pennisetum purpureum* Schumach (family Poaceae), *Pistia stratiotes* L. (family Araceae), or *Urochloa mutica* (Forssk.) T.Q. Nguyen (family Poaceae). In particular embodiments, the invasive plant is *S. molesta*, *S. minima*, *A. caroliniana*, *L. minuta*, *E. crassipes*, or *P. stratiotes*.

The invasive species may be any appropriate invasive plant. In some embodiments, the invasive plant is a terrestrial plant. In some embodiments, the invasive plant is *Acacia mearnsii* De Wild (family Fabaceae), *Acroptilon repens* (L.) DC. (family Asteraceae), *Ailanthus altissima* (P. Mill.) Swingle (family Simaroubaceae), *Akebia quinata* (Houtt.) Decne. (family Lardizabalaceae), *Albizia julibrissin* Durazz. (family Fabaceae), *Alliaria petiolata* (M. Bieb.) Cavara & Grande (family Brassicaceae), *Ampelopsis brevipedunculata* (Maxim.) Trautv. (family Vitaceae), *Ardisia crenata* Sims (family Myrsinaceae), *Arundo donax* L. family Poaceae), *Berberis thunbergii* DC. (family Berberidaceae), *Bromus tectorum* L. (family Poaceae), *Broussonetia papyrifera* (L.) L'Hér. ex Vent. (family Moraceae), *Cardaria pubescens* (C. A. Mey.) Jarmolenko (family Brassicaceae), *Carduus nutans* L. (family Asteraceae), *Celastrus orbiculatus* Thunb. (family Celastraceae), *Centaurea stoebe* L. spp. *micranthos* (Gugler) Hayek (family Asteraceae), *Centaurea stoebe* L. spp. *micranthos* (Gugler) Hayek, *C. solstitialis* L., *C. diffusa* Lam., *C. calcitrapa* L. (family Asteraceae), *Cecropia peltata* L. (family Urticaceae), *Chromolaena odorata* (L.) King & H. E. Robins (family Asteraceae), *Cinchona pubescens* Vahl (family Rubiaceae), *Eichharnia crassipes* (Martius) Solms (family Pontederiaceae), *Cinnamomum camphora* (L.) J. Presl (family Lauraceae), *Cirsium arvense* (L.) Scop. (family Asteraceae), *Clidemia hirta* (L.) D. Don (family Melastomataceae), *Cynoglossum officinale* L. (family Boraginaceae), *Cytisus scoparius* (L.) Link (family Fabaceae), *Dioscorea alata* L., *D. bulbifera* L., or *D. oppositifolia* L. (family Dioscoreaceae), *Dipsacus fullonum* L. (family Dipsacaceae), *Elaeagnus angustifolia* L., *E. pungens* Thunb., or *E. umbellata* Thunb. (family Elaeagnaceae), *Elymus repens* (L.) Gould (family Poaceae), *Eragrostis curvula* (Schrad.) Nees family Poaceae), *Euonymus alatus* (Thunb.) Sieb. or *E. fortunei* (Tursz.) Hand.-Maz. (family Celastraceae), *Euphorbia esula* L. (family Euphorbiaceae), *Firmiana simplex* (L.) W. Wright (family Sterculiaceae), *Frangula alnus* Mill. (family Rhamnaceae), *Hedera colchica* (K. Koch) K. Koch, *H. helix* L. *H. hibernica* (G. Kirchn.) Bean (family Araliaceae), *Hedychium gardnerianum* Sheppard ex Ker Gawl (family Zingiberaceae), *Heracleum mantegazzianum* Sommier & Levier (family Apiaceae), *Hiptage benghalensis* (L.) Kurz (family Malpighiaceae), *Imperata cykindrica* (L.) P. Beauv. (family Poaceae), *Lespedeza bicolor* Turcz. *L. cuneata* (Dum. Cours.) G. Don, or. *L. thunbergii* (DC.) Nakai (family Fabaceae), *Ligustrum japonicum* Thunb., *L. lucidum* Ait., *L. obtusifolium* Sieb. & Zucc., *L. ovalifolium* Hassk., *L. sinense* Lour., or *L. vulgare* L. (family Oleaceae), *Linaria dalmatica* (L.) Mill., *L. vulgaris* Mill. (family Scrophulariaceae), *Liriope muscari* (Decne.) L. H. Bailey (family Liliaceae), *Lonicera×bella* Zabel, *L. fragantissima* Lindl. & Paxon, *L. japonica* Thunb., *L. maackii* (Rupr.) Herder, *L. morrowii* A.

Gray, *L. tatarica* L. (family Caprifoliaceae), *Lygodium japonicum* (Thunb.) Sw. and *L. microphyllum* (Cay.) R. Br. (family Lygodiaceae), *Leucaena leucocephala* (Lam.) de Wit. (family Fabaceae), *Lythrum salicaria* L. (family Lythraceae), *Mahonia bealei* (Fortune) Corrière (family Berberidaceae), *Melia azedarach* L. (family Meliaceae), *Microstegium vimineum* (Trin.) A. Camus family Poaceae), *Mimosa pigra* L. (family Fabaceae), *Miscanthus sinensis* Andersson family Poaceae), *Morella faya* Aiton (family Myricaceae), *Nandina domestica* Thunb. (family Berberidaceae), *Onopordum acanthium* L. (family Asteraceae), *Opuntia stricta* (Haw.) Haw (family Cactaceae), *Paulownia tomentosa* (Thnb.) Sieb. & Zucc. ex Zucc. (family Paulowniaceae), *Phyllostachys aurea* Carr. ex A.& C. Rivère (family Poaceae), *Pinus pinaster* Aiton (family Pinaceae), *Polygonum cuspidatum* Siebold & Zucc (family Polygonaceae), *Poncirus trifoliata* (L.) Raf (family Rutaceae), *Prosopis glandulosa* Torr. (family Fabaceae), *Psidium cattleianum* Sabine (family Myrtaceae), *Pueraria montana* (Lour.) Merr. (synonyms: *P. lobata* (Willd.) Ohwi, *P. montana* var. *lobata* (Willd.) Maesen & S. Almeida), family Fabaceae), *Pyrus calleryana* Decne. (family Rosaceae), *Ranunculus ficaria* L. (family Ranunculaceae), *Rhamnus cathartica* L. (Rhamnaceae), *Rosa bracteata* J. C. Wendl., *R. laevigata*, or *R. multiflora* Thunb., ex Murr. (family Rosaceae), *Rubus ellipticus* Sm. (family Rosaceae), *Schedonorus phoenix* (Scop.) Holub. (family Poaceae), *Schinus terebinthifolius Raddi* (family Anacardiaceae), *Securigera varia* (L.) Lassen (family Fabaceae), *Solanum viarum* Dunal (family Solanaceae), *Solidago canadensis* L. (family Asteraceae), *Sorhum halepense* (L.) Pers. family Poaceae), *Spathodea campanulata* P. Beauv. (family Bignoniaceae), *Sphagneticola trilobata* L. (family Asteraceae), *Spiraea japonica* L. f. (family Rosaceae), *Tamarix ramosissima* Ledeb. (family Tamaricaceae), *Striga asiatica* (L.) Kuntze (family Scrophulariaceae), *Taeniatherum caput-medusae* (L.) Nevski (family Poaceae), *Triadica sebifera* (L.) Small (synonym: *Sepium sebiferum* (L.) Roxb., family Euphorbiaceae), *Tussiliago farfara* L. (family Asteraceae), *Vernicia fordii* (Hemsl.) Airy-Shaw (family Euphorbiaceae), *Vinca major* L. or *V. minor* L. (family Apocynaceae), *Vitex rotundifolia* L. f. (family Lamiaceae), *Ulex europaeus* L. (family Fabaceae), *Wisteria floribunda* (Willd.) DC. or *W. sinensis* (Sims) DC. (family Fabaceae).

The invasive species may be any appropriate invasive insect. In some embodiments, the invasive insect is an ant species. In some embodiments, the invasive species *Acrolepiopsis assectella* (family Acrolepiidae), *Agrilus planipennis* (family Buprestidae), *Anomala orientalis* (family Scarabaeidae), *Anoplophora chinensis, A. glabripennis* (family Cerambycidae), *Apis mellifera* (family Apidae), *Autographa gamma* (family Noctuidae), *Bactrocera oleae* (family Tephritidae), *Bombus terrestris* (family Apidae), *Cactoblastis cactorum* (family Pyralidae), *Ceratitis capitata* (family Tephritidae), *Cinara cupressi* (family Aphididae), *Coptotermes formosanus, C. gestroi* (family Rhinotermitidae), *Curculio nucum, C. occidentis* (family Curculionidae), *Diuraphis noxia* (family Aphididae), *Dryocosmus kuriphilus* (family Cynipidae), *Epiphyas postvittana* (family Tortricidae), *Eristalis tenax* (family Syrphidae), *Halyomorpha halys* (family Pentatomidae), *Helicoverpa armigera* (family Noctuidae), *Homalodisca vitripennis* (family Coccinellidae), *Hylotrupes bajulus* (family Cerambycidae), *Incisitermes minor* (family Kalotermitidae), *Lasius neglectus* or *L. neoniger* (family Formicidae), *Leptinotarsa decemlineata* (family Chrysomelidae), *Leptoglossus occidentalis* (family Coreidae), *Linepithema humile* (family Formicidae), *Lymantria dispar dispar* (family Erebidae), *Mamestra brassicae* (family Noctuidae), *Monomorium destructor* (family Formicidae), *Monomorium pharaonis* (family Formicidae), *Myrmica rubra* (family Formicidae), *Nylanderia fulva* (family Formicidae), *Operophtera brumata* (family Geometridae), *Ostrinia nubilalis* (family Crambidae), *Oxycarenus hyalinipennis* (family Lygaeidae), *Pectinophora gossypiella* (family Gelechiidae), *Pieris brassicae* (family Pieridae), *Polistes dominula* (family Vespidae), *Rhizotrogus majalis* (family Scarabaeidae), *Rhynchophorus ferrugineus* (family Curculionidae), *Schistocerca nitens* (family Acrididae), *Scirtothrips dorsalis* (family Thripidae), *Sirex noctilio* (family Siricidae), *Sitophilus zeamais* (family Curculionidae), *Solenopsis invicta* or *S. saevissima* (family Formicidae), *Tetrops praeustus* (family Cerambycidae), *Thrips palmi* (family Thripidae), *Tremex fuscicornis* (family Siricidae), *Trogoderma granarium* (family Dermestidae), *Vespa velutina* (family Vespidae), *Vespula germanica* (family Vespidae), *Wasmannia auropunctata* (family Formicidae), or *Xyleborus glabratus* (family Curculionidae).

The natural pesticide may be applied in any appropriate manner. In some embodiments, a composition comprising the natural pesticides is applied to a water body and its adjacent wetland areas infested with salvinias. In some embodiments, a composition comprising the natural pesticides is applied to a structure (e.g., boats) to control salvinias. In some embodiments, a composition comprising the natural pesticides is applied to a subject or structure (e.g., boats) to prevent infestation of salvinias. In some embodiments, a composition comprising the natural pesticide is applied topically. In some embodiments, the natural pesticide is applied to the surface of the invasive plant. In some embodiments, the composition is sprayed onto the invasive plant. In some embodiments, the composition is spread around the invasive plant. In some embodiments, the composition is dissolved in water surrounding the invasive plant.

In some embodiments, the application of the natural pesticide may not add any exotic chemicals to the ecosystem of the invasive species. In some embodiments, a composition comprising the natural pesticide can be prepared by chopping, shredding, blending, and/or pressing fresh matter of the target invasive species without solvent. In some embodiments, a composition comprising the natural pesticide can be prepared by using the water in the treating water bodies and/or their adjacent wetland areas as the solvent for the extraction of dried plant matter. In some embodiments, a composition comprising the natural pesticide can be added with non-bioactive surfactants.

The natural pesticide may be applied manually or mechanically. After the chopping, shredding, bending, and expression process, the residues from the juice production from fresh plant matter are usually not viable and are safe to be dumped back into the water body in a mechanical operation.

In some embodiments, the natural pesticide may be preferably applied to control the invasive plant soon after it is produced. In some embodiments, the natural pesticide is best applied to control the invasive plant immediately or within several hours of its production. In some embodiments, the natural pesticide is preferably applied to control the invasive plant within a week of its production. In some embodiments, the natural pesticide especially in its aqueous form may be stored under refrigeration (4° C.) for months and effectively inhibit the invasive species. In some embodiments, the natural pesticide especially in its solid form may be stored under room temperature for months and can effectively inhibit the invasive species.

In some embodiments, the natural pesticide may be applied alone. In some embodiments, the natural pesticide may be applied in combination with one or more secondary agents. In some embodiments, the secondary agent may be formic acid, acetic acid, diquat (diquat dibromide), glyphosate, contact herbicides, other biocides, the *salvinia* weevil, or biocontrol agents.

The natural pesticide may be present in any appropriate concentration in the composition. In some embodiments, the composition contains 0.001, 0.01, 0.1, 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100% by weight or more of the natural pesticide. In some embodiments, the composition contains about 0.01 to about 0.5% by weight of the natural pesticide. In some embodiments, the composition contains about 0.1% by weight of endocide.

Also disclosed are the compositions as described herein, as well as kits containing the same.

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol "====" represents a single bond or a double bond. Thus, for example, the structure

includes the structures

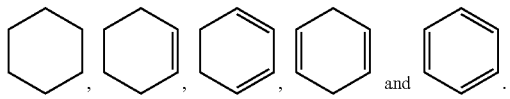

As will be understood by a person of skill in the art, no one such ring atom forms part of more than one double bond. The symbol "⌇", when drawn perpendicularly across a bond indicates a point of attachment of the group. It is noted that the point of attachment is typically only identified in this manner for larger groups in order to assist the reader in rapidly and unambiguously identifying a point of attachment. The symbol "◂" means a single bond where the group attached to the thick end of the wedge is "out of the page." The symbol "⦀" means a single bond where the group attached to the thick end of the wedge is "into the page". The symbol "⌇" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

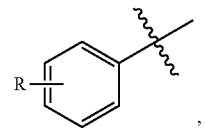

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

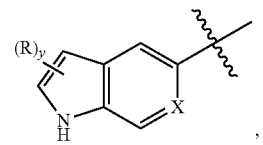

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$," or the class "alkene$_{(C≤8)}$," is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups CH$_3$ (Me), —CH$_2$CH$_3$ (Et), CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHC$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

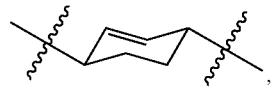 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

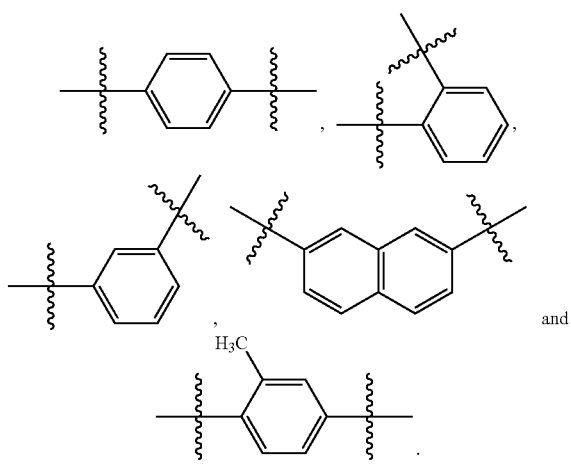

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

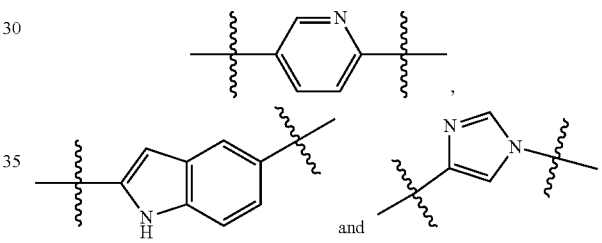

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively.

When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The term "invasive species" means a species (e.g., plants and animals including insects) that is either native or non-native (exotic) to the ecosystem and whose presence or introduction causes or likely causes economical or environmental harm or harm to human health.

"Invasive plant species" or "invasive plant" means either a non-native (exotic) or native invasive plant species.

"Invasive aquatic species" or "aquatic invasive species" means an invasive species that has living in, on, or next to water.

"Invasive aquatic plant" means an invasive plant species that has adapted to living in, on, or next to water, and that can grow either submerged or partially submerged in water.

"Water body" or "body of water" means any significant accumulation of water on a planet's surface, including but not limited to lake, pond, river, canal, creek, stream, brook, channel, ditch, bay, bayou, swamp, marsh, slough, bog, fen, wetland, harbor, inlet, lagoon, puddle, reservoir, strait, spring, swimming pool, or any container or structure with permanent or seasonal water.

"Salvinias" means aquatic or semi-aquatic fern species of the order Salviniales, including families Salviniaceae Reichenbach (*Salvinia* Séguier), Azollaceae Wettstein (*Azolla* Lamarck) (sometimes, *Azolla* is treated as a genus of the family Salviniaceae), and Marsileaceae Mirbel (*Marsilea* L., *Pilularia* L., and *Regnellidium* Lindm).

"Primary stage" or "primary growth stage" of giant *salvinia* means the plant growth occurs in the early stages of an infestation. The small, flat, and oval-shaped floating leaves lie in directare less than 15 mm in width.

"Secondary stage" or "secondary growth stage" of giant *salvinia* means the plant growth occurs in the secondary stages of an infestation. The floating leaves become slightly cupped and are more than 15 mm but less than 50 mm in width.

"Tertiary stage" or "tertiary growth stage" of giant *salvinia* means the plant growth occurs in the mature stages of an infestation. The floating leaves become tightly folded and are more than 50 mm in width when forced open. Tertiary plants may form a multilayered mat on the surface of the infested water body.

"Gland" means a cell, group of cells, or organ producing a secretion. "Exocrine gland" means any gland that secretes its products through a duct onto an epithelial surface.

"Trichome" refers to "glandular trichome" or plant gland in this invention and means glandular unicellular or multicellular appendages on the surface of various plant organs.

"Effective" amount or concentration means that amount or concentration which, when applied to a place or subject for controlling invasive species, is sufficient to affect the growth, reproduction, or spread of the species.

"Control" or "controlling" means inhibiting growth, reproduction, or spread of an invasive species in a place or subject. As used herein, the term "inhibition" of the species also refers to slowing, interrupting, arresting or stopping the species and does not necessarily indicate a total elimination of the species.

Some abbreviations used herein are as follows: $^1$H-NMR is proton nuclear magnetic resonance, $^{13}$C-NMR is carbon nuclear magnetic resonance, ADEQUATE is adequate sensitivity double-quantum spectroscopy, Al is aluminum, Ag is silver, B is boron, Ba is barium, Ca is cacium, As is arsenic, Cd is cadmium, HCOOH is formic acid, $CHCl_3$ is chroroform, $CH_2Cl_2$ is dichloromethane or methylene chloride, $CH_3COOH$ is acetic acid, $CH_3CN$ is acetonitrile, Co is cobalt, COSY is correlation spectroscopy, Cr is chromium, Cu is copper, DMSO is dimethyl sulfoxide, $EC_{50}$ means half maximal effective concentration, EtOH is ethanol, FAB MS is fast atom bombardment mass spectroscopy, Fe is iron, g is gram(s), gal is gallon(s), Glc is glucose, h is hour(s), $H_2O$ is water, Hg is mercury, HMBC is heteronuclear multiple-bond correlation, HPLC is high performance liquid chromatography, HRESIMS is High-resolution electrospray ionization mass spectrometry, HSQC is heteronuclear single quantum coherence spectroscopy, K is potassium, kg is kilogram(s), kPa is kilopascal(s), ICP is inductively coupled plasma, L is liter(s), $LD_{50}$ is defined as the dose required to kill half of the exposed fire ants, $LD_{90}$ is defined as the dose required to kill 90% of the exposed fire ants, m is meter(s), MeOH is methanol, mg is milligram, min is minute(s), Mg is magnesium, mL is milliliter(s), mm is millimeter(s), Mn is manganese, Mo is molybdenum, Na is sodium, NCPC is National Center for Pharmaceutical Crops of the Arthur Temple College of Forestry and Agriculture at Stephen F. Austin State University in Nacogdoches, Tex., USA, NMR is nuclear magnetic resonance, P is phosphorus, Pb is lead, pH is a measure of the acidity or basicity of an aqueous solution, psi is pounds per square inch, ppt is parts per thousand, S is sulfur, Se is selenium, sec is second(s), RT is room temperature (approximately at 20° C.), "tea bag" is a bag of ground dried plant matter, "tea brick" is compressed brick or pie of ground dried plan matter without bag, Zn is zinc, μg is microgram(s), μL is microliter(s), and μM is micromolar(s).

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10—$^1H$ and $^{13}C$-NMR Data (δ) of salviniside II.

FIG. 11—Giant *salvinia* (*Salvinia molesta*) can be totally eliminated by salviniside II isolated from giant *salvinia* within two weeks (with bars presenting standard deviations).

FIG. 25—Metal analysis of the dried plant matter, water extract powder, and its precipitated salts of giant salvinia (*Salvinia molesta*) by Thermo Scientific ICAP 7200 ICP-OES.

DESCRIPTION OF ILLUSTRATIVE EMBODIMENTS

Control of invasive species by its endogenous metabolites has never been proposed or used.

The inventors recently discovered that some aquatic plants, trees, fire ants, or termites experienced slow autocide by their own toxins that were released into the environment by themselves or other individuals within the same species. It was known that some bioactive secondary metabolites may accumulate in glands (e.g., epidermal glandular trichomes of plants or exocrine glands of insects). These compounds usually do not interrupt normal growth of the producing species due to their non-bioavailability. However, it was discovered that external application of these bioactive agents to the parent species will inhibit and even eliminate the species. Further, the parent species may be more sensitive to its endogenous toxic metabolites than other species.

As a proof of principle, the inventors found that endocides from giant *salvinia* and extracts of least duckweed (*Lemna minuta*) (Lernnaceae) can eliminate existing giant *salvinia* quickly and prohibit plant growth for at least six months in controlled conditions. The experiments showed that the effective materials used to extract bioactive agents to control *Salvinia* spp. include any ground dry biomass matters of *Salvinia* and *Lemna*. Experiments also found that the fresh biomass of *Salvinia* and *Lemna*, particularly chopped can also be useful to extract bioactive agents or direct application in control of *Salvinia* spp. Raw and unground dry plant matter can also be used in a similar manner, and it is believed that any other plant species containing the active agents as described herein could be useful in production of biocides to control *Salvinia* spp. This method is useful for controlling invasive aquatic plants, but this method also has potential in territorial plants and endophytic fungi. It is especially useful for controlling invasive plants with trichomes as the primary accumulation sites of bioactive compounds.

*Salvinia* species are rootless, free-floating aquatic ferns and they are well-known for their extremely water-repellent floating leaves. On the upper surfaces of the floating leaves of *S. molesta*, four multicellular glandular trichomes have their apical cells connected to form egg-beater structures. The arrows point to the egg-beater structures of trichomes which were removed by blade. The root-like submerged leaves are highly branched with multicellular trichomes and on which sporocarps developed.

Figure 2:
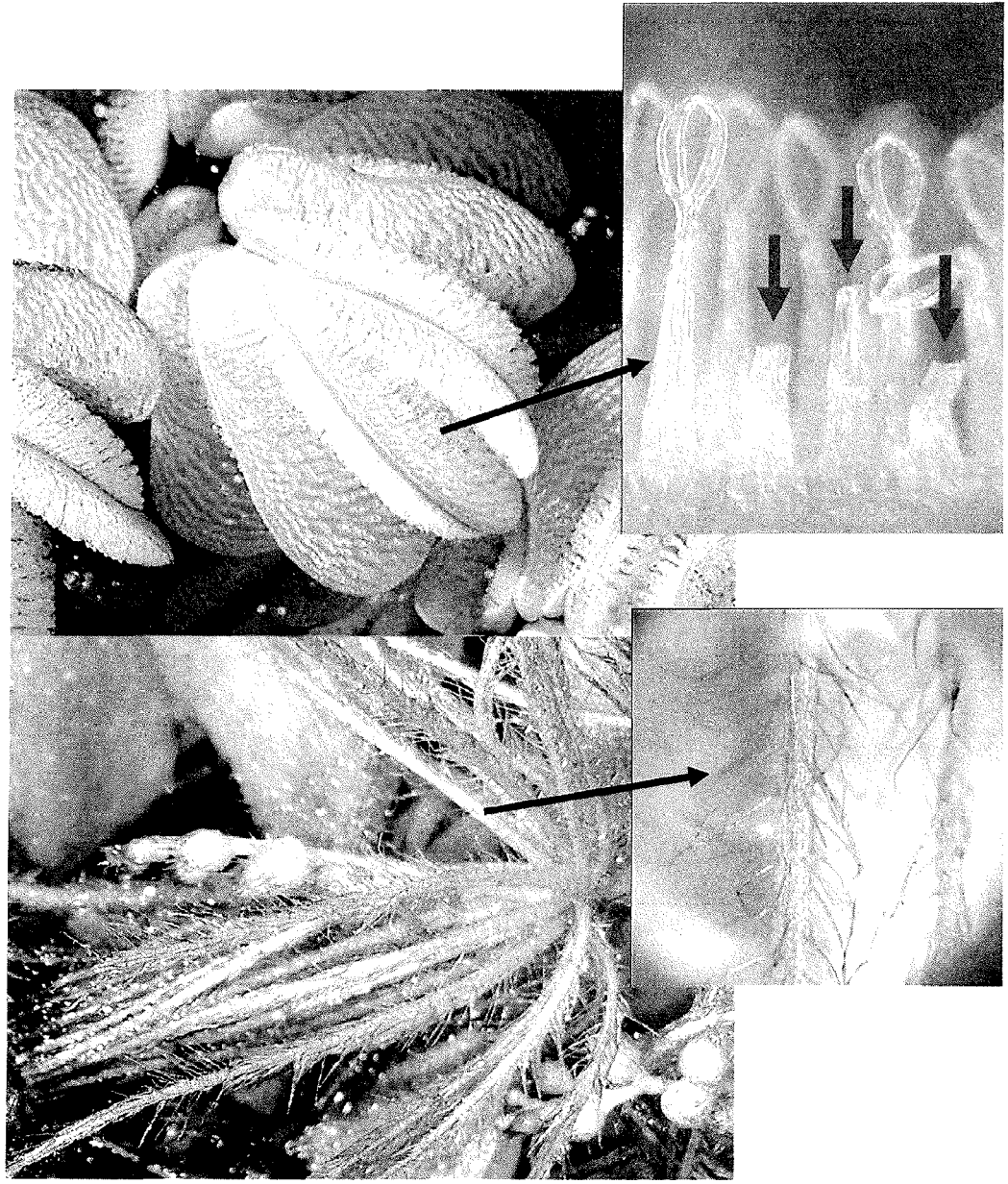
FIG. 2—Salvinia species are rootless, free-floating aquatic ferns and they are well-known for their extremely water-repellent floating leaves. On the upper surfaces of the floating leaves of S. molesta, four multicellular glandular trichomes (called "trichomes") have their apical cells connected to form egg-beater structures. The three short arrows point to the egg-beater structures of trichomes which were removed using a blade. The root-like submerged leaves are highly branched with multicellular trichomes on which sporocarps develop.

Previous experiments found that the active agents of giant *salvinia* are primarily accumulated in trichomes which are usually intact, and the plant can avoid poison by these toxins (Li et al., unpublished data). However, *Salvinia* spp. are well-known for their water-repellent floating leaves because of the leaves are densely covered with peculiar trichomes (Barthlott et al. 2009). On the upper surfaces of floating leaves of *S. molesta*, four multicellular trichomes have their apical cells connected to form egg-beater structures (FIG. 2). The root-like submergered leaves also have dense multicellular trichomes (FIG. 2). The basal cells of the trichomes in *S. molesta* are covered with wax (Barthlott et al. 2009). Therefore, the bioactive compounds in trichomes of the living plants are not released into the water because of this water-repellent feature. The removal or damage of the apical cells (egg-beater structures) of trichomes (FIG. 2) will not only release the chemicals in storage but also allow water to access the floating leaves to soak the bioactive agents out. This invention emphasizes that breaking the trichomes (e.g., mechanical treatments such as grinding, blending, squeezing, or heavily washing plant tissues) is necessary for effective extraction of the bioactive agents from giant *salvinia*.

Both water and organic solvents (e.g., ethanol) can be used to effectively extract the bioactive agents. The most effective solvent to dissolve these bioactive entities, fractions, or extracts to control *Salvinia* spp. is water, but organic solvents could also be useful in application. Plants respond to the treatment more quickly at higher temperatures than at lower temperatures (RT).

Figure 34:
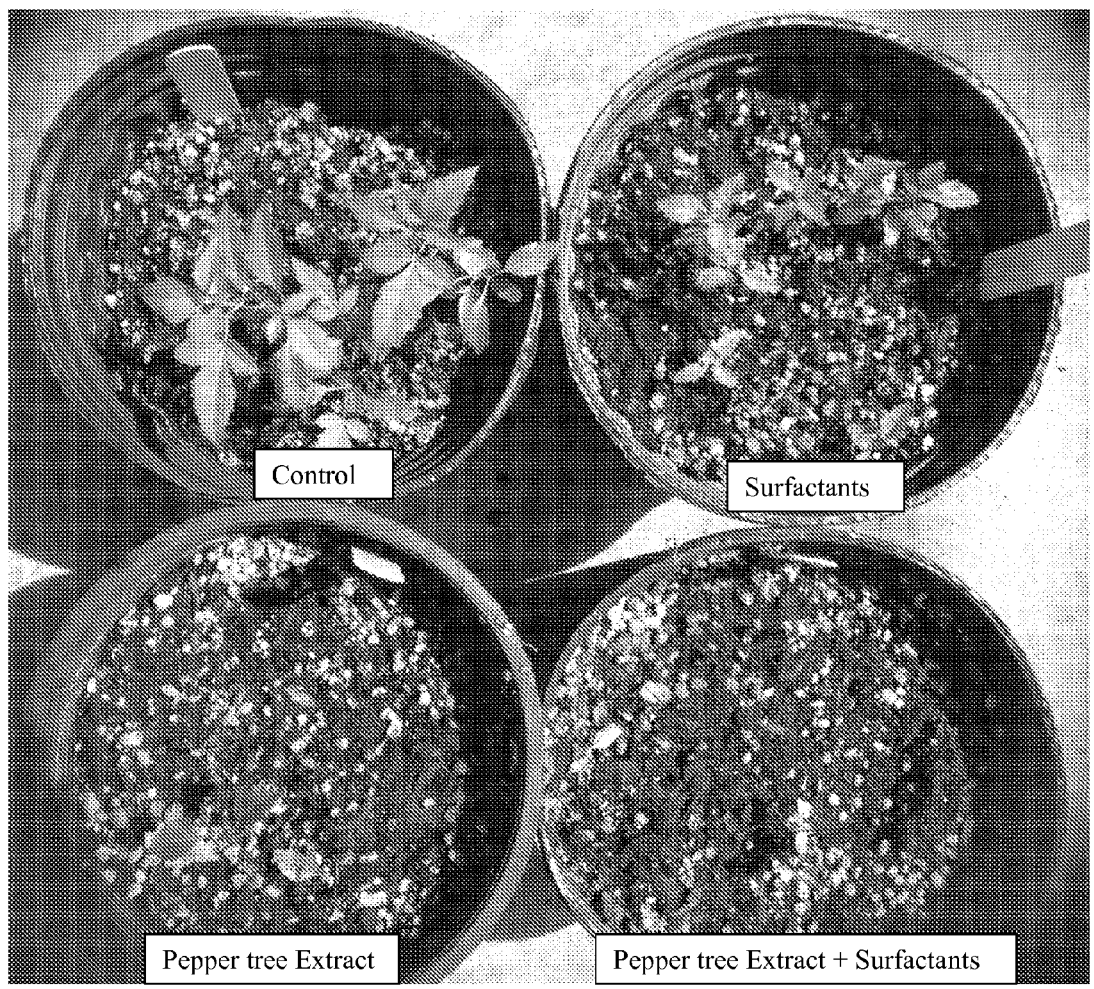
FIG. 34—The photograph shows that 3-week-old Brazilian pepper tree (*Schinus terebinthifolius* Raddi) seedlings had significant damage after the first treatment with 10% Brazilian pepper tree extract or Brazilian pepper tree extract with surfactants in comparison with those in control and surfactants treatment. By the end of the 4th week, all six pepper tree seedlings were dead following the pepper tree extract with surfactants treatment and five seedlings were dead and one had dead apical bud and young leaves after treated by the pepper tree extract.

The endocidal functions are not only in giant *salvinia*, a fern species in the phylum Pteridophyta of the kingdom Plantae, but also discovered in Brazilian pepper tree and Chinese tallow tree, two tree species in the phylum Flowering Plants of the kingdom Plantae and the red imported fire ant and subterranean termite, two insect species from the phylum Arthropoda of the kingdom Animalia. The plant growth of Brazilian pepper tree seedlings had significant damage by the 10% ethanol extract of Brazilian pepper tree fruits after the first treatment (FIG. 34). Four weeks later, all six Brazilian pepper tree seedlings were killed by the extract with surfactants and five of the six seedlings treated by the extract alone were dead with one significantly injured. The seedlings of sweetgum (*Liquidambar styraciflua* L.) (family Altingiaceae) and Shumard oak (*Quercus shumardii* Buckland) (family Fagaceae) as well as poison ivy (*Toxicodendron radicans* (L.) Kuntze or *Rhus toxicodendron* L.) of the same family with Brazilian pepper tree were not impacted by the Brazilian pepper tree extract. Furthermore, the Brazilian pepper tree seedlings were no inhibited by either surfactants or the 10% ethanol extract of Chinese tallow tree (*Triadica sebifera* (L.) Small) fruits.

The ethanol extract of the fruits of Chinese tallow tree (*Triadica sebifera* (L.) Small) (Eurporbiaceae) inhibited and even killed young seedlings of the tallow tree. However, the tollowtree extract did not cause any damage in the seedlings of Chinese privet (*Ligustrum sinense* Lour.) of the family Oleaceae. Further, the Chinese privet extract did not damage the tallow tree seedlings.

Formic acid commonly occurs in ants (family Formicidae), termites (Isoptera), and some other insects. The organic acid is accumulated in exocrine glands of these insects and serves as defensive weapon fighting against attackers. The formic acid can be as concentrated as 60% of the secretion of ants, and workers can contain as much as 2 mg each (Morgan 2008). The acid is a known natural pesticide. Like their enemies, however, both the red imported fire ants and subterranean termites could not avoid toxicity of formic acid during external topical or fumigation application (FIGS. 37-40).

Figure 36:
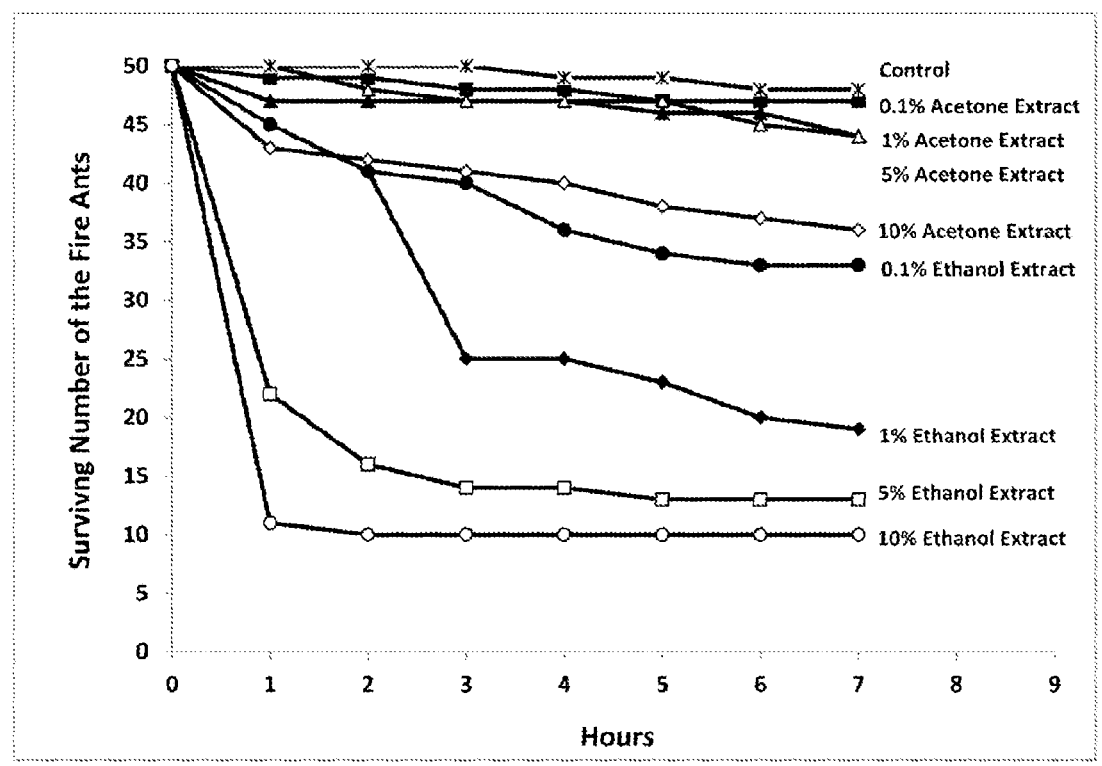
FIG. 36—The diagram shows the impacts of acetone extract and ethanol extract of the red imported fire ant (*Solenopsis invicta* Buren) on the workers of the red imported fire ant. The ethanol extract showed more significant toxicity against the fire ants than the acetone extract. During the 7 h of contact toxicity bioassays, an average of approximately 60%, 70%, or 80% of the 50 fire ants in contact with 1%, 5%, or 10% ethanol extract were dead, respectively.

This invention found that the red imported fire ants can be killed by the extracts of the fire ants (without formic acid), particularly ethanol extract (FIG. 36). However, the ethanol extract (primarily piperidine alkaloids) of the fire ants had selective activity against the ants and showed no effects on the subterranean termite. The fire ants and termites are in different superorders (Endopterygota and Exopterygota, respectively).

Both formic acid and acetic acid have been used as herbicides to control weeds. This invention found that formic acid is more effective than acetic acid to control giant *salvinia*. Formic acid at 0.05% concentration killed approximately 50% of the giant *salvinia* plants within 24 h. It is more effective in *salvinia* control when combined with giant *salvinia* extracts.

This invention reports that bioactive compounds in giant *salvinia* are primarily accumulated in glandular trichomes on the leaf surface. It is known that the surface of the fruits (drupes) of Brazilian pepper tree is also covered by glandular trichomes (Carmello-Guerreiro and Paoli 2002). Chinese tallow tree has glands on leaf stalks. Formic acid is a primary venom compound commonly accumulated in the abdominal exocrine glands of ants and termites. In all these five described distant-related species, glands act accumulation sites of bioactive compounds that play important roles in endocidal function of the species so that the bioactive compounds do not poison the producing species in normal growth. Thus, the endocide may have effects especially in the species with glands as accumulation sites of bioactive compounds.

Furthermore, this invention disclosed that application of endocides at low concentrations (dosages) can control partial growth of an individual (e.g., a specific cell(s), tissue(s), or organ(s)) of the producing species rather than killing or eliminating the species.

Application of endocides at low concentrations (dosages) may produce abnormal morphogenesis. In some embodiments, the endocides may induce mutations. In some embodiments, the induced mutations may be used to produce desirable genotypes.

In some weeds and crops, autotoxicity reports are primarily on effects in the seed germination, growth, and yield of the producing plants and the resulting soil sickness and replanting problems. The reported autotoxic chemicals had weak activity against the parent species but they are more potent inhibitory effects on other non-closely-related species (e.g., species in other genera, families or orders) than on the producing plants. Therefore, it is impossible to develop a biocidal product to selectively control the producing invasive species. Further, it is commonly believed that a species can avoid self-toxicity by its endogenous toxic metabolites and the toxic compounds are primarily used for defense to protect itself from enemies. The present invention discovered that some invasive species with glands as accumulation site of their autotixic chemicals cannot avoid autotoxicity by its own metabolite(s) when externally applied. More importantly, these parent species (and its closely-related species) are more sensitive to its endogenous toxic metabolites than the other tested species in different genera, families or orders. The mechanism of selective activity of the autotoxic chemicals to the producing species is not clear but it seems that these chemicals in glands are not available to the normal growth and development of the species.

This discovery provides the foundation for development of a novel endocide product to selectively control an invasive species over the other species. It further suggests that how to avoid endogenous autotoxicity by the toxic metabolit(s) must be the priority for the producing species in the development and evolution. To protect itself from enemies by "defensive" metabolite(s) become possible only when the producing species can avoid endogenous autotoxicity.

A. Natural Pesticide Compositions

1. Endocides

In some embodiments, the present invention relates to compositions containing endocides and methods of controlling the growth of invasive species using the same. An endocide (endogenous biocide) is a biocide derived from an endogenous bioactive agent (e.g., secondary metabolite) that does not cause apparent poison in normal growth of the producing species but will poison or inhibit and even eliminate the parent species when induced in producing species. It can selectively eliminate the parent species (and possiblly its closely-related species) when externally applied. The dead tissues of species caused by an endocide will enhance the endocidal function to the species. The endocide can be developed as either a pure single entity or as a mixture of compounds (e.g., a fraction of extract, an extract, a dry or fresh matter of species). The endocides can be obtained in liquid or solid format from fresh or dried matter by any effective extraction methods (e.g., expression, distillation, solvent extraction, infusion, decoction, and percolation). For aquatic species, endocides are usually water soluble and can be dissolved in water in application. Endocides may have effects on the invasive species in all or some growth stages and all or some tissues.

Figure 1:
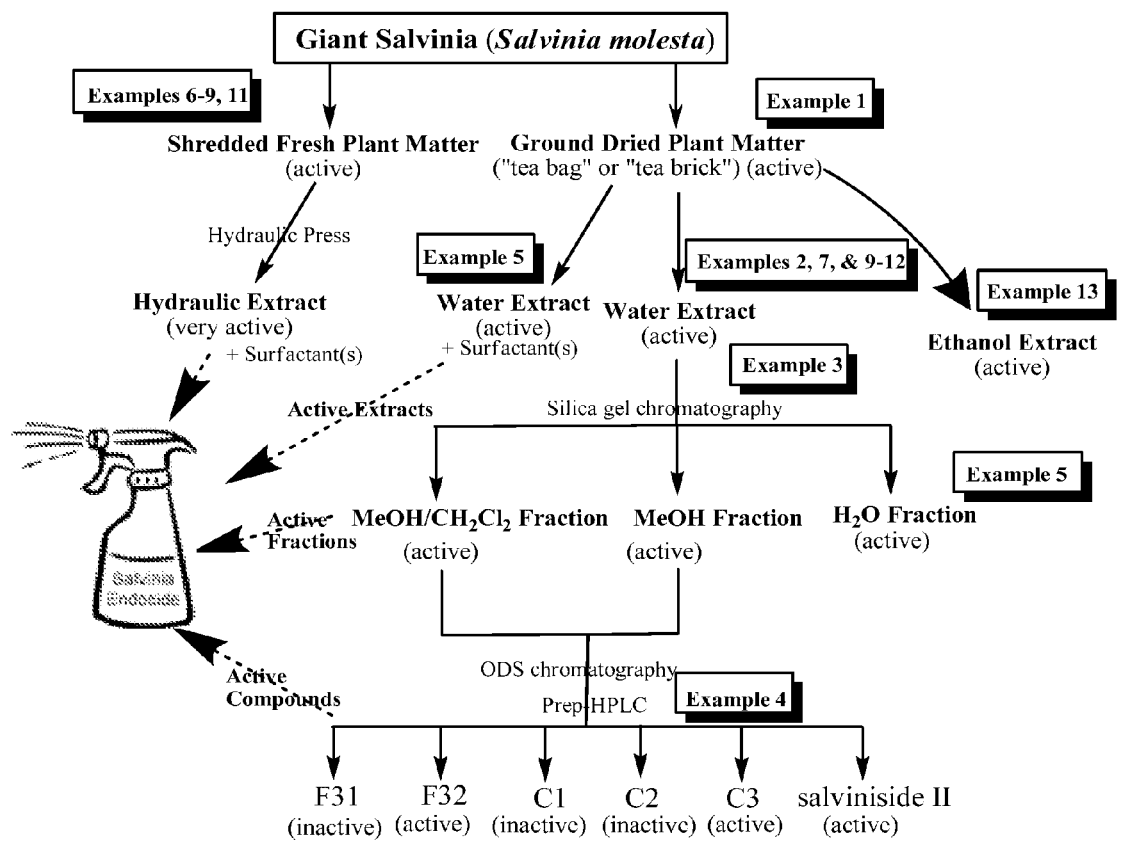
FIG. 1—The scheme shows the discovery and development process and related experiments of endocides from invasive giant salvinia (Salvinia molesta) as described herein (inactive: not able to inhibit the growth of giant salvinia at all; active: able to fully inhibit the growth of giant salvinia at high concentrations; very active: able to fully inhibit the growth of giant salvinia at low concentrations).

The endocide development process is summarized in FIG. 1. As an example, the inventors studied giant *salvinia* plants. It was found that endocides derived from either dried or fresh plant matter of giant *salvinia* can effectively control the invasive species in all growth stages (primary, secondary, and tertiary stages) (Examples 1-8). It was found that dry plant matter of giant *salvinia* can fully eliminate giant *salvinia* plants when adequate dried ground matter of giant salvina is placed in the water (FIG. 3).

Figure 3:
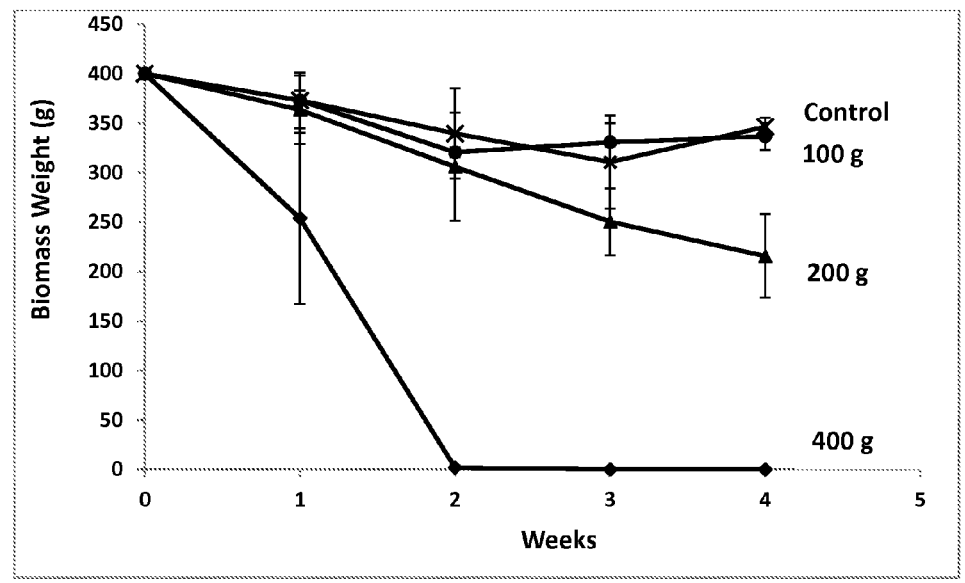
FIG. 3—Effects of dry plant matter of giant salvinia (Salvinia molesta) ("tea bag") on the growth of giant salvinia in containers during the four weeks of greenhouse experiments (with bars presenting standard deviations).
Figure 5:
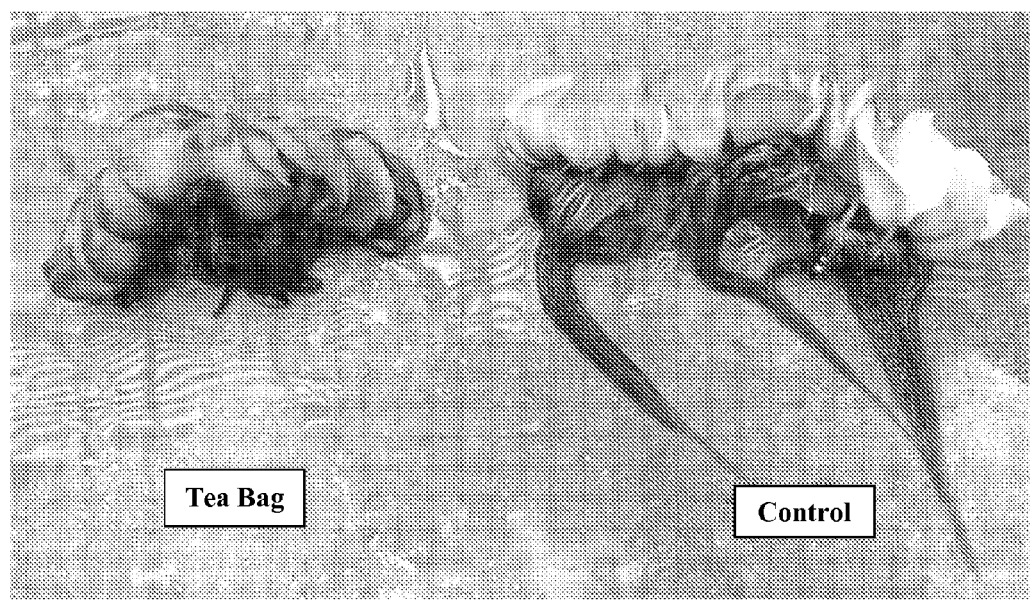
FIG. 5—The photograph shows that the root-like submerged leaves of giant salvinia (Salvinia molesta) were totally damaged before the floating leaves turning into brown and dead after the "tea bag" treatment.
Figure 6:
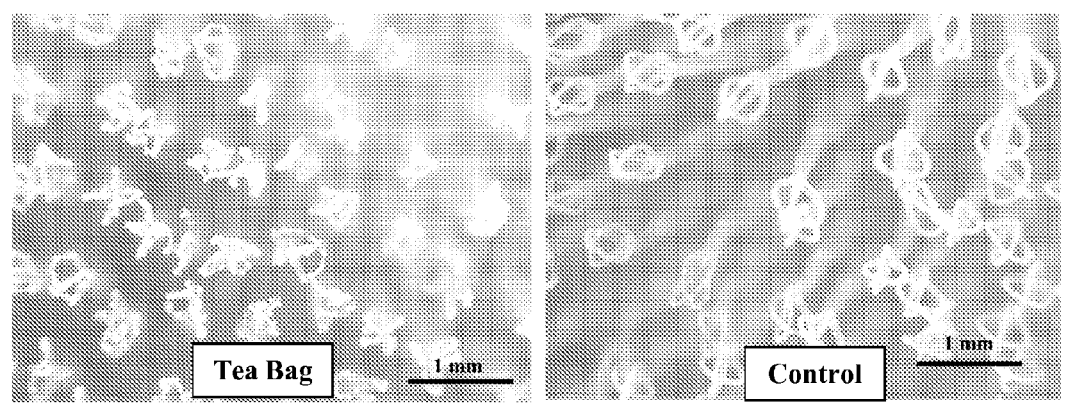
FIG. 6—The photograph shows the wilted trichomes on the upper surfaces of the floating leaves of giant *salvinia* (*Salvinia molesta*) caused by the water extract from "tea bag" (left) in comparison with those in the normal plant growth condition (right). The wilted trichomes released autotoxic compounds and enhanced the endocidal function of "tea bag".

FIG. 3 illustrates that the minimum effective concentration to inhibit giant *salvinia* is between 4 and 8 g of dried plant matter per liter of water. About 50% of giant *salvinia* plants were killed at the concentration of 8 g/L. The *salvinia* plants were fully eliminated at 16 g/L within two weeks in the greenhouse (FIGS. 3 and 4), and no new or living *salvinia* plants were found within the six months of observation thereafter. This demonstrates that giant *salvinia* contains some agents that are toxic to the parent plants and that these agents can fully eliminate and inhibit the growth of salvinias at higher concentrations. The "tea bag" treatment killed the salvinias bottom-up by damaging the root-like submerged leaves of giant *salvinia* first (FIG. 5). Then the trichomes on the upper surfaces of the floating leaves of giant *salvinia* were wilted following the damage of the submerged leaves (FIG. 6). The wilted trichomes released autotoxic compounds and thus enhanced the endocidal function. The "bottom-up" killing style of the "tea bag" is particularly effective in a shallow and still water body infested with multi-layers of *salvinia* mat because the dead tissues of the bottom layer of salvinias killed by the "tea bag" would enhance the endocidal function to eliminate the next layer of the *salvinia*.

Figure 27:
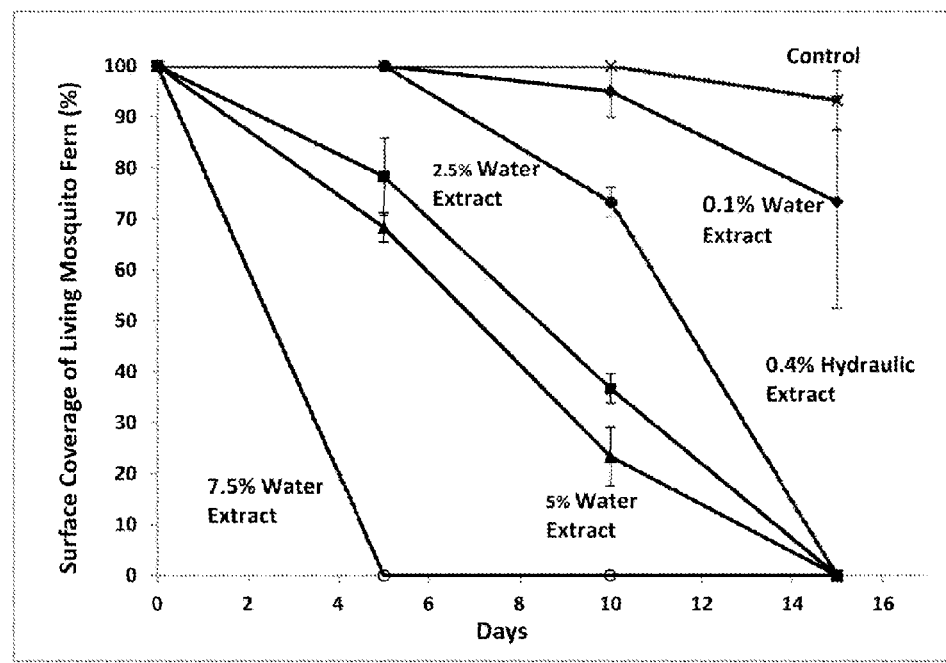
FIG. 27—The diagram shows that the plants of Carolina mosquito fern (*Azolla caroliana*) was inhibited by the water extract at higher concentration (2.5% or higher, in dry weight) (with bars presenting standard deviations).

In some cases, because higher effective concentration of dried ground plant *salvinia* is needed to inhibit giant *salvinia*, and some natural factors in lakes and other water systems may dilute the concentrations or prohibit the occurrence of higher concentrations, it may be necessary to place dried and ground matter of giant *salvinia* in nylon or other net bags to have effective concentrations for the controlling target. In another cases, it was found that unground raw plant matter of giant *salvinia* at 16 g/L was less effective than ground matter and took more than five times longer to kill the plants.

To identify more effective agents from giant *salvinia* to control the growth of the plant, experiments were conducted with a particular focus on water extracts of giant *salvinia* (FIG. 1). It was confirmed that water extract of giant *salvinia* can successfully eliminate giant *salvinia* within 13 weeks at RT and prohibit the plant growth for at least eight months (FIG. 7), MeOH/$CH_2Cl_2$ and MeOH fractions eliminated all giant *salvinia* plants within two weeks (FIG. 8), new compound salviniside II also eliminated the giant salvina plants (FIGS. 9-11), and the ethanol extract of giant *salvinia* inhibited the growth of giant *salvinia* effectively. In summary, while the bioactive MeOH/$CH_2Cl_2$ and MeOH fractions and salviniside II compound are more effective, each extract or fraction thereof can be produced as endocides to eliminate and prohibit giant *salvinia.*

The experiments showed that extraction temperature and solvent (water) volume significantly contributed to the quality of water extracts and its fractions. The higher extraction temperature (60° C.) and higher rate of solvent volume to dried plant matter weight (43.8:1, v/w) yielded an extraction rate of approximately 8.8% (Example 5), and the lower temperature (RT) and lower rate of solvent volume to dried plant matter weight (17.2:1, v/w) yielded a 6.25% extraction rate (Example 3). Also, $H_2O$ fraction from the Example 5 (FIG. 14) was much more effective than that from Example 3 (FIG. 8).

The experiments indicate that extracts (juice) expressed from the fresh matter of giant *salvinia* (e.g., by hydraulic press) can be directly used in control of giant *salvinia* (FIGS. 16-20). The yield rate of extracted juice from the fresh matter of giant *salvinia* may depend on the growth stage and moisture content of the harvested plant matter and approximately 50% of the plant matter in fresh weight. The extracts expressed from the fresh matter of giant *salvinia* (0.28% or 0.40% in concentration) were even more effective than the concentrated water extracts (5%) from the dried matter of giant salvina in inhibition of the species (FIG. 20). The HPLC analysis showed that the hydraulic extracts had more complex chemical constituents in both detection conditions and higher contents of some compounds and even unique compounds may be responsible for the strong bioactivity of the hydraulic extract (FIGS. 21 and 22). Like aquatic herbicides, addition of a surfactant to the endocide may help it wet and penetrate the floating leaves with water-repellent trichomes and thereby result in more effective spray applications (FIGS. 14, 16, 17, and 20). In both experiments, all plant tissues of giant *salvinia* after hydraulic extraction were dead and there was no new plant growth in the cultured plant residues from the hydraulic extraction within six weeks of the experiment (FIG. 19). The plant residues from the extraction of the fresh matter are safe to be discarded into the treated water bodies. Therefore, extracts from the fresh matter of giant *salvinia* are desirable for use as endocides to eliminate and prohibit giant *salvinia*. In its concentrated form, the extract juice from fresh matter may also be effective to control *salvinia*. Because the degraded hydraulic extract after long-storage might be still useful in control of salvinias, it is speculated that diluted several times with water, the newly produced extract juice from the fresh matter may also be effective to control salvinias.

According to the experiments, aqueous products of endocides may be better to be stored under refrigeration (4° C.) while powder samples can be stored at RT for relative stability. In general, the $H_2O$ fraction was more stable than the water extract or the hydraulic extract in storage. The extract powder stored at RT for 26 weeks had approximately 70% of the total peak area of that in the newly prepared extract (FIG. 12).

The hydraulic extract stored under refrigeration (4° C.) is more stabilized than that stored at RT, and on the 14th week of the storage it contained approximately 60% of the total peak area of that in the newly-prepared extract, and it was still active in inhibition of giant *salvinia* (FIGS. 23 and 24). After being stored at RT for 26 weeks, the $H_2O$ fraction powder preserved over 90% of its chemical contents, and its liquid form stored in a refrigerator (4° C.) still had approximately 90% of the total peak area of the newly prepared sample (FIG. 13).

*Salvinia* spp. have the potential to hyperacumulate a wide range of heavy metals from water and have high levels of tolerance to the metals according to the literature. The ICP analysis showed that the concentrations of the main metals in the water extract powder are much lower than the toxic concentrations in the metal solutions to grow *Salvinia* spp. as reported (10 to 100 ppm). For example, the concentrations of cadmium (Cd), chromium (Cr), cobalt (Co), copper (Cu), lead (Pb), and molybdenum (Mo) in the dry extract powder are less than 1 ppm in dry weight, and the concentration of copper (Cu), iron (Fe), lead (Pb), and zinc (Zn) in the dry extract powder is 5.310525, 228.0387, 2.515505, and 166.7952, respectively (FIG. 25). The concentrations of these metals in the application of endocides were diluted by 20 to 1,000 times when using water extract at its spray concentration (0.1 to 5% in dry weight) in control of *salvinia*. Thus, toxic metals are not the major active ingredients of *salvinia* endocides, i.e., they are not responsible for inhibiting the survival and growth of giant *salvinia.*

The experiment showed that isolated salts account for 6.25% of the water extract from the dried matter of giant *salvinia* in dry weight. Of the 5% water extract (the highest concentration used in the experiments), the concentration of the salts is 0.3125% (3.125 ppt). The experiment indicated that even the spray of the salts at even 5% concentration (50 ppt) of the salts had no significant impact on the growth of giant *salvinia*. Therefore, the salts precipitated from the water extract are not the major active ingredients responsible for the bioactivity of water extracts (FIG. 25).

The experiments indicated that both spraying and dissolving these agents were effective. A similar approach may be taken to identify endocides in all invasive plant species, including but not limited to *Salvinia adnata, S. auriculata, S. biloba, S. cucullata, S. cyathiformis, S. hastata, S. herzogii, S. martynii, S. minima, S. molesta, S. natans, S. nymphellula, S. oblongifolia, S. radula, S. rotundifolia, S. sprucei, Azolla caroliniana, A. cristata, A. circinate, A. filiculoides, A. japonica, A mexicana, A. microphylla, A. nilotica, A. pinnata, A. rubra, Lemna minuta*, or *Eichharnia crassipes.*

The water extract of dried matter of giant *salvinia* can totally eliminate the plants of the floating fern (*S. minima*), a species within the same genus with giant *salvinia*, at either 0.1% or 0.5% within six weeks (FIG. 26). Both water extracts and hydraulic extracts of giant *salvinia* had significant impacts on the growth of Carolina mosequito fern (*Azolla caroliniana*), a fern species in a different family but the same order with the genus *Salvinia*. The hydraulic extract (0.4%) killed 100% of the Carolina mosquito fern plants by the end of the 15th day (FIG. 27). The water extract at higher concentrations (2.5, 5, or 7.5%) killed 100% of the Carolina mosquito fern plants within the 15 days of experiment (FIG. 27). At even 5% concentration, the water extract of the dried matter of giant *salvinia* did not impact the growth of herbaceous flowering plants (e.g., least duckweed (*Lemna minuta*), Brazillan watermeal (*Wolffia brasillensis* Weddell), water hyacinth (*Eichharnia crassipes*), and *hydrilla* (*Hydrilla verticillate* (L.f.) Royle)), and native confers (e.g., bald cypress (*Taxodium distichum* (L.) Rich.) and loblolly pine (*Pinus taeda* L.)). The endocide of giant *salvinia* has obvious selective activity against salvinias (order Salviniales) especially the species of family Salviniaceae, but it has no impacts on seed plants (spermatophytes) including angiosperms (flowering plants) and gymnosperms.

2. Natural Pesticides Derived from Second Species

Figure 28:
FIG. 28—The photograph shows that all giant salvinia (*Salvinia molesta*) plants were eliminated within 13 weeks after the treatment with water extract of the dried matter of least duckweed (*Lemna minuta*). The plants in the top row served as control without any treatment, and each plant has developed significant new growth. The plants in the middle row were treated with 0.01% water extract of duckweed, and some plants have developed new growth. The plants in the bottom row were treated with 0.1% water extract of duckweed, and all plants are dead and no any new growth was developed from any plants during the eight months of observation. The three columns represent three replications of the experiment.
Figure 29:
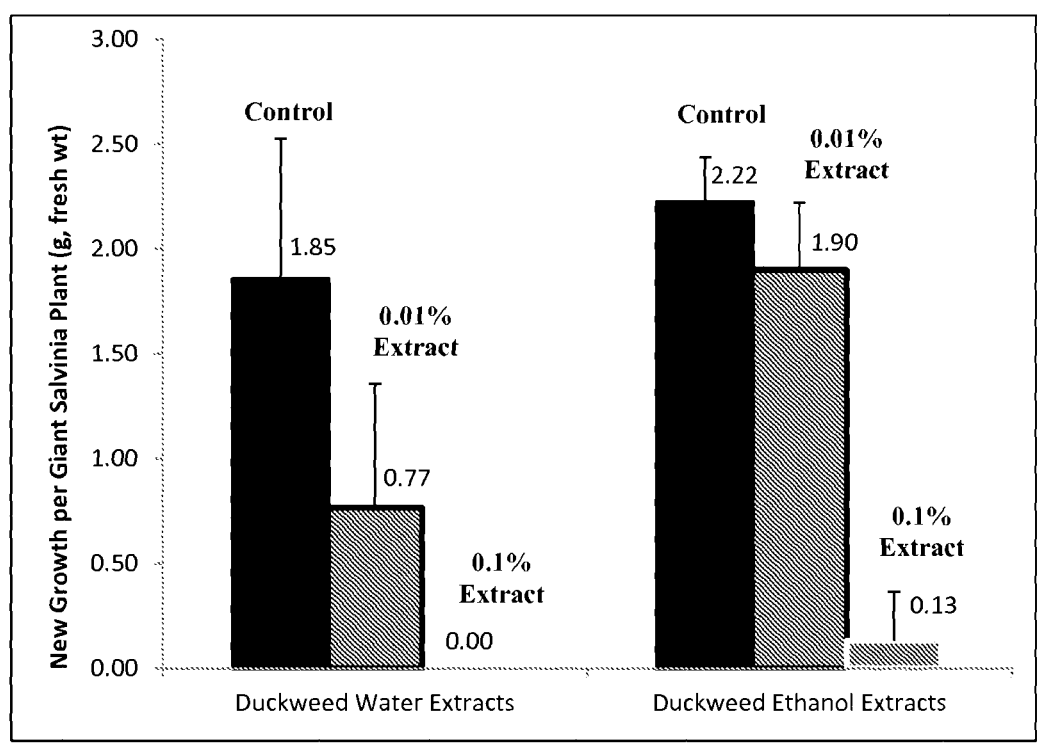
FIG. 29—The diagram shows the new growth per plant of giant salvinia (*Salvinia molesta*) by the end of the 13th week after treatment with water or ethanol extract of dried matter of least duckweed (*Lemna minuta*) in comparison with untreated plants (control) (with bars presenting standard deviations).
Figure 30:
FIG. 30—The picture shows that all giant salvinia (*Salvinia molesta*) plants were eliminated within 13 weeks after treatment with ethanol extract of the dried matter of least duckweed (*Lemna minuta*). The plants in the top row served as control without any extract treatment, and each plant has developed significant new growth. The plants in the middle row were treated with 0.01% ethanol extract of duckweed, and plants have developed new growth. The plants in the bottom row were treated with 0.1% ethanol extract of duckweed, and 12 plants are dead and only 3 plants have developed any new growth. However, all these 15 plants treated with 0.1% ethanol extract of least duckweed were dead by the end of 15 weeks of the experiment and no new growth occurred thereafter during the eight months of observation. The three columns represent three replications of the experiment.
Figure 31:
FIG. 31—The photograph shows that some floating fern (*Salvinia minima*) plants were eliminated within the 13 weeks after the treatment with water extract of the dried matter of least duckweed (*Lemna minuta*). The plants in the top row served as control without any extract treatment. The plants in the middle row were treated with 0.01% ethanol extract of duckweed. The plants in the bottom row were treated with 0.1% ethanol extract of duckweed. The three columns represent three replications of the experiment.
Figure 32:
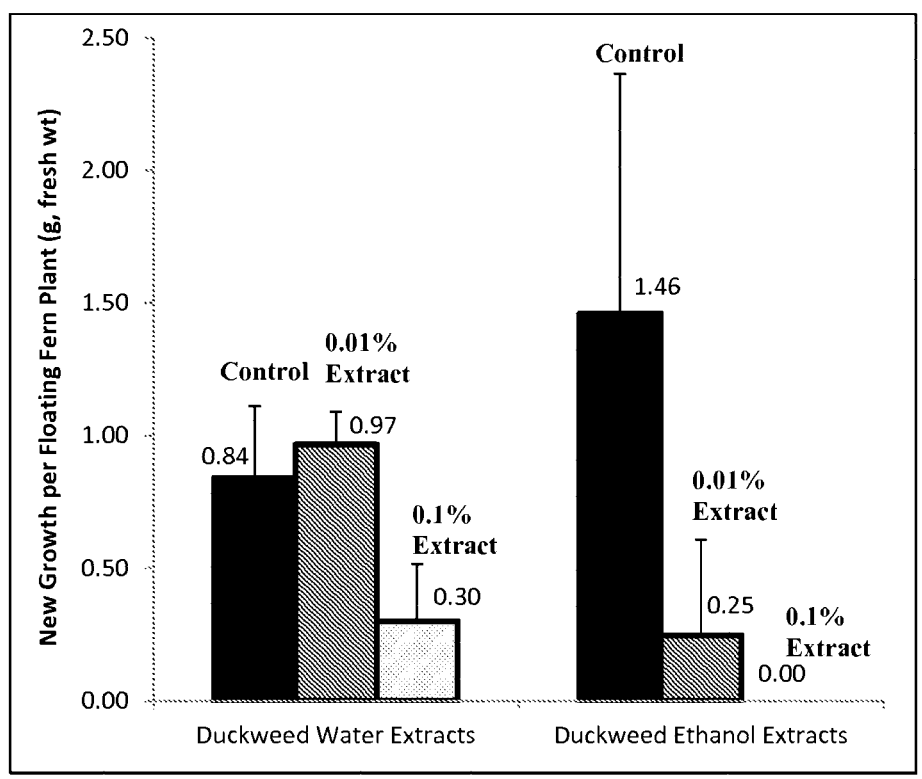
FIG. 32—The diagram shows new growth per plant of floating fern (*Salvinia minima*) by the end of the 13th week after treatment with water or ethanol extract of the dried matter of least duckweed (*Lemna minuta*) in comparison with untreated plants (control) (with bars presenting standard deviations).
Figure 33:
FIG. 33—The photograph shows that all floating fern (*Salvinia* minima) plants were eliminated by the end of 13 weeks after the treatment with 0.1% ethanol extract of the dried matter of duckweed (*Lemna minuta*). The plants in the top row served as control without any treatment, and there is significant new plant growth. The plants in the middle row were treated with 0.01% ethanol extract of duckweed, and new growth can be observed. The plants in the bottom row were treated with 0.1% ethanol extract of duckweed, and some plants are dead and minimal new growth can be observed. The three columns represent three replications of the experiment.

Least duckweed (*Lemna minuta*) is a noxious invasive species itself. Its water extract successfully eliminated giant *salvinia* and prohibited plant growth for at least eight months (see Example 14) (FIGS. 28 and 29). Ethanol extract of duckweed was also effective to control giant *salvinia* (FIG. 30). Duckweed extracts were also able to control *Salvinia minima* (FIGS. 31-33).

B. Examples

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Elimination and Prohibition of Giant *Salvinia* (*Salvinia Molesta*) by the Water-Extracted Dried Matters of Giant *Salvinia*

General Experimental Procedures:

Air-dried whole plants of giant *salvinia* were ground to a coarse powder and placed in nylon net bags (called "tea bags"). Each of 12 containers had 400 g of living healthy plants of giant *salvinia* in all growth stages (primary, secondary, and tertiary stages) in 25 L of tap water in the greenhouse (30° C. during the day time and 20° C. at night). Three containers had no treatment to serve as controls. The first treatment group had three containers and each had one bag of 100 g of giant *salvinia* dried matter in the water. The second group of three containers had one bag of 200 g of giant *salvinia* dried matter, and the last group of three containers had one bag of 400 g of giant *salvinia* dried matter. There was no significant difference of pH values between the treatments and control during the experiments.

Figure 4:
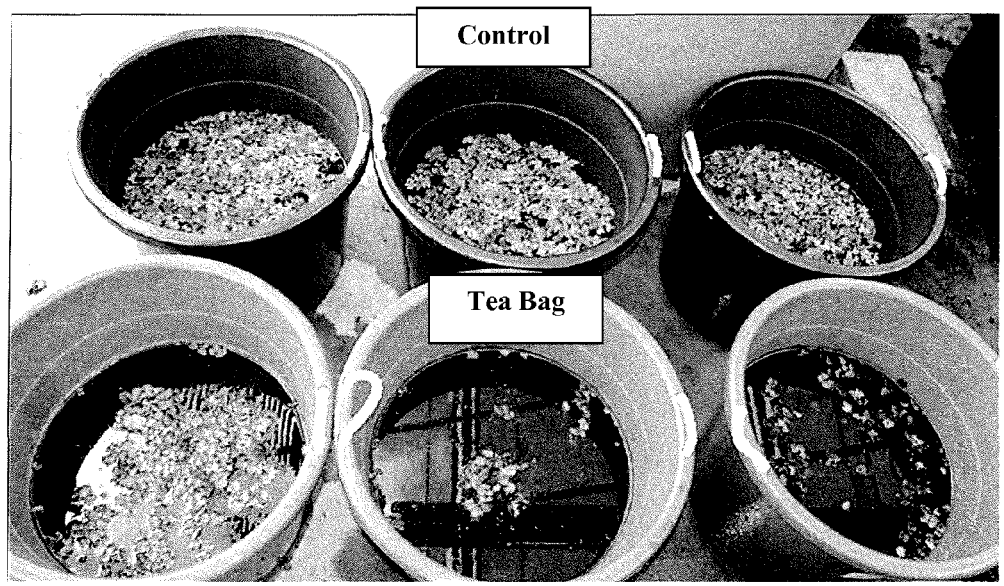
FIG. 4—The photograph shows that giant salvinia (Salvinia molesta) plants were totally eliminated by the dried plant matter of giant salvinia (a bag of 400 g plant matter was placed in the bottom of each of the containers on the bottom row) by the end of the second week of experiments in the greenhouse in comparison with controls (containers on the top row); there was no new growth within the six months of observation.

Results:

In the 400 g treatment group, more than 35% of plants were dead by the end of the first week and all plants were dead by the end of the second week and no plants survived or new growth occurred thereafter during the observation of six months (FIGS. 3 and 4). In this treatment, the root-like submerged leaves of giant *salvinia* were totally damaged about a week later and then the floating leaves turned into brown and dead (FIG. 5). In contrast to those in the normal plant growth condition, the trichomes on the upper surfaces of the floating leaves of giant *salvinia* were soon wilted following the response of submerged leaves to the "tea bag" treatment (FIG. 6). The wilted trichomes released autotoxic compounds and thus enhanced the endocidal function. It was also found that the 200 g treatment group inhibited almost 50% of the plants by the end of the fourth week of the experiment. However, no significant effect of the 100 g treatment was observed on *salvinia* growth.

Example 2

Elimination and Prohibition of Giant *Salvinia* Plants by Water Extract of the Dried Matter of Giant *Salvinia*

General Experimental Procedures:

Air-dried whole plants (350 g) were ground to a coarse powder and percolated with $H_2O$ at RT to yield a 4 L aqueous solution (0.84%, g/mL). Of the aqueous solution, 119 mL was diluted to 900 mL 0.1% and 1,000 mL 0.01% solution (g/mL) for the following experiment. The experiment included 45 healthy and untreated living plants of giant *salvinia* (in secondary growth stage, approximately 7 g in fresh weight each). The plants were cultured and tested in plastic containers (14×15 cm, 0.68 L) in the NCPC Lab at RT. Controls: 15 plants with five in each container (3 replications) were cultured with 300 mL of tap water; 0.01% water extract treatment: 15 plants with five in each container (3 replications) were sprayed with 300 mL 0.01% of the water extract of giant *salvinia* dissolved in tap water; and 0.1% water extract treatment: 15 plants with five in each container (3 replications) were sprayed with 300 mL 0.1% of the water extracts of giant *salvinia* dissolved in tap water. Plant growth and survival status were documented and photographed weekly after the treatments. By the end of the 13th week, new growth biomass of the plants in each treatment was measured. The biomass of new growth was a primary factor to measure the inhibition of each treatment on the target plant.

Figure 7:
FIG. 7—The photograph shows that all giant *salvinia* (*Salvinia molesta*) plants were eliminated within the 13 weeks after the treatment with water extract of the dried matter of giant *salvinia*. The plants in the top row served as control without any treatment, and each plant has developed significant new growth. The plants in the middle row were treated with 0.01% water extract of giant *salvinia*, and some plants have developed new growth. The plants in the bottom row were treated with 0.1% water extract of giant *salvinia*, and all plants are dead and no new growth was developed from any plants during the eight months of observation. The three columns represent three replications of the experiment.

Results:

By the end of 13 weeks of treatment, each of the 15 plants in the control group had new growth, and 12 of the total 15 plants treated with 0.01% water extract of giant *salvinia* had new growth (FIG. 7). All giant *salvinia* plants treated with 0.1% water extract of giant *salvinia* were dead and no new growth developed from any of the plants during the eight months of observation. pH values of the culture solution varied from 7.4 to 7.6 and there were no significant differences among control and treatments.

Example 3

Elimination and Prohibition of Giant *Salvinia* Plants by Fractions of Water Extract of the Dried Matter of Giant *Salvinia*

General Experimental Procedures:

Air-dried whole plants of giant *salvinia* (1.4 kg) were ground to a coarse powder and extracted two times for 48 h with $H_2O$ (12 L×2) at RT. The combined $H_2O$ extracts were concentrated to give extracts (88 g) under reduced pressure. The $H_2O$ extracts was applied on a column of silica gel (1,000 g) eluting with the mixture of $MeOH/CH_2Cl_2$ (1:1, v/v, 3 L), 3 L of 100% MeOH, and 1 L $H_2O$ to obtain three fractions, respectively (FIG. 1). The water extract and three fractions were all prepared as experimental solutions at the concentration of 0.1%. The total 45 healthy and untreated living plants of giant *salvinia* (in secondary growth stage, approximately 10 g in fresh weight each) were cultured and tested in the plastic containers (14×15 cm, 0.68 L) in the NCPC Lab at RT. The five treatments are as follows. Controls: 9 plants with three in each container (3 replications) were cultured with 150 mL of tap water; water extract treatment: 9 plants with three in each container (3 replications) were sprayed with 150 mL 0.1% of the water extract of giant *salvinia* dissolved in tap water; $H_2O$ fraction treatment: 9 plants with three in each container (3 replications) were sprayed with 150 mL 0.1% of $H_2O$ fraction dissolved in tap water; MeOH fraction treatment: 9 plants with three in each container (3 replications) were sprayed with 150 mL 0.1% of MeOH fraction dissolved in tap water; and $MeOH/CH_2Cl_2$ fraction treatment: 9 plants with three in each container (3 replications) were sprayed with 150 mL 0.1% of $MeOH/CH_2Cl_2$ (1:1) fraction dissolved in tap water. Plant growth and survival status were documented and photographed weekly after the treatments. By the end of 2nd week, new growth biomass of plants in each treatment was measured. The biomass of new growth was a primary factor to measure the inhibition of each treatment on the target plant.

Figure 8:
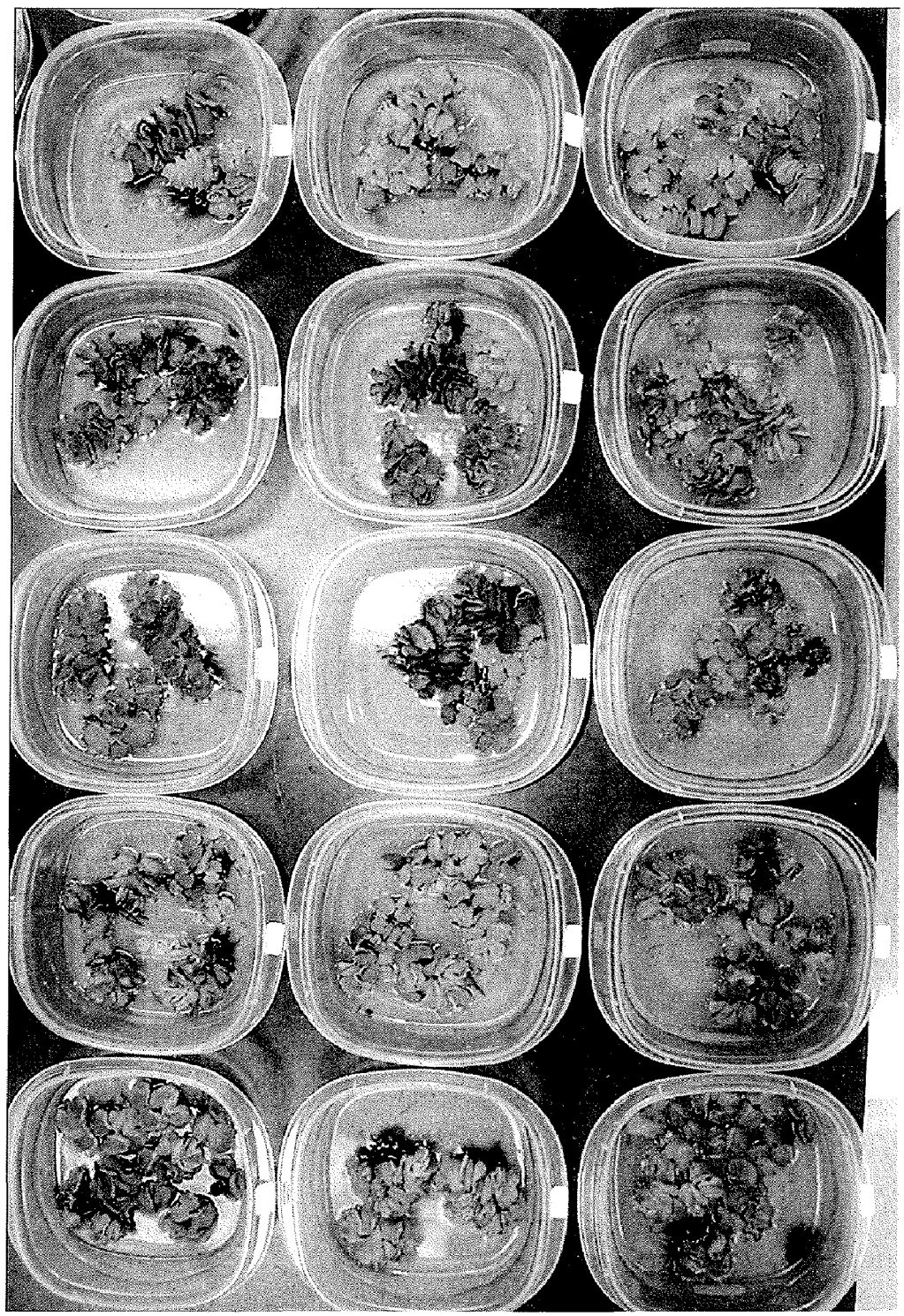
FIG. 8—The photograph showing growth performance of giant *salvinia* (*Salvinia molesta*) plants two weeks after the treatments of water extract of the dried matter of giant *salvinia* and its three fractions in comparison with those in the control group. Top row: plants cultured in water without any treatment (control); 2nd row: plants were treated with 0.1% MeOH fraction (all plants dead); 3rd row: plants were treated with 0.1% MeOH/$CH_2Cl_2$ (1:1) fraction; 4th row: plants were treated with 0.1% $H_2O$ fraction; and the bottom row: 0.1% water extract of giant *salvinia*. The three columns represent three replications of the experiment.

Results:

On the 3rd day after the treatment, all plants treated with $MeOH/CH_2Cl_2$ or MeOH fraction were dead in comparison to 100% survival of the plants in the control group. During the same day of observation, some leaves of the plants treated with water extract or $H_2O$ fraction started to turn into brown color. By the end of two weeks, all plants in the control group were still alive (FIG. 8). By then, in contrast, no plants survived or new growth in both $MeOH/CH_2Cl_2$ and MeOH treatments, almost all plants were dead with water extract, while the biomass of living plants under the $H_2O$ fraction treatment was less than 25% of the plants in the control group (FIG. 8). The experiment indicated that $MeOH/CH_2Cl_2$ and MeOH fractions were very active and can fully control giant *salvinia* more quickly than its parent water extract and thus the following isolation of bioactive compounds was focused on these two fractions.

Example 4

Elimination and Prohibition of Giant *Salvinia* by Salviniside II, an Isolate from Water Extract of the Dried Matter of Giant *Salvinia*

General Experimental Procedures:

Continuous fractionation was based on the combined $MeOH/CH_2Cl_2$ (1:1, v/v) and 100% MeOH fractions which showed potent activity to inhibit growth of giant *salvinia* in Example 3. The combined fractions were loaded on a pre-equilibrated open ODS column (60×600 mm). The ODS column was eluted successively with 30%, 55%, 75% and 100% MeOH to yield four fractions F1, F2, F3, and F4, respectively. F3 (75% MeOH elute) was concentrated and separated by a preparative HPLC ($MeOH/H_2O$, 35:65, 254 nm) to yield four compounds including active salviniside II and C3 and inactive C1 and C2 and active fraction F32 and inactive F31 (FIG. 1). NMR experiments were performed on a JEOL ECS-400 and a Bruker Avance 700 NMR instrument. NMR data were reported as δ (ppm) values and referenced to the solvent used. HRESIMS were acquired on an electrospray instrument (MDS Sciex Pulsar Qstar, Ontario, Canada). Octadecyl-functionalized silica gel, silica gel, Sephadex LH-20, and TLC plates were purchased from Aldrich Chemical Co. HPLC analysis was performed on a Hewlett Packard Series 1100 with a HP 1100 diode array detector using a Hypersil ODS column (150×4.6 mm, 5 μM, Supelco; flow rate, 1 mL/min; $MeOH/H_2O$ (v/v) linear gradient, 2:98-98:2 in 35 min). Preparative HPLC was performed with an Acuflow Series III pump connected with an Acutect 500 UV/VIS detector using an Econosil ODS column (250×22 mm, 10 μM, All tech). The total 27 healthy and untreated living plants of giant *salvinia* (in secondary growth stage, approximately 10 g in fresh weight each) were cultured and tested in plastic containers (14×15 cm, 0.68 L) in the NCPC Lab at RT. The five treatments were as follows. Controls: 9 plants with three in each container (3 replications) were cultured with 150 mL of tap water; 0.01% salviniside II treatment: 9 plants with three in each container (3 replications) were sprayed with 150 mL 0.01% of salviniside II dissolved in tap water; and 0.1% salviniside II treatment: 9 plants with three in each container (3 replications) were sprayed with 150 mL 0.1% of salviniside II dissolved in tap water. Plant growth and survival status were documented and photographed weekly after the treatments. By the end of two weeks, new growth biomass of plants in each treatment was measured. The biomass of new growth was a primary factor to measure the inhibition of each treatment on the target plant.

Figure 9:
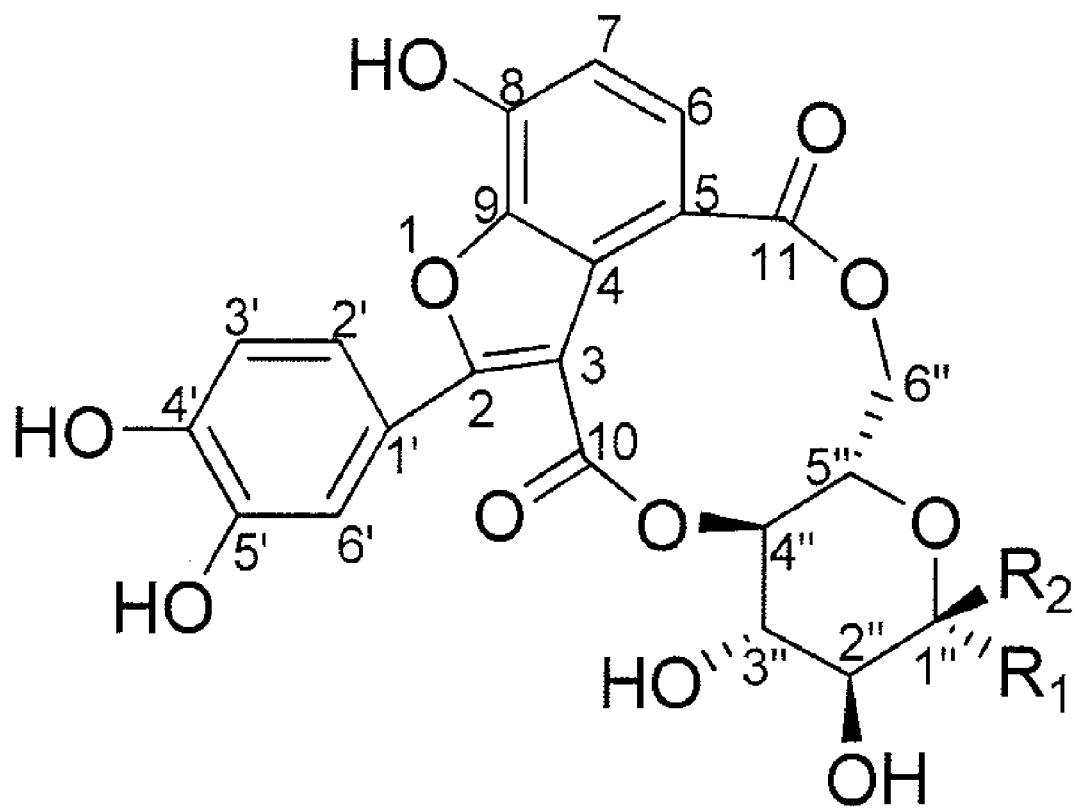
FIG. 9—Structure of bioactive salviniside II as endocide isolated from giant *salvinia* (*Salvinia molesta*).

Results:

The growth of giant *salvinia* was totally inhibited by salviniside II (FIGS. 9 and 10) at 0.1% of concentration within two weeks in the lab at RT (FIG. 11). There was no new growth identified thereafter during the eight months of observation.

Salviniside II is a new compound. It was obtained as colorless powders and showed an $[M-1]^+$ at m/z 473.0714 (calcd for 473.0720) in the HRESIMS, suggesting the molecular formula to be $C_{22}H_{18}O_{12}$. The $^{13}C$ and $^1H$-NMR spectrum (FIG. 10) displayed similarly two set of glycoside signals with two anomeric proton at δ 4.57 (1H, d, J=7.8 Hz, β-H-1") and δ 5.14 (1H, d, J=3.7 Hz, α-H-1"), and two protonated carbon at $δ_{C-β}$ 98.6 and $δ_{C-α}$ 94.4 observed in the HSQC spectrum. The analysis of the COSY, HSQC spectra of salviniside II indicated it is an isomeric mixture of α and β-D-glucopyranosides (Choudhary et al. 2008; Ding et al. 1999; Narasimhulua et al. 2010). In addition, each signals of the aglycon part appeared essentially in duplicate owing to the formation of a mixture of α and β-anomers in the NMR spectrum. Five aromatic protons were found in the $^1H$-NMR spectrum (FIG. 10), of which three signals at δ 7.39 (1H, dd, J=1.8 and 8.5 Hz, H-2'), δ 6.84 (1H, d, J=8.5 Hz, H-3'), and 7.45 (1H, d, J=1.8 Hz, H-6') were characteristic of a 1,2,4-trisubstituted phenyl moiety, the remaining two at δ 7.70 (1H, d, J=8.2 Hz, H-6) and 6.82 (1H, d, J=8.2 Hz, H-7) were assigned to a 1,2,3,4-tetra substituted phenyl group (Narasimhulua et al. 2010). A close inspection of the $^{13}C$-NMR spectrum data, together with the MS data, clearly revealed that the 1,2,3,4-tetrasubstituted phenyl moiety should be a part of a 8-carbon benzofuran skeleton (Maurya et al. 2004; Wu et al. 2011). The $^{13}C$ NMR spectra of salviniside II displayed two ester carbonyl carbons at δ 168.1 and δ 168.7. As observed in the HMBC spectrum, two key HMBC correlation among H-6 at $δ_H$ 7.70 and Glc H-6" at $δ_H$ 3.94 with a carbonyl carbon at $δ_C$ 168.1 (C-11)

established the linkage between the benzofuran unit and H-6" of Glc. Similarly, the other ester carbonyl carbon ($\delta_C$ 168.7, C-10) was attached to H-4" of Glc position by the HMBC spectrum analysis. These long-range HMBC correlations of H-2' to C-1', C-6' and C-2, and of H-6' to C-1', C-2' and C-2 established the connectivity of the benzofuran skeleton with 1,2,4-trisubstituted phenyl moiety. The 1,1-ADEQUATE spectrum also confirmed the assignment. The relatively downfield shifted of C-3 at $\delta$ 110.3 and the remaining one degree of unsaturation established the linkage of the C-3 and C-10. The complete assignment of the protons and carbons was achieved by a combination of $^1H$, $^{13}C$, HSQC, $^1H$-$^1H$ COSY, HMBC and 1,1-ADEQUATE spectral analyses. Thus, salviniside II was identified as 4",6"-O-[3, 5-dicarbonyl-8-hydroxy-2-(4',5'-dihydroxy-phenyl)-1-benzofuran-2-yl]-D-glucopyranose.

Example 5

Elimination and Prohibition of Giant *Salvinia* Plants by Water Extract and $H_2O$ Fraction of the Dried Matter of Giant *Salvinia* with Surfactants General Experimental Procedures:

Air-dried whole plants of giant *salvinia* (8 kg) were ground to a coarse powder and extracted in a vacuum distillation system (Eden Labs, Seattle, USA) with $H_2O$ two times for 24 h each (200 L and 150 L, respectively) at 60° C. The combined $H_2O$ extracts were concentrated to give an extract (703 g) under reduced pressure. The water extract was mixed with 300 g silica gel and loaded into a column of silica gel (1,000 g). The column was then eluted with 4 L of MeOH and 4 L $H_2O$. The water extract and $H_2O$ fraction were both prepared as experimental solutions at the concentration of 5%.

The HPLC chromatographs of the newly prepared water extract and $H_2O$ fraction were also established by Agilent 1100 HPLC system coupled to an Agilent 1100 diode array detector, and an Eclipse XDB-C18 column (4.6×150 mm, 3.5 µM) at a flow rate of 0.6 mL/min. A gradient elution was performed by using $H_2O$ (A) and $CH_3CN$ (B) as mobile phases. Elution was performed according to the following conditions: 2% B at time 0, linear increase to 98% B in 22 min, and hold 98% B for 8 min. The column temperature was maintained at 23° C. The HPLC chromatogram was standardized on retention times and peak intensities of the peaks observed at a wavelength of 254 nm. The concentration of water extract was 24 kg fresh plant matter/L and the injection volume was 3 µL for all analyses. The concentration of $H_2O$ fraction was 16 kg fresh plant matter/L. The injection volume was 50 µL for all analyses.

Part of each of water extract and $H_2O$ fraction was prepared separately as dry powder by SPD 2010 Integrated SpeedVac (Thermo Scientific, NC, USA) for 12 h and then was stored at RT for 26 weeks. In addition, both 5% water extract and 5% $H_2O$ fraction were stored at refrigerator (4° C.) for 26 weeks. To determine the stability of the water extract and $H_2O$ fraction during the storage, HPLC profiles of the powder and aqueous samples were established by Agilent 1100 at the condition described above.

The experiment included 18 containers and each container had 750 g (in fresh weight) of healthy living *Salvinia molesta* in all growth stages (primary, secondary, and tertiary stages) cultured in 57 L of rain water. The plants were cultured and tested in the glass tank in the lab at RT. There were six treatments. Controls: each of the three containers had 750 g giant *salvinia* plants cultured with rain water; "tea bag" treatment: each of the three containers with a nylon net bags of 800 g ground air-dried plant matter of giant *salvinia* on the bottom (see Example 1); water extract treatment: plants in each of the three containers were sprayed twice (on the $1^{st}$ and $18^{th}$ day), each time with 100 mL 5% of the water extract of giant *salvinia* dissolved in water; water extract with surfactants treatment: plants in each of the three containers were sprayed twice (on the $1^{st}$ and $18^{th}$ day), each time with 100 mL 5% of the water extract of giant *salvinia* dissolved in water with 0.5 mL Inlet™ (polyalkoxylated and non-alkoxylated aliphatics and derivatives 90%, Helena Chemical Company, Collierville, Tenn., USA) and 0.25 mL Kinetin® (proprietary blend of polyalkyleneoxide modified polydimethylsiloxane 99%, Helena Chemical Company, Collierville, Tenn., USA); $H_2O$ fraction treatment: plants in each of the three containers were sprayed twice (on the $1^{st}$ and $18^{th}$ day), each time with 100 mL 5% of $H_2O$ fraction of the water extract of giant *salvinia* dissolved in water; and $H_2O$ fraction with surfactants treatment: plants in each of the three containers were sprayed twice (on the $1^{st}$ and $18^{th}$ day), each time with 100 mL 5% of $H_2O$ fraction of the water extract of giant *salvinia* dissolved in water with 0.5 mL Inlet™ and 0.25 mL Kinetin®. Plant growth and survival status were documented and photographed weekly after the treatments. By the end of $3^{rd}$ or $4^{th}$ week, biomass of living plants in each treatment was measured.

Figure 12:
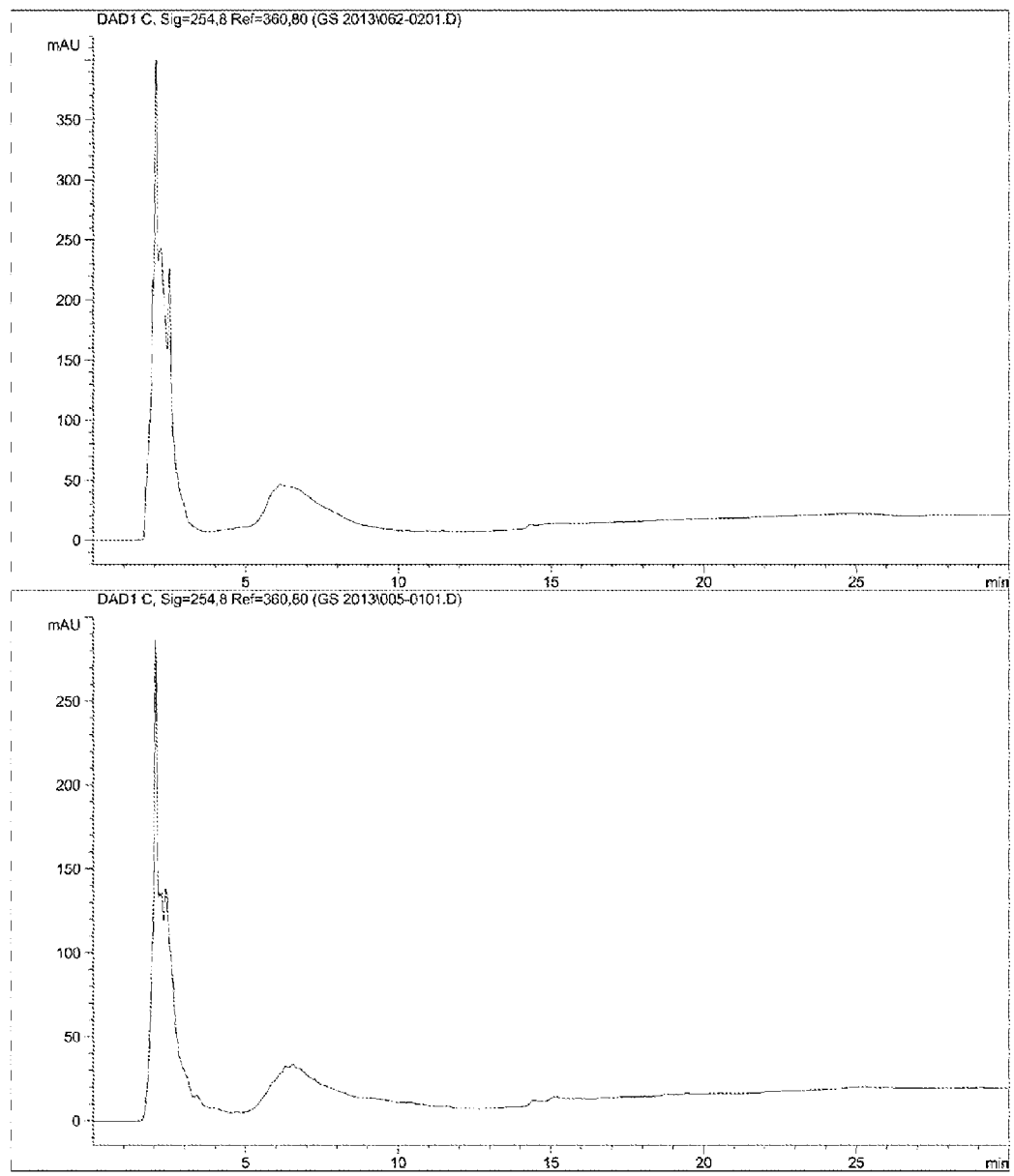
FIG. 12—HPLC profiles of water extract from the dried matter of giant *salvinia* (*Salvinia molesta*) on the preparation day (upper) and storage as the powder at RT for 26 weeks (bottom) using Agilent 1100 HPLC system (Eclipse XDB-C18 column (4.6×150 mm, 3.5 µM) at a flow rate of 0.6 mL/min, detection wavelength=254 nm, the extract concentration: 24 kg/L in fresh weight, and the injection volume: 3 µL). The stored powder had approximately 70% of the total peak area of that in the newly prepared extract.
Figure 13:
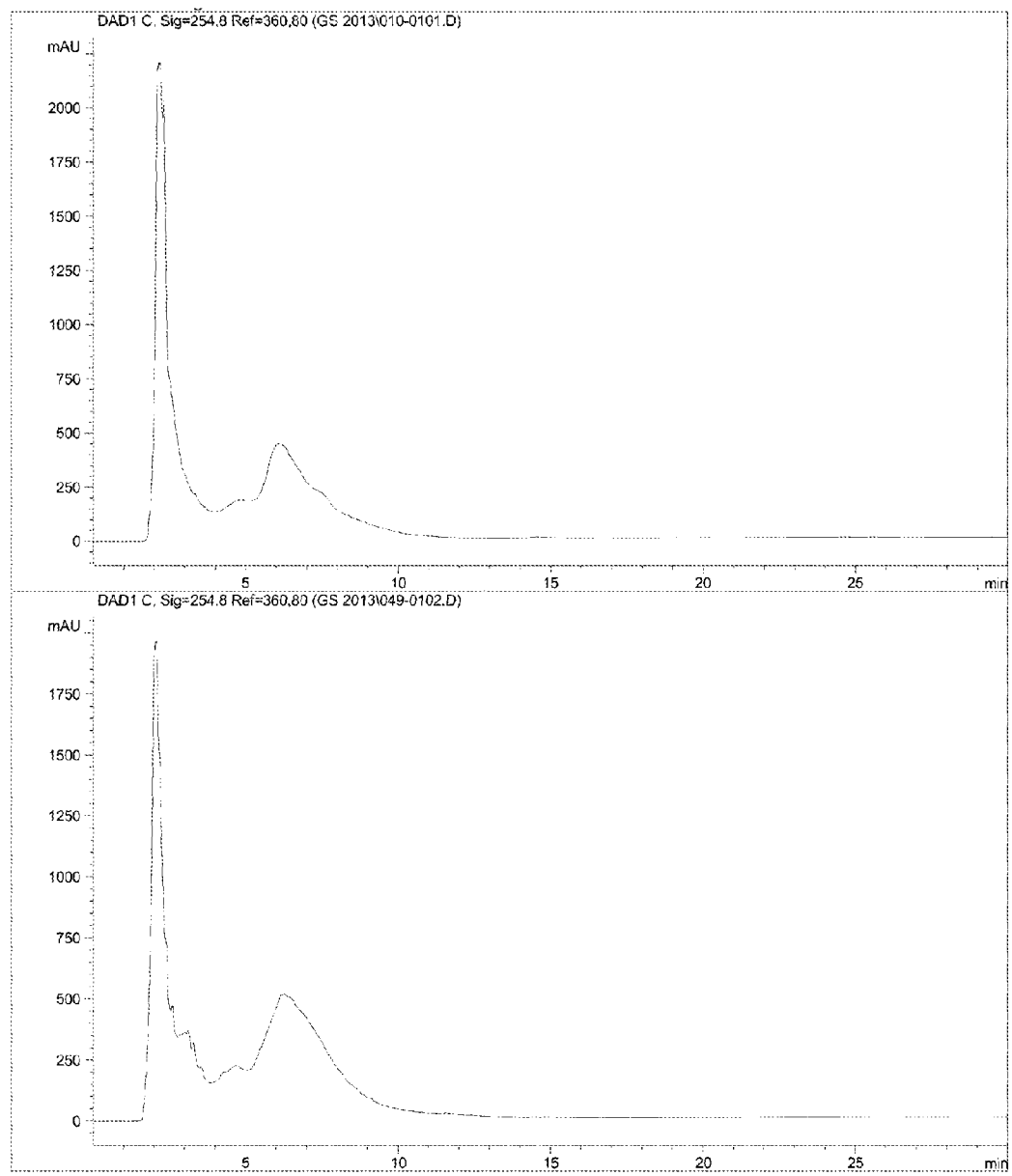
FIG. 13—HPLC profiles of 5% $H_2O$ fraction of water extract from the dried matter of giant *salvinia* (*Salvinia molesta*) on the preparation day (upper) and stored in refrigerator (4° C.) for 26 weeks (bottom) using Agilent 1100 HPLC system (Eclipse XDB-C18 column (4.6×150 mm, 3.5 µM) at a flow rate of 0.6 mL/min, detection wavelength=254 nm, the extract concentration: 16 kg/L in fresh weight, and the injection volume: 50 µL). The stored $H_2O$ fraction still had approximately 90% of the chemical contents of the newly prepared sample.

Results:

According to HPLC analyses, the powder samples stored at RT for 26 weeks were relatively stable. By the end of 26 weeks, the extract powder still had approximately 70% of the total peak area of that in the newly prepared extract (FIG. 12). By the end of 26 weeks, $H_2O$ fraction powder stored at RT preserved over 90% of its chemical contents and 5% $H_2O$ fraction liquid stored at refrigerator (4° C.) still had approximately 90% of the total peak area of the newly prepared sample (FIG. 13).

Figure 14:
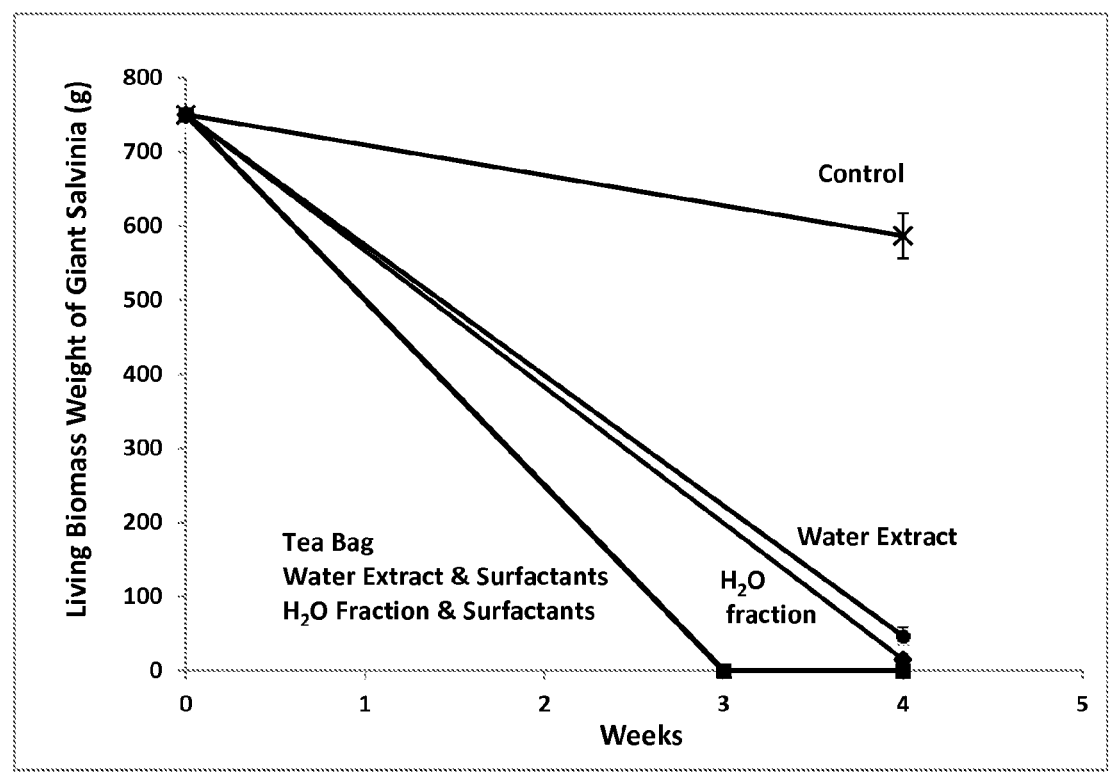
FIG. 14—The growth of giant *salvinia* (*Salvinia molesta*) can be successfully controlled by the endocide treatments with or without surfactants. By the end of the third week, all plants treated with either "tea bag" of the dried matter, water extract of the dried matter with surfactants, or $H_2O$ fraction of the water extract from the dried matter with surfactants were dead and there was no new growth during the following four months of observation. By the end of the $4^{th}$ week, over 90% or 95% of the plants treated with water extract and $H_2O$ fraction of the water extract were dead, respectively (with bars presenting standard deviations).
Figure 15:
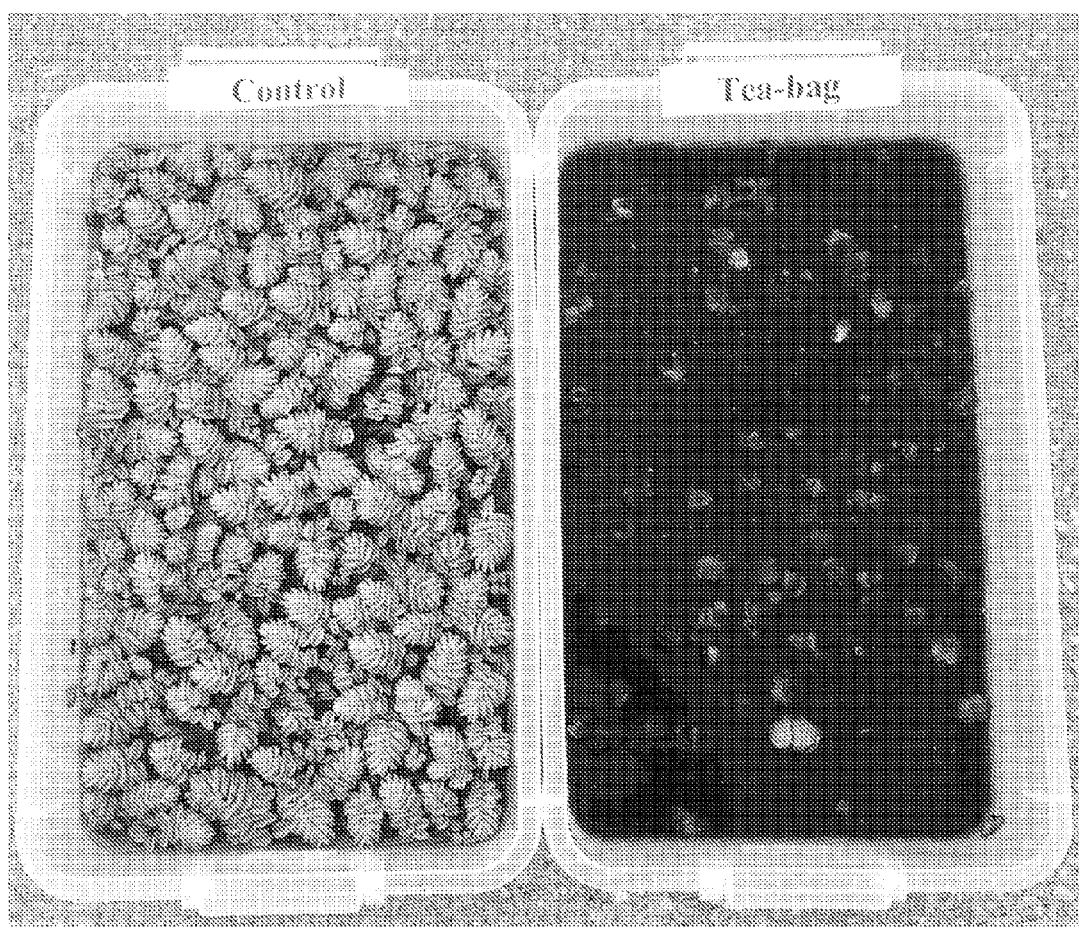
FIG. 15—The photograph shows that all giant *salvinia* (*Salvinia molesta*) plants were eliminated within three weeks after the treatment using a "tea bag" of the dried matter of giant *salvinia* (right) in comparison with control (left).

The growth of giant *salvinia* can be successfully controlled by the endocide treatments in comparison with control (FIG. 14). By the end of the third week, all plants treated with either "tea bag" (FIG. 15), water extract with surfactants, or $H_2O$ fraction of the water extract with surfactants were dead and there was no new growth during the following four months of observation. By the end of $4^{th}$ week, over 90% or 95% of the plants treated with water extract and $H_2O$ fraction of the water extract were dead, respectively. Obviously, Surfactants made the *salvinia* endocides more effective. Because the experiments were conducted in November and at RT, plants experienced relatively slow growth. The living biomass in the controls had lightly decreased because the mature tissues were dead and more young plants emerged during the four weeks of experiment.

Example 6

Elimination and Prohibition of Giant *Salvinia* Plants by Hydraulic Extract of the Fresh Matter of Giant *Salvinia*

General Experimental Procedures:

The total 58 kg fresh matter of giant *salvinia* plants were chopped and shredded by food processor. Then the processed material was pressed by hydraulic press (Enerpac) at pressure of 27,579 kPa (4,000 psi) for 2 min to get 30 kg extract juice. To obtain the concentration of the extract juice, three 30 mL of juice samples were randomly collected and measured. Each of the three juice samples was centrifuged by accuSpin 3R Benchtop centrifuge (Fisher Scientific, PA, USA) at 3,000 rpm for 10 min. The upper liquid was first dried by SPD 2010 Integrated SpeedVac (Thermo Scientific, NC, USA) for 12 h. Then dried extract was measured. The average result of the three test samples was used to estimate the concentration of the extract juice. The concentration of hydraulic extract juices were 2 kg fresh plant matter/L. The spray treatment experiment included three plastic containers (20 gal, approximately equal to 75.7 L) with approximately 390 g (in fresh weight) of giant *salvinia* living plants (in all growth stages: primary, secondary, and tertiary stages) in 50 L of tap water each in the greenhouse (30° C. during the day time and 20° C. at night). There were three treatments. Control: the plants in the first container were sprayed with 150 mL tap water only; extract juice treatment: the plants in the second container were sprayed with 150 mL of extract juice; and extract juice and surfactants treatment: the plants in the third container were sprayed with 150 mL extract juice with 0.375 mL Inlet™ (polyalkoxylated and non-alkoxylated aliphatics and derivatives 90%, Helena Chemical Company, Collierville, Tenn., USA) and 0.1875 mL Kinetin® (proprietary blend of polyalkyleneoxide modified polydimethylsiloxane 99%, Helena Chemical Company, Collierville, Tenn., USA). The second same spay treatment was applied to each of these six contains a week later, respectively. Plant growth and survival status were documented and photographed weekly after the treatments. By the end of 6th week, the total biomass of living plants in each treatment was measured. To investigate the survival rate of giant *salvinia* after hydraulic extraction, the 28 kg (in fresh weight) residual plant material of giant *salvinia* expressed by hydraulic press was cultured in five containers with 50 L tap water each for six weeks.

Figure 16:
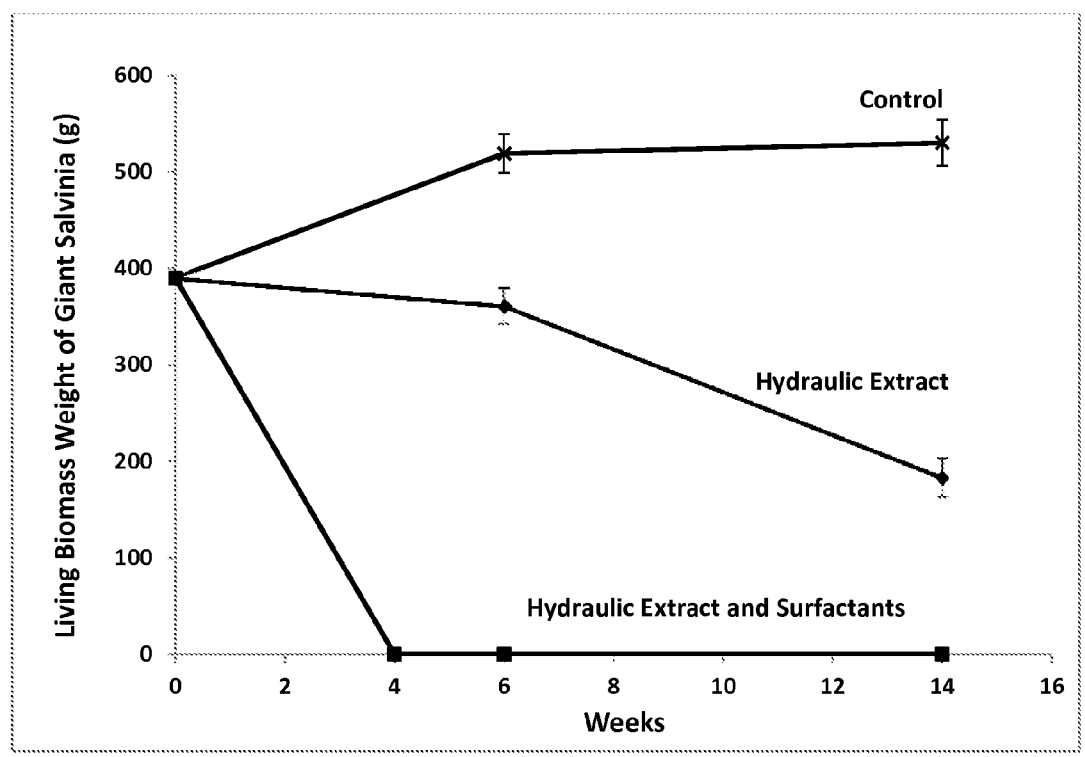
FIG. 16—The growth of giant *salvinia* (*Salvinia molesta*) can be successfully controlled by the extract juice from the fresh matter of giant *salvinia* by hydraulic press. After two treatments, the hydraulic extract juice with surfactants totally eliminated the giant *salvinia* within four weeks and there was no new growth thereafter (with bars presenting standard deviations).
Figure 17:
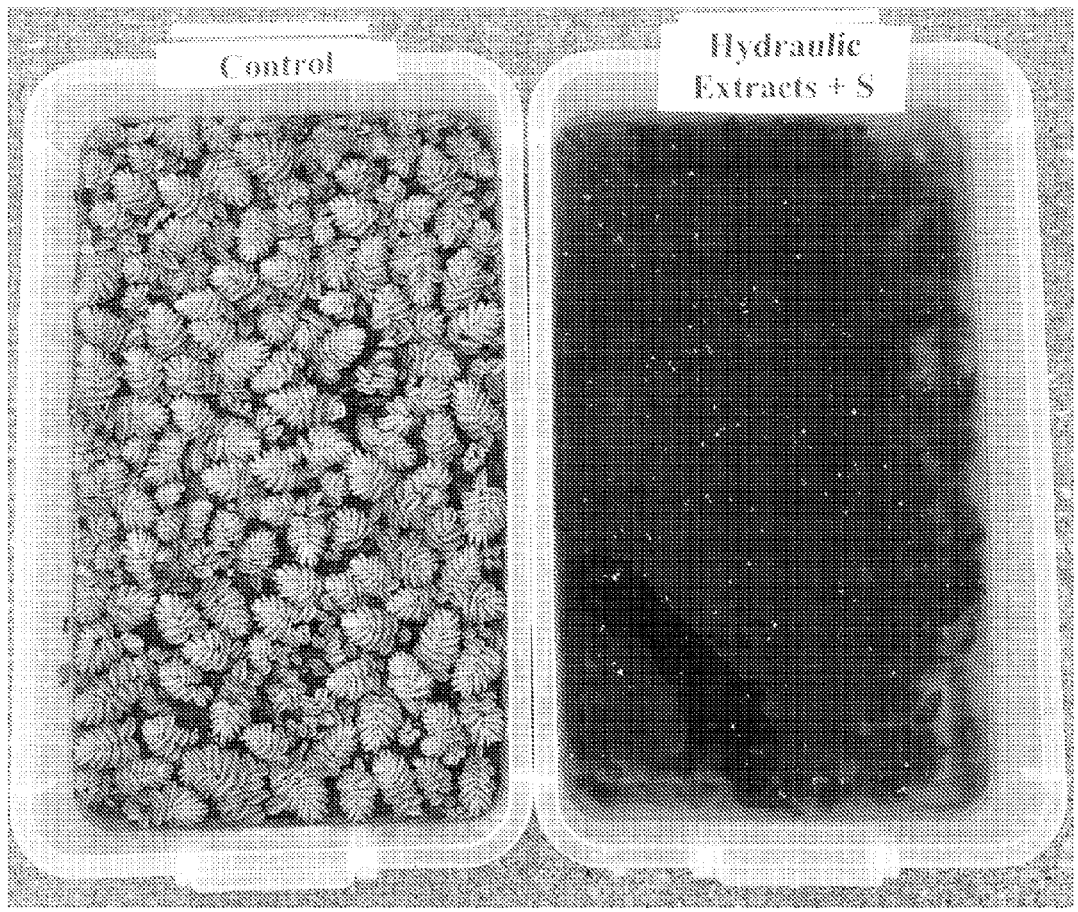
FIG. 17—The photograph shows that all giant *salvinia* (*Salvinia molesta*) plants were eliminated within four weeks after the treatment with hydraulic extract juice from the fresh matter of giant *salvinia* (right) in comparison with the control (left).
Figure 18:
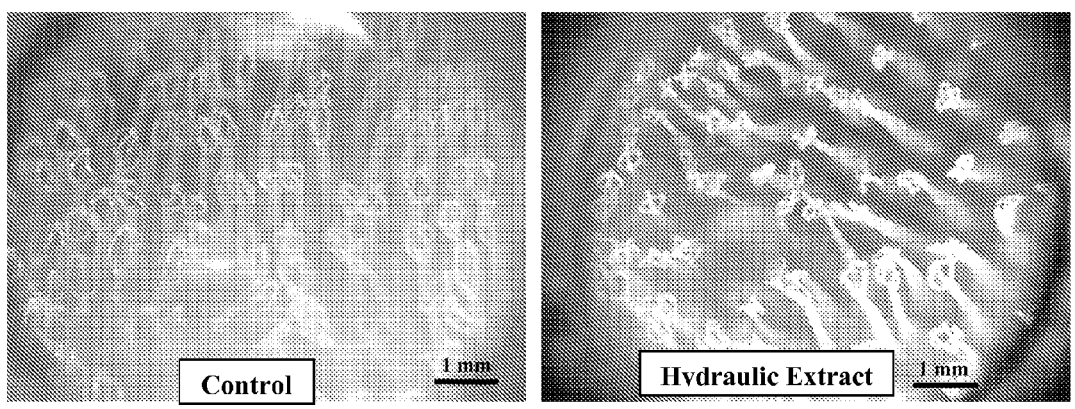
FIG. 18—The photograph shows that the trichomes on the upper surfaces of the floating leaves of giant *salvinia* (*Salvinia molesta*) were significantly damaged by the hydraulic extract (right) in comparison with those in the control (left). The wilted trichomes caused by the hydraulic extract released autotoxic chemicals and enhanced the endocidal function of the hydraulic extract.
Figure 19:
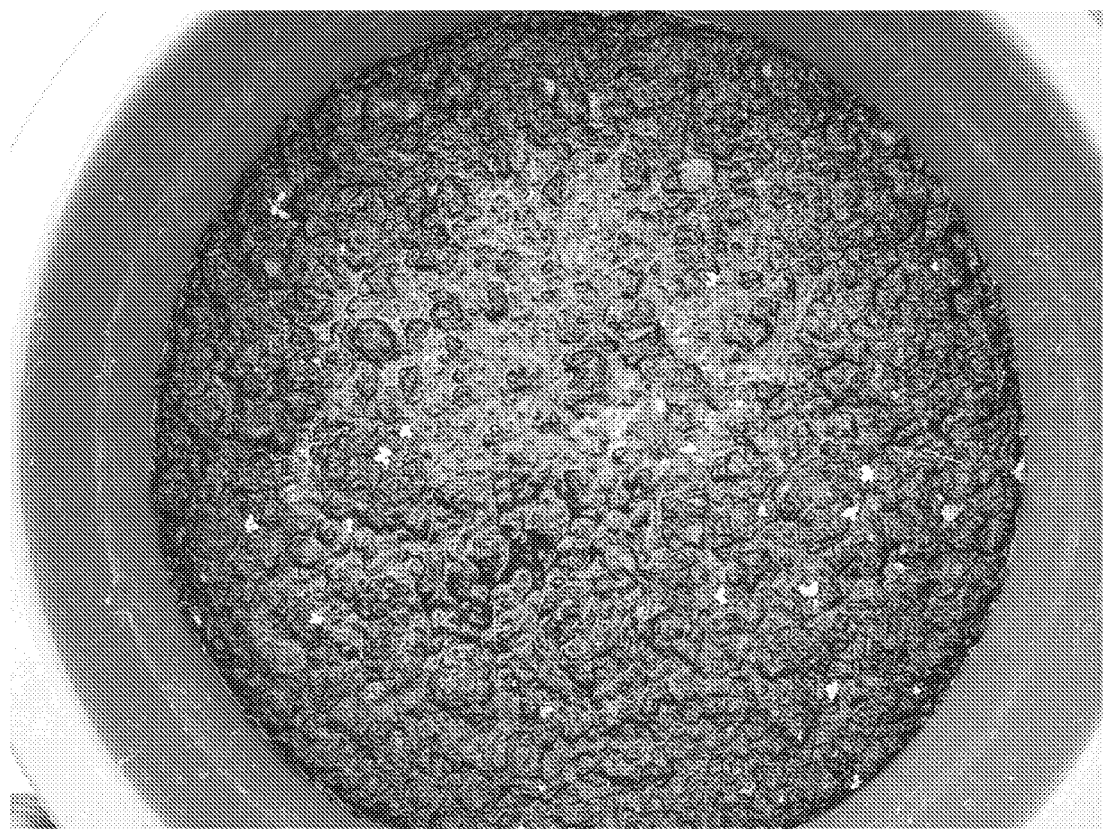
FIG. 19—The photograph shows that there was no plant survival or new growth in the cultured residues from the juice production from fresh plant matter of giant *salvinia* (*Salvinia molesta*) within six weeks (white dots are living least duckweed (*Lemna minuta*)).

Results:

The extraction rate of hydraulic extract from the fresh matter of giant *salvinia* in this experiment was approximately 51.7%. Based on the three test samples, the estimated concentration of the experimental extract juice was 0.28% (in fresh weight). The spray experiment showed that the hydraulic extract juice effectively inhibited the giant *salvinia* after two treatments (FIGS. 16 and 17). In comparison with those in the control treatment, the trichomes on the upper surfaces of the floating leaves of giant *salvinia* treated by the hydraulic extract had significant damage (FIG. 18). The wilted trichomes released autotoxic chemicals to enhance the endocidal function of the hydraulic extract. With surfactants, hydraulic extract juice totally eliminated the giant *salvinia* within four weeks and no new growth thereafter. The experiment indicates that the juice expressed from fresh matter of giant *salvinia* (e.g., by hydraulic press) is effective enough and can be directly used in control of giant *salvinia* without concentrating process. All plant tissues of giant *salvinia* after hydraulic extraction were dead and there was no new plant growth in the cultured plant residues from the hydraulic extraction within six weeks of observation (FIG. 19).

Example 7

Elimination and Prohibition of Giant *Salvinia* Plants by Water Extract from the Dried Matter and Hydraulic Extract of the Fresh Matter of Giant *Salvinia* with Surfactants General Experimental Procedures:

The 5% water extract from the dried matter of giant *salvinia* (called "water extract") was prepared as described in the Example 5. The total 80 kg fresh matter of giant *salvinia* plants were chopped and shredded by chipper shredder CS 3310 (Cub Cadet, Cleveland, Ohio, USA). Then the processed material was pressed by hydraulic press (Enerpac) at pressure of 27,579 kPa (4,000 psi) for 2 min to get 38 kg extract juice. To obtain the concentration of the hydraulic extract, three 30 mL of juice samples were randomly collected and measured. Each of the three juice samples was centrifuged by accuSpin 3R Benchtop centrifuge (Fisher Scientific, PA, USA) at 3,000 rpm for 10 min. The upper liquid was first dried by SPD 2010 Integrated SpeedVac (Thermo Scientific, NC, USA) for 12 h. Then dried extract was measured. The average result of the three test samples was used to estimate the concentration of the hydraulic extract (called "hydraulic extract"). The HPLC profiles of both water extract and hydraulic extract were established before the first treatments by using both of the following methods. (1) Method A: Agilent 1100 HPLC system coupled to an Agilent 1100 diode array detector, and an Eclipse XDB-C18 column (4.6×150 mm, 3.5 µM) at a flow rate of 0.6 mL/min. A gradient elution was performed by using $H_2O$ (A) and $CH_3CN$ (B) as mobile phases. Elution was performed according to the following conditions: 2% B at time 0, linear increase to 98% B in 22 min, and hold 98% B for 8 min. The column temperature was maintained at 23° C. The HPLC chromatogram was standardized on retention times and peak intensities of the peaks observed at a wavelength of 254 nm. The concentration of both water extract and hydraulic extract were 2 kg fresh plant matter/L. The injection volume was 50 µL for all analyses. (2) Method B: Agilent 1260 HPLC system coupled to an Agilent 1260 diode array detector, and an Acclaim HILIC-10 column (4.6×150 mm, 3.0 µM) at a flow rate of 0.6 mL/min. The mobile phase was $CH_3CN/H_2O$ (65:35, v/v). The column temperature was maintained at 23° C. The HPLC chromatogram was standardized on retention times and peak intensities of the peaks observed at a wavelength of 230 nm. The concentration of both water extract and hydraulic extract were 40 kg fresh plant matter/L. The injection volume was 20 µL for all analyses. To determine the stability of hydraulic extract, HPLC profiles of the hydraulic extracts stored at refrigerator (4° C.) and RT was established separately by above Method A daily for the first week and on the $14^{th}$ week before the third treatment in comparison with the profiles of the newly prepared extract for the first treatments. The spray treatment experiment included six 625 gal (approximately 2,366 L) containers with approximately 7,400 g (including approximately 7,000 g of plants in tertiary growth stage, approximately 300 g of plants in secondary growth stage, and approximately 100 g of plants in primary growth stage) of giant *salvinia* living plant in 1,700 L of rain water each in the greenhouse (30° C.). There were three treatments. Control: the plants in each of the two containers were sprayed with 2.5 L rain water only; water extract with surfactants treatment: the plants in each of the two containers were sprayed with 2.5 L of 5% water extract with 6.25 mL Dyne-Arnie® (methyl easters of C16-C18 fatty acids, polyalkyleneoxide moditfed poly dimthylsiloxane, alkylphenol ethoxylate 99%, Helena Chemical Company), and 3.125 mL Kinetin® (proprietary blend of polyalkyleneoxide modified polydimethylsiloxane 99%, Helena Chemical Company, Collierville, Tenn., USA); and hydraulic extract and surfactants treatment: the plants in each of two containers were sprayed with 2.5 L extract juice with 6.25 mL Dyne-Amic®, and 3.125 mL Kinetin®. The second spay treatment at the same dosage was applied to each of these six contains 10 days later, respectively. Plant growth and survival status were documented and photographed weekly after the treatments. By the end of 14th week, the total biomass of living plants in each treatment was measured. Then the third spay treatment at the dosage of 0.5 L (for water extract and extract juice, each with 1.25 mL Dyne-Amic®, and 0.625 mL Kinetin® was applied to each of these six contains, respectively. To investigate the survival rate of giant *salvinia* after hydraulic extraction, the 42 kg (in fresh weight) residual plant material of giant *salvinia* expressed by hydraulic press was cultured in six containers with 50 L tap water each for six weeks.

Figure 20:
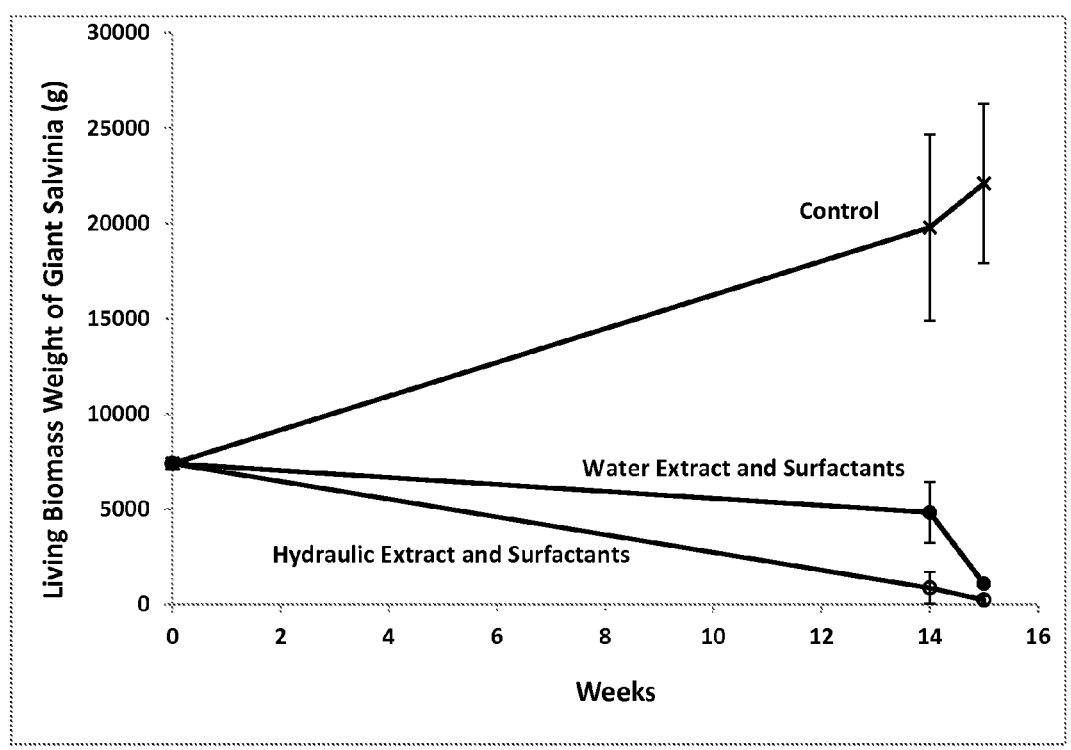
FIG. 20—The diagram shows that both water extract from the dried matter and hydraulic extract from the fresh matter of giant *salvinia* with surfactants effectively inhibited the giant *salvinia* after two treatments (with bars presenting standard deviations).

Results:

The extraction rate of hydraulic extract from the fresh matter of giant *salvinia* in this experiment was approximately was 47.5%. Based on the three test samples in each experiment, the estimated concentration of the experimental hydraulic extract was 0.40% (in fresh weight). The hydraulic extract in this experiment had lower extraction rate of yield at higher concentration than that in the Example 6 because the plant matter used in this extraction had more dead tissues which holding less moisture. This experiment showed that both water extract and hydraulic extract with surfactants effectively inhibited the giant *salvinia* after two treatments (FIG. 20). The hydraulic extract with surfactants totally eliminated the giant *salvinia* within 15 weeks. The experiment indicates that hydraulic extract expressed from the fresh matter of giant *salvinia* was effective enough without concentrating process and can be used directly in inhibition of the species (FIG. 20). All plant tissues of giant *salvinia* after hydraulic extraction were dead and there was no new plant growth in the cultured plant residues from the hydraulic extraction within six weeks of observation.

Figure 21:
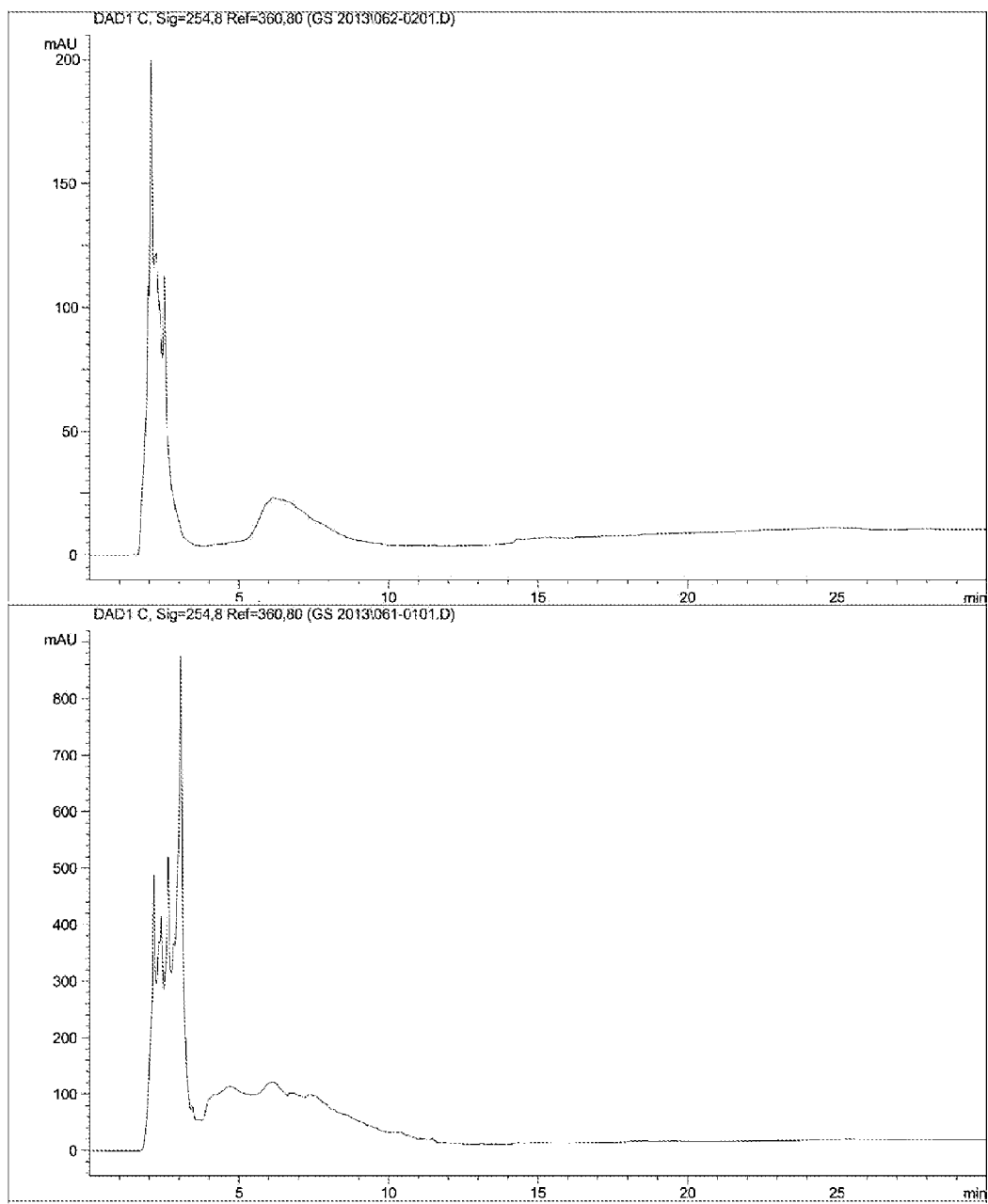
FIG. 21—HPLC profiles of water extract from the dried matter of giant *salvinia* (*Salvinia molesta*) (upper) and hydraulic extract from fresh matter of giant *salvinia* (bottom) by using an Agilent 1100 HPLC system coupled to an Agilent 1100 diode array detector, and an Eclipse XDB-C18 column (4.6×150 mm, 3.5 µM) at a flow rate of 0.6 mL/min. A gradient elution was performed by using $H_2O$ (A) and $CH_3CN$ (B) as mobile phases. Elution was performed according to the following conditions: 2% B at time 0, linear increase to 98% B in 22 min, and hold 98% B for 8 min. The column temperature was maintained at 23° C. The HPLC chromatogram was standardized on retention times and peak intensities of the peaks observed at a wavelength of 254 nm. The concentration of both water extracts and hydraulic extract were 2 kg fresh plant matter/L. The injection volume was 50 µL for all analyses.
Figure 22:
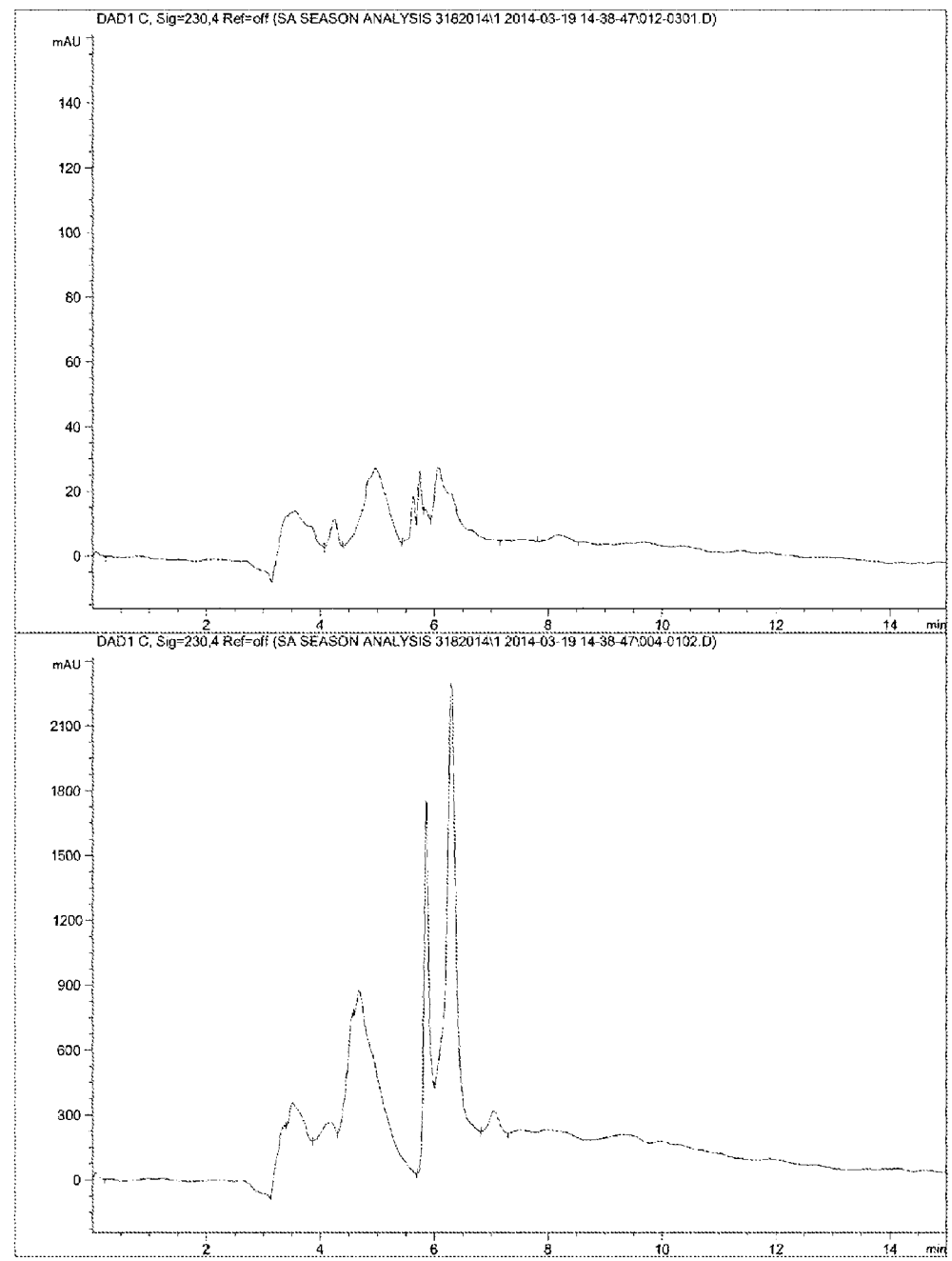
FIG. 22—HPLC profiles of water extract from the dried matter of giant *salvinia* (*Salvinia molesta*) (upper) and hydraulic extract from the fresh matter of giant *salvinia* (bottom) by using Agilent 1260 HPLC system coupled to an Agilent 1260 diode array detector, and an Acclaim HILIC-10 column (4.6×150 mm, 3.0 µM) at a flow rate of 0.6 mL/min. The mobile phase was $CH_3CN/H_2O$ (65:35, v/v). The column temperature was maintained at 23° C. The HPLC chromatogram was standardized on retention times and peak intensities of the peaks observed at a wavelength of 230 nm. The concentration of both water extracts and hydraulic extract were 40 kg fresh plant matter/L. The injection volume was 20 µL for all analyses.

The experiment indicates that hydraulic extract expressed from the fresh matter of giant *salvinia* at low concentration (0.40%) was more effective than the concentrated water extract (5%) from the dried matter of giant salvina in inhibition of giant *salvinia*. HPLC profiles indicate that hydraulic extracts had more complex chemical constituents in both detection conditions and higher contents of some compounds and even unique compounds may be responsible for the strong bioactivity of the hydraulic extract (FIGS. 21 and 22).

Figure 23:
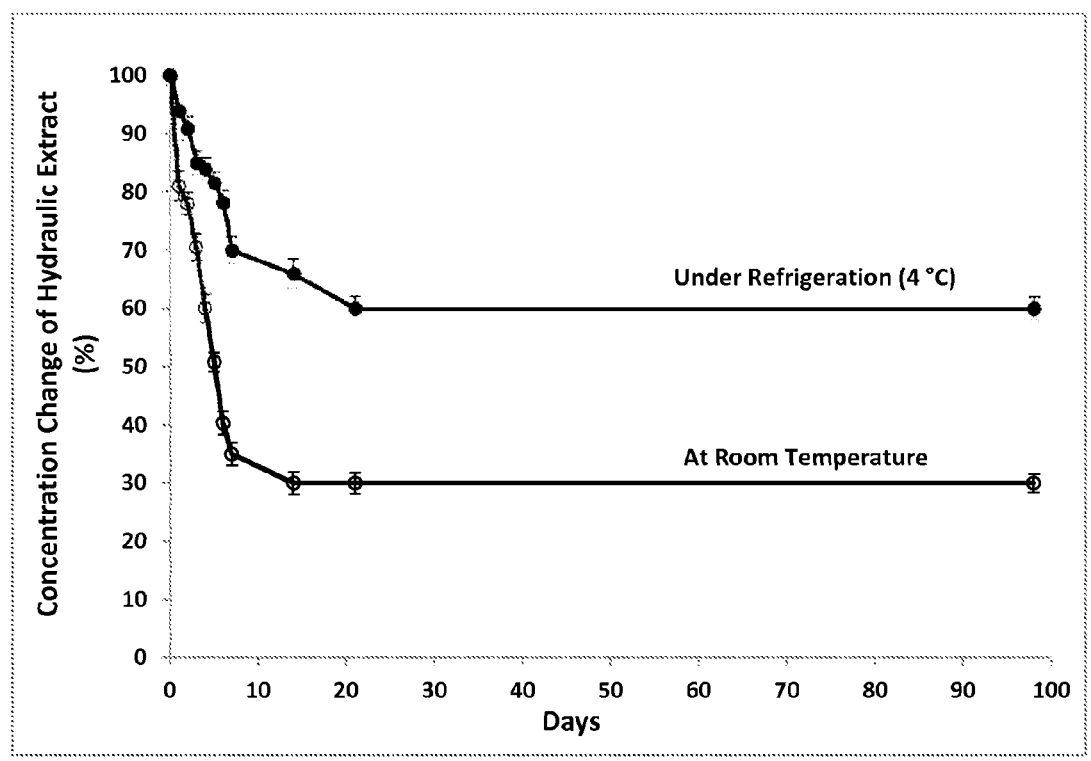
FIG. 23—The diagram shows that the hydraulic extracts are more stable when stored under refrigeration (4° C.) than that at RT. The total peak area of hydraulic extract stored at refrigeration (4° C.) for one, two, and 14 weeks contained 70%, 66%, and 60% of the total chemical contents in the newly prepared extract, respectively (with bars presenting standard deviations).
Figure 24:
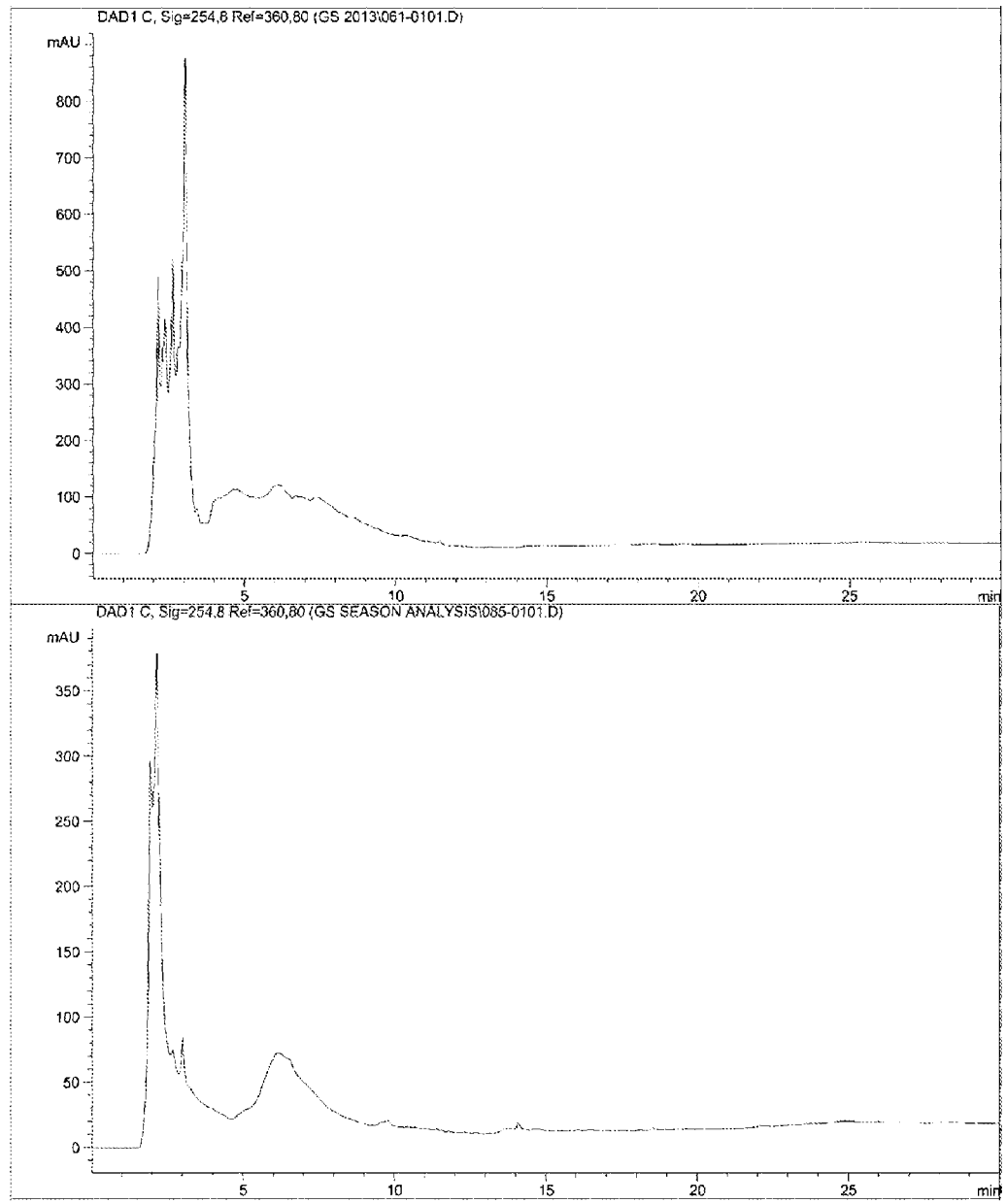
FIG. 24—HPLC profiles of hydraulic extract from the fresh matter of giant salvinia (*Salvinia molesta*) on the preparation day (upper) and stored at refrigerator (4° C.) for 14 weeks (bottom) by using Agilent 1100 HPLC system (Eclipse XDB-C18 column (4.6×150 mm, 3.5 µM) at a flow rate of 0.6 mL/min, detection wavelength=254 nm, the extract concentration: 2 kg/L in fresh weight, and the injection volume: 50 µL).

According to HPLC analyses, hydraulic extract degraded much more quickly at RT than that at refrigerator (4° C.). The total peak area of hydraulic extract stored at RT decreased to 35% by the end of the first week and to 30% by the end of the second week (vs. 70% and 66% stored at refrigerator (4° C.), respectively) in comparison with the newly prepared extract (FIG. 23). On the 14th week, hydraulic extract stored at refrigerator (4° C.) still contained approximately 60% of the total peak area of that in the newly prepared extract (first treatment) and still was active in inhibition of giant *salvinia* during the third spray treatment (FIG. 24).

Example 8

Elimination and Prohibition of Giant *Salvinia* Plants by Hydraulic Extract of the Fresh Matter of Giant *Salvinia* in Combination with Formic Acid or Acetic Acid General Experimental Procedures:

Formic acid (90.4%, certified ACS reagent grade, Fisher Scientific Company, Fair Lawn, N.J., USA) and acetic acid (99.7, ACS reagent grade, VWR International LLC, West Chester, Pa., USA) were prepared as solutions at the concentration of 0.01%, 0.1%, 1%, 5%, and 10% immediately before the bioassay experiments. The experimental hydraulic extract used in this example was prepared from the previous experiment (fresh matter of giant *salvinia* (method see Example 7). The actual concentration of the extract during this experiment was approximately 0.28%. There were 37 treatments in this experiment. Each treatment included 9 living healthy plants of giant *salvinia* in three Rubbermaid plastic containers (14×15 cm, 0.68 L) (each container had two plants in secondary stage and one in tertiary growth stage, in total of 6 g in fresh weight). The plants in each container were sprayed with 12.5 mL of tap water, formic acid, acetic acid, or combination of hydraulic extract with formic or acetic acid. Control: the plants was sprayed with water only; nine formic acid treatments (0.01%, 0.05%, 0.1%, 0.25%, 0.5%, 0.75%, 1%, 5%, and 10% concentrations); nine acetic acid treatments (0.01%, 0.05%, 0.1%, 0.25%, 0.5%, 0.75%, 1%, 5%, and 10% concentrations); nine hydraulic extract treatments with various concentrations of formic acid (0.01%, 0.05%, 0.1%, 0.25%, 0.5%, 0.75%, 1%, 5%, and 10%); and nine hydraulic extract treatments with various concentrations of acetic acid (0.01%, 0.05%, 0.1%, 0.25%, 0.5%, 0.75%, 1%, 5%, and 10%). Plant growth and survival status were documented and photographed hourly for the first 5 h and then daily for seven days after the treatment.

Results:

Giant *salvinia* is very sensitive to both formic acid and acetic acid. All plants treated with either formic or acetic acid at the 1% or higher concentrations were dead within 3 h of the treatment. However, at lower concentrations (<1%), formic acid was much more effective than acetic acid in control of giant *salvinia*. For example, 0.05% formic acid was more effective than 0.25% acetic acid in giant *salvinia*. Formic acid at the 0.01% concentration still effectively inhibited the growth of giant *salvinia*. By combing hydraulic extract with 0.25% formic acid, all giant *salvinia* plants were killed within 24 h. Treated by combing hydraulic extract with 0.05% formic acid, all giant *salvinia* plants were dead within a week. Treated by combing hydraulic extract with 0.01% formic acid, more than 40% of the giant *salvinia* plants were dead during the first week. The *salvinia* plants responded to the hydraulic extract with the organic acids much quickly and severely than hydraulic extract, formic acid, or acetic acid alone.

Example 9

Metal Analysis of the Dried Matter of Giant *Salvinia* and its Water Extract and Extract Salts General Experimental Procedures:

The dried matter of giant *salvinia* and its water extract used this experiment were from Example 3. From the MeOH fraction of the 88 g water extract of the dried matter of giant *salvinia* (see Example 3), 5 g salts were precipitated. 0.5 g of each of the ground dried plant matter of giant *salvinia*, water extract powder, and the salts was pre-digested overnight with 5 mL nitric acid in Digi-tubes at RT. Then the Digi-tubes were incubated on DigiPREP HT High Temperature Digestion Systems (SCP SCIENCE) for 3 h at 100° C. Cool down and add 4 mL of hydrogen peroxide. Cook for 90 min at 95° C. The solution was diluted to a final volume of 50 mL for ICP analysis (Thermo Scientific iCap 7200 ICP-OES). The 5 ppt (0.5% in dry weight) and 50 ppt (5% in dry weight) solutions of the salts were prepared. 70 g living healthy plants of giant *salvinia* in tertiary growth stage were cultured in each of nine plastic containers (23×23 cm, 2.4 L). There were three treatments with three containers each. Control: the plants in each of three containers were sprayed with 12.5 mL tap water only; 5 ppt salts treatment: the plants in each of the three containers were sprayed with 12.5 mL 0.5% salt solutions; 50 ppt salts treatment: the plants in each of the three containers were sprayed with 12.5 mL 5% salt solutions. Plant growth and survival status were documented and photographed weekly for eight weeks after the treatment.

Results:

The ICP analysis showed that the concentrations of the main meals cadmium (Cd), chromsium (Cr), cobalt (Co), copper (Cu), iron (Fe), lead (Pb), molybdenum (Mo), and zinc (Zn), in the dry extract powder were 0.16047, 0.883666, not detected, 5.310525, 228.0387, 2.515505, 0.039819, and 166.7952 ppm (in dry weight) (FIG. 25). The salts precipitated from the water extract of the dried matter of giant salvinia were mainly sodium (Na), potassium (K), cacium (Ca), and manganesium (Mg) salts according to the ICP analysis (FIG. 25). The 5 g precipitated salts accounts for 0.3333% of the 1.5 kg dry plant matter or 6.25% of the 88 g water extract in dry weight. Through eight weeks of observation, the plants treated with the salts at either 5 or 50 ppt did not have any significant damage. There was no significant biomass difference among the salts treatments and control. Obviously, the spray of the salts even at 5% did not inhibit the plant growth of giant alvinia. In contrast, water extract of the dry plant of giant salvinia can effectively control giant salvina as described in Examples 5 and 6. Thus, the salts were not the active ingredients of the water extract in responsible for inhibiting giant salvinia.

Example 10

Elimination and Prohibition of Floating Fern (Salvinia Minima) Plants by Water Extract of the Dried Matter of Giant Salvinia General Experimental Procedures:

The experiment included nine plastic containers (14×15 cm, 0.68 L) and each container had 10 g (in fresh weight) of healthy living Salvinia minima cultured in tap water in the greenhouse (30° C. during the day time and 20° C. at night). There were three treatments. Controls: the floating fern plants in each of three containers were sprayed three times with the total of 90 mL tap water; 0.1% water extract treatment: the plants in each of three containers were sprayed three times with the total 90 mL 0.1% of water extract of giant salvinia (the preparation method see Example 2); and 0.5% water extract treatment: the plants in each of three containers were sprayed three times with the total 90 mL 0.5% of water extract of giant salvinia (the preparation method see Example 2). Plant growth and survival status were documented and photographed weekly after the treatments. By the end of 1st, 2nd, 6th weeks, biomass of living plants in each container of all treatments was measured.

Figure 26:
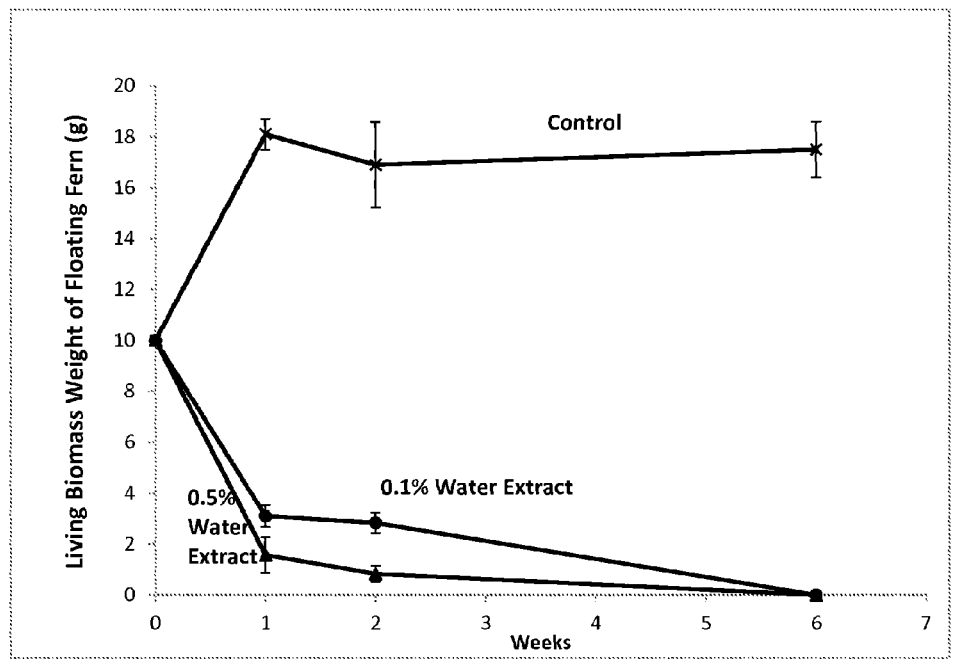
FIG. 26—The diagram shows that the growth of the floating fern (*Salvinia minima*) plants can be totally controlled by the water extract of dried matter of giant salvinia (*Salvinia molesta*) within six weeks (with bars presenting standard deviations).

Results:

The growth of the floating fern plants treated with either 0.1% or 0.5% water extract of giant salvinia were obviously inhibited during the first week (FIG. 26). By the end of the 6th week, all plants treated by water extract of giant salvinia were dead and there was no new growth thereafter.

Example 11

Elimination and Prohibition of Carolina Mosequito Fern (Azolla caroliniana) Plants by Water Extract from the Dried Matter and Hydraulic Extract of the Fresh Matter of Giant Salvinia General Experimental Procedures:

The experimental species included a fern species Carolina mosequito fern (Azolla caroliniana) (family Azollaceae). The experiments were conducted in the greenhouse (30° C. during the day time and 20° C. at night). Water extracts were prepared from the dried matter of giant salvinia (the preparation method see Example 2) and the hydraulic extract was prepared from the fresh matter of giant salvinia (see Example 7). The spray experiment started until the plants fully covered each of the 18 plastic containers (14×15 cm, 0.68 L) with 400 mL tap water each. The plants were randomly classified into six groups: Control: each of the three containers was spayed three times with 10 mL of tap water each time; 0.4% hydraulic extract treatment: each of the three containers was spayed with 10 mL of 0.4% hydraulic extract; 0.1% water extract treatment: each of the three containers was spayed twice with 10 mL of 0.1% water extract; 2.5% water extract treatment: each of the three containers was spayed twice with 10 mL of 2.5% water extract; 5% water extract treatment: each of the three containers was spayed twice with 10 mL of 5% water extract; and 7.5% water extract treatment: each of the three containers was spayed twice with 10 mL of 7.5% water extract. By the end of the $5^{th}$, $10^{th}$, and $15^{th}$ day, surface coverage of living plants in each container of all treatments was photographed and measured and $EC_{50}$ (half maximal effective concentration) values were calculated by the PROBIT procedure of SPSS 13.0 for Windows.

Results:

Neither the hydraulic extract (0.4%) nor the water extract at 0.1% concentration showed any significant impacts on the plant growth of Carolina mosquito fern during the first five days of the experiment but both extracts significantly inhibited the plant growth thereafter. The hydraulic extract was able to kill 100% of the Carolina mosquito fern by the end of the 15th day (FIG. 27). The water extract at higher concentrations (2.5, 5, or 7.5%) significantly inhibited the growth of Carolina mosquito fern soon after the treatments. Both 2.5% and 5% water extracts killed 100% of the Carolina mosquito fern plants by the end of the experiment. The 7.5% water extract eliminated all treated plants within the five days of the experiment (FIG. 27). EC50 value of water extracts of the dried matter of giant salvinia against Carolina mosquito fern is 4.42%, 1.32%, and 0.16% by the $5^{th}$, $10^{th}$, and $15^{th}$ day, respectively.

Example 12

Impacts of Giant Salvinia Endocides on Other Selected Plant Species

General Experimental Procedures:

The experimental species included four herbaceous invasive aquatic species of angiosperms (flowering plants), namely, least duckweed (Lemna minuta) and Brazillan watermeal (Wolffia brasillensis Weddell) of the family Araceae, water hyacinth (Eichharnia crassipes) of the family Pontederiaceae and hydrilla (Hydrilla verticillate (L.f.) Royle) of the family Hydrocharitaceae, and two native tree species of gymnosperms, namely baldcypress (Taxodium

*distichum* (L.) Rich.) of the family Cupressaceae and loblolly pine (*Pinus taeda* L.) of the family Pinaceae. These species are often associated with giant *salvinia* in the southeastern United States. The experiments were conducted in the greenhouse (30° C. during the day time and 20° C. at night). Water extracts were prepared from the dried matter of giant *salvinia* (the preparation method see Example 2). Each species of least duckweed and Brazilian watermeal was separately cultured in nine plastic containers (14×15 cm, 0.68 L) with 400 mL tap water each. The spray experiment started until the plants fully covered each of the containers. For each of these two species, the plants were randomly classified into three groups: Control: each of the three containers was spayed three times with 10 mL of tap water each time; treatment I: each of the three containers was spayed twice with 10 mL of 0.1% water extract each time and then a week later with 10 mL of 5% of water extract; and treatment II: each of the three containers was spayed twice with 10 mL of 0.5% water extract each time and then a week later with 10 mL of 5% water extract. Surface coverage of living plants in each container of all treatments was photographed and measured weekly for six weeks. Five plants of each species of water hyacinth and *hydrilla* were cultured separately in container with 50 L tap water. For each species, three containers served as control and the plant leaves in each of the other three containers were sprayed twice with the total 100 mL of 5% water extract each time. Plant growth and survival status were documented and photographed weekly after the treatments for six weeks. Six 2-year old seedlings of each of bald cypress and loblolly pine in 2-gal pots were used in the experiment. For each species, three seedlings as controls received water only and the needles and stems in each of the other three plants were sprayed twice with the total 100 mL of 5% water extract each time. Plant growth and survival status were documented and photographed weekly after the treatments for six weeks.

Results:

During the six weeks of experiments, the growth of duckweed and watermeal had not been inhibited by 0.1%, 0.5% or 5% of water extract of giant *salvinia*. By the end of the observation, the living plants of these three species in all treatments and controls stayed in full surface coverage on all containers. Similarly, there was no obvious leaf color change or damage observed in any treatments of the other two invasive flowering plants and two native confer species.

Example 13

Inhibition of Giant *Salvinia* Plants by Ethanol Extract of the Dried Matter of Giant *Salvinia*

General Experimental Procedures:

Air-dried whole plants (550 g) were ground to a coarse powder and percolated two times with 95% EtOH at RT (each 3 L, 24 h). The combined EtOH solution was concentrated to give ethanol extract (34.0 g) under reduced pressure. 1.0 g giant *salvinia* ethanol extract was dissolved in 2 mL DMSO, and then diluted with 'water to yield 900 mL 0.1% and 1,000 mL 0.01% solutions (g/mL) for further experimental analysis. The experiment included 45 healthy and untreated living plants of giant *salvinia* (approximately 7 g in fresh weight each). The plants were cultured and tested in the plastic containers (14×15 cm, 0.68 L) in the NCPC Lab at RT. Controls: 15 plants with five in each container (3 replications) were cultured with 300 mL of tap water; 0.01% ethanol extract treatment: 15 plants with five in each container (3 replications) were sprayed with 300 mL 0.01% of the ethanol extracts of giant *salvinia* dissolved in tap water; and 0.1% ethanol extract treatment: 15 plants with five in each container (3 replications) were sprayed with 300 mL 0.1% of the ethanol extracts of giant *salvinia* dissolved in tap water. Plant growth and survival status were documented and photographed weekly after the treatments. By the end of 13th week, new growth biomass of plants in each treatment was measured. The biomass of new growth was a primary factor to measure the inhibition of each treatment on the target plant.

Results:

By the end of 13 weeks after the treatment, the plants in both Control and 0.01% ethanol extract treatment groups had new growth while about 60% of all giant *salvinia* plants treated with 0.1% ethanol extract of the dried matter of giant *salvinia* were dead and no significant growth on the other treated plants although they were still alive.

Example 14

Elimination and Prohibition of Giant *Salvinia* Plants by Water Extract of the Dried Matter of Least Duckweed (*Lemna minuta*)

General Experimental Procedures:

180 g (dry weight) of air-dried whole plants of least duckweed (*Lemna minuta*) (Lemnaceae) was ground to a coarse powder and percolated three times with 95% EtOH (v/v) at RT (each 2 L, 24 h). After ethanol extraction, the residual plant matters were dried and then percolated two times with water at RT (each 2 L, 24 h). Combined water solution was concentrated in vacuo to give water extract (12.2 g). 1.0 g Duckweed water extract was dissolved in $H_2O$ to yield 900 mL 0.1% and 1,000 mL 0.01% solutions (g/mL) for the giant *salvinia* inhibition experiment. The total 45 healthy and untreated living plants of giant *salvinia* (approximately 7 g in fresh weight each) were cultured and tested in plastic containers (14×15 cm, 0.68 L) in the NCPC Lab at RT. The three treatments were as follows. Controls: 15 plants with five in each container (3 replications) were cultured with 300 mL of tap water; 0.01% duckweed water extract treatment: 15 plants with five in each container (3 replications) were sprayed with 300 mL 0.01% of the duckweed extracts dissolved in tap water; and 0.1% duckweed water extract treatment: 15 plants with five in each container (3 replications) were sprayed with 300 mL 0.1% of the duckweed extracts dissolved in tap water. Plant growth and survival status were documented and photographed weekly after the treatments. By the end of 13th week, new growth biomass of plants in each treatment was measured. The biomass of new growth was a primary factor to measure the inhibition of each treatment on the target plant.

Results:

At the end of the 13th week of the experiment, each of the 15 giant *salvinia* plants in the control group had developed significant new growth (FIG. 28). By the same time, in the Treatment I group (0.01% water extract of least duckweed), six giant *salvinia* plants had developed significant new growth and four plants had somewhat new growth, while the rest five plants were dead and had no new growth. The total new plant growth of the Treatment I was about 40% of that of Control (FIG. 29). However, all 15 giant *salvinia* plants in the Treatment II group (0.1% water extract of least duckweed) were dead and had no any new growth at all (FIGS. 28 and 29). Further, during the eight months of observation, no recovery or new growth of giant *salvinia* were identified thereafter.

Example 15

Elimination and Prohibition of Giant *Salvinia* Plants by Ethanol Extract of the Dried Matter of Least Duckweed General Experimental Procedures:

Air-dried whole plants (180 g) were ground to a coarse powder and percolated three times with 95% EtOH (v/v) at RT (each 2 L, 24 h). The combined EtOH solution was concentrated under reduced pressure to give ethanol extract (6 g). 1.0 g duckweed ethanol extract was dissolved in 2 mL DMSO, and then diluted with water to yield 900 mL 0.1% and 1000 mL 0.01% solutions (g/mL) for the inhibition experiment. The total 45 healthy and untreated living plants of giant *salvinia* (approximately 7 g in fresh weight each) were cultured and tested in plastic containers (14×15 cm, 0.68 L) in the NCPC Lab at RT. The three treatments were as follows. Controls: 15 plants with five in each container (3 replications) were cultured with 300 mL of tap water; 0.01% duckweed ethanol extract treatment: 15 plants with five in each container (3 replications) were sprayed with 300 mL 0.01% of the duckweed extracts dissolved in tap water; and 0.1% duckweed ethanol extract treatment: 15 plants with five in each container (3 replications) were sprayed with 300 mL 0.1% of the duckweed extracts dissolved in tap water. Plant growth and survival status were documented and photographed weekly after the treatments. By the end of 13th week, new growth biomass of plants in each treatment was measured. The biomass of new growth was a primary factor to measure the inhibition of each treatment on the target plant.

Results:

Similar to those observed at the experiment 5, all 15 giant *salvinia* plants in the control group had significant new growth at the end of the 13th week of the experiment (FIG. 30). By then the total new plant growth of the Treatment I group (0.01% ethanol extract of least duckweed) is less than 15% of that of Control (FIG. 29). During the same time, 12 giant *salvinia* plants in the Treatment II group (0.1% ethanol extract of least duckweed) were dead and had no any new growth at all (FIGS. 29 and 30), and the rest three plants had dead mature tissues but developed somewhat new growth. However, the three new plants did not last long and eventually all 15 giant *salvinia* plants were dead by the end of 15 weeks after the treatment and no new growth thereafter during the eight months of observation.

Example 16

Elimination and Prohibition of Floating Fern (*Salvinia* Minima) Plants by Water Extract of the Dried Matter of Least Duckweed General Experimental Procedures:

The water extract of least duckweed used in this experiment was the same as used in Example 6. 1.0 g duckweed water extract was dissolved in $H_2O$ to yield 900 mL 0.1% and 1,000 mL 0.01% solutions (g/mL) for floating fern inhibition experiment. The total 90 healthy and untreated living plants of floating fern *salvinia* were cultured and tested in plastic containers (14×15 cm, 0.68 L) in the NCPC Lab at RT. The three treatments were as follows. Controls: 30 plants with 10 in each container (3 replications) were cultured with 300 mL of tap water; 0.01% duckweed water extract treatment: 30 plants with 10 in each container (3 replications) were sprayed with 300 mL 0.01% of the duckweed extracts dissolved in tap water; and 0.1% duckweed extract treatment: 30 plants with 10 in each container (3 replications) were sprayed with 300 mL 0.1% of the duckweed extracts dissolved in tap water. Plant growth and survival status were documented and photographed weekly after the treatments. By the end of 13th week, new growth biomass of plants in each treatment was measured. The biomass of new growth was a primary factor to measure the inhibition of each treatment on the target plant.

Results:

At the end of the 13th week of the experiment, each of the 30 floating fern plants in the control group had developed significant new growth (FIG. 31). The floating fern plants had no response with the treatment at 0.01% water extract of least duckweed during the first 13 weeks of experiment (FIGS. 31 and 32). By the same time, the plants treated with 0.1% water extract of least duckweed had only about 35% of growth as observed in the control (FIGS. 31 and 32). However, plants treated with 0.01% or 0.1% water extract of least duckweed were all dead by 20 weeks while untreated plants had new growth.

Example 17

Elimination and Prohibition of Floating Fern (*Salvinia minima*) Plants by Ethanol Extract of the Dried Matter of Least Duckweed General Experimental Procedures:

The ethanol extract of least duckweed used in this experiment was the same as used in the Experiment 7. 1.0 g duckweed ethanol extract was dissolved in 2 mL DMSO, and then diluted with water to yield 900 mL 0.1% and 1000 mL 0.01% solutions (g/mL) for the inhibition experiment. The total 90 healthy and untreated living plants of floating fern *salvinia* were cultured and tested in plastic containers (14×15 cm, 0.68 L) in the NCPC Lab at RT. The three treatments were as follows. Controls: 30 plants with 10 in each container (3 replications) were cultured with 300 mL of tap water; 0.01% duckweed ethanol 0.01% duckweed extract treatment extract treatment: 30 plants with 10 in each container (3 replications) were sprayed with 300 mL 0.01% of the duckweed extracts dissolved in tap water; and 0.1% duckweed ethanol extract treatment: 30 plants with 10 in each container (3 replications) were sprayed with 300 mL 0.1% of the duckweed extracts dissolved in tap water. Plant growth and survival status were documented and photographed weekly after the treatments. By the end of 13th week, new growth biomass of plants in each treatment was measured. The biomass of new growth was a primary factor to measure the inhibition of each treatment on the target plant.

Results:

At the end of the 13th week of the experiment, each of the 30 floating fern plants in the control group had developed significant new growth (FIG. 33). More than 80% of the floating fern plants were dead after the treatment at 0.01% ethanol extract of least duckweed and all plants treated with 0.1% level were dead within the 13 weeks (FIGS. 32 and 33). No new growth was observed thereafter during the eight months of observation.

Example 18

Elimination and Prohibition of Brazilian Pepper Tree (*Schinus terebinthifolius* Raddi) Seedlings by the Ethanol Extract of Brazilian Pepper Tree Fruits General Experimental Procedures:

The fruits of Brazilian pepper tree (*S. terebinthifolius*) (200 g, in dry weight) and Chinese tallow tree (*Triadica sebifera* (L.) Small) (Eurphorbiaceae) (260 g, in dry weight) were ground to coarse powders and extracted two times with 70% ethanol at RT (each 2 L, 48 h). After evaporated under reduced pressure, 25.4 g ethanol extract of Brazilian pepper tree and 27 g ethanol extract of Chinese tallow tree (both in dry weight) were obtained, respectively. Each extract was dissolved in water and then was prepared as experimental solutions at the concentration of 10%, respectively. The spray treatment experiment included 36 Brazilian pepper tree seedlings (three weeks old) in pots cultured in the greenhouse (30° C.). There were six treatments. Control: six seedlings were sprayed twice with a total 3 mL of tap water each time; surfactant treatment: six seedlings were sprayed twice with a total 3 mL of tap water with 7.5 uL Inlet™ and 3.75 uL Kinetin® each time; Brazilian pepper tree extracts treatment: six seedlings were sprayed twice with total a 3 mL of 10% pepper tree fruit extracts each time; Brazilian pepper extracts with surfactants treatment: six seedlings were sprayed twice with a total of 10% pepper tree fruit extracts with 7.5 uL Inlet™ and 3.75 uL Kinetin® each time; Chinese tallow tree extracts treatment: six seedlings were sprayed twice with total 3 mL of 10% tallow tree fruit extracts each time; and Chinese tallow tree extracts with surfactants treatment: six seedlings were sprayed twice with total a 3 mL of 10% tallow extracts with 7.5 uL Inlet™ and 3.75 uL Kinetin® each time. In addition, newly-spread leaves of six seedlings of each of the three native species in North America, namely poison ivy (*Toxicodendron radicans* (L.) Kuntze or *Rhus toxicodendron* L.) (family Anacardiaceae), sweetgum (*Liquidambar styraciflua* L.) (family Altingiaceae), and Shumard oak (*Quercus shumardii* Buckland) (family Fagaceae) were sprayed twice with a total 3 mL of 10% pepper tree fruit extracts each time, respectively. Plant growth and survival status were documented and photographed daily after the treatments.

Results:

All Brazilian pepper tree seedlings treated with Brazilian pepper tree extract or the extract with surfactants had significant damages three days after the first treatments (FIG. 34). Four weeks later, all six pepper tree seedlings were killed by the pepper tree extract with surfactants while five seedlings were killed and one was significantly damaged with dead apical bud and young leaves by the pepper tree extract (FIG. 34). In contrast, the Brazilian pepper tree plants had no damages in the control, surfactants, 10% ethanol extract of Chinese tallow tree fruits, or 10% ethanol extract of Chinese tallow tree fruits with surfactants treatment. None of the poison ivy, sweetgum, or Shumard oak seedlings had any damages by the Brazilian pepper tree extract.

Example 19

Elimination and Prohibition of Chinese Tallow Tree (*Triadica sebifera* (L.) Seedlings by the Ethanol Extract of Chinese Tallow Tree Fruits General Experimental Procedures:

The fruits of Chinese tallow tree (*Triadica sebifera* (L.) Small) (Eurphorbiaceae) (260 g, in dry weight) and Chinese privet (*Ligustrum sinense* Lour.) (family Oleaceae) (400 g, in dry weight) were ground to coarse powders and extracted two times with 70% ethanol at RT (each 2 L, 48 h), respectively. After evaporated under reduced pressure 27 g ethanol extract of Chinese tallow tree fruits and 25.3 g ethanol extract of Chinese privet fruits (both in dry weight) were obtained, respectively. Each extract was dissolved in water and then was prepared as experimental solutions at the concentration of 10%. The spray treatment experiment included 18 Chinese tallow tree seedlings (three weeks old) and 12 Chinese privet seedlings under the parent trees in the field. There were four treatments. Control: six seedlings of each species were sprayed with 3 mL of tap water; Chinese tallow tree extract treatment on Chinese tallow tree seedlings: six tallow tree seedlings were sprayed with 3 mL of 10% tallow tree fruit extract; Chinese tallow tree extract treatment on Chinese privet seedlings: six privet seedlings were sprayed with 3 mL of 10% tallow tree fruit extract; and Chinese privet extract treatment on Chinese tallow tree seedlings: six tallow tree seedlings were sprayed with 3 mL of 10% Chinese privet fruit extract. Plant growth and survival status were documented and photographed daily after the treatments.

Figure 35:
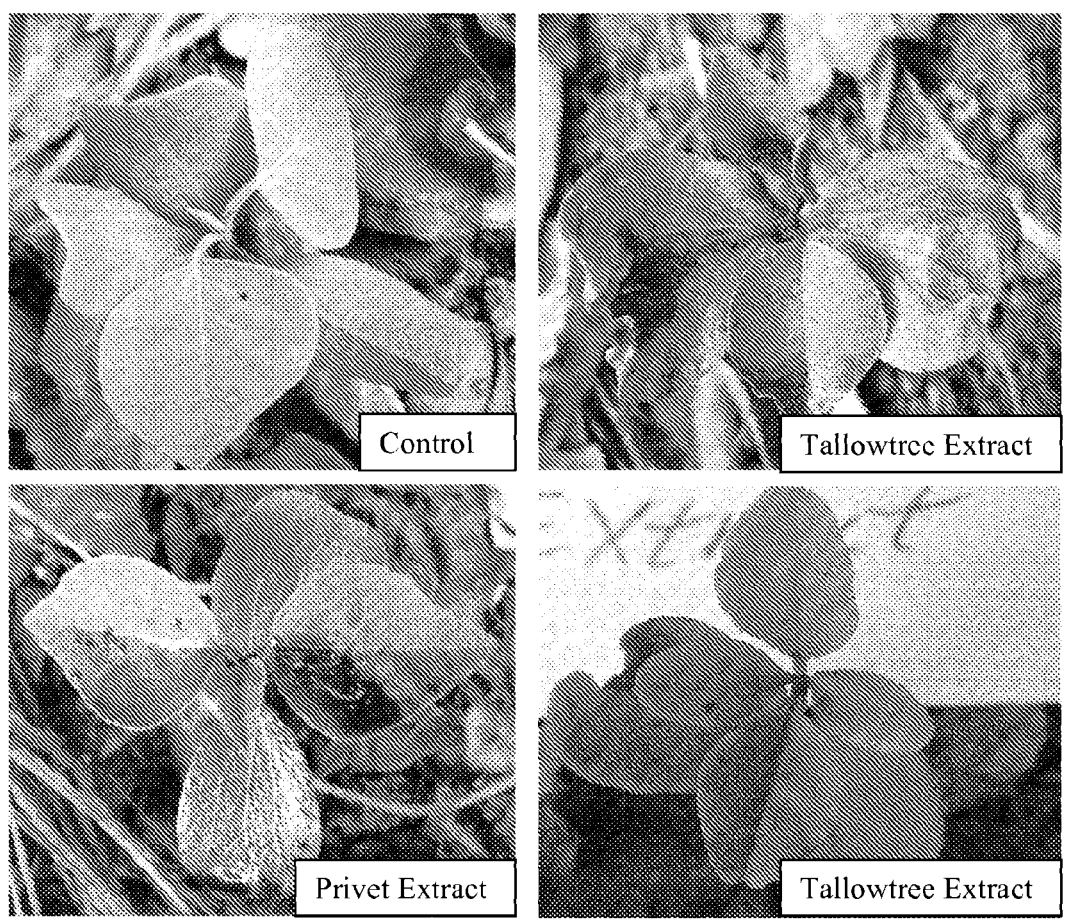
FIG. 35—The photographs show that 3-week-old seedlings of Chinese tallow tree (*Triadica sebifera* (L.) Small) and Chinese privet (*Ligustrum sinense* Lour.) (family Oleaceae) under treatment with 10% Chinese tallow tree fruit extract. All six Chinese tallow tree seedlings treated by the ethanol extract of Chinese tallow tree fruits were significantly damaged (right on the upper row) in comparison with control (left on the upper row). However, the tollowtree extract did not cause any damage in Chinese privet seedlings (right on the bottom row) while the Chinese privet extract did not damage the tallow tree seedlings (left on the bottom row).

Results:

All six Chinese tallow tree seedlings treated by the ethanol extract of Chinese tallow tree fruits were significantly damaged (FIG. 35). During the one week of experiments, two tallow tree seedlings were dead and four were severely injured. However, the tollowtree extract did not cause any damage in Chinese privet seedlings and the Chinese privet extract did not damage the tallow tree seedlings.

Example 20

Elimination and Prohibition of the Red Imported Fire Ant (*Solenopsis invicta* Buren) by the Fire Ant Extracts and Formic and Acetic Acids General Experimental Procedures:

Preparation of the fire ant extracts: (1) Acetone extract: 97 g (in fresh weight) of the red imported fire ant workers were extracted two times with acetone at RT (each 250 mL, 24 h). After evaporated under reduced pressure, the combined extractions yielded 2.13 g (in dry weight) acetone extract. (2) Ethanol extract: 110 g (in fresh weight) of the whole worker bodies of the red imported fire ant (*Solenopsis invicta* Buren) (family Furmicidae) were extracted two times with 95% EtOH at RT (each 250 mL, 24 h). After evaporated under reduced pressure, the combined extractions yielded 2.72 g (in dry weight) ethanol extract. Both extracts were dissolved in water and then prepared as experimental solutions at the concentration of 0.1%, 1%, 5%, and 10%, respectively. Preparation of the formic and acetic acids: Formic acid (88%, Sigma Aldrich©) and acetic acid (99.7, ACS reagent grade, VWR International LLC) were prepared as solutions at the concentration of 0.1%, 1%, and 5% immediately before the bioassay experiments. Detection of formic acid by NMR analysis: Approximately 100 fire ant workers were anesthetized by $CO_2$ and dissolved in 1 mL deuterated $CHCl_3$ (chroroform). The mixture was put under ultrasound for 30 min extraction. The fire ants were then removed and the extract was dried with anhydrous magnesium sulfate. 500 μL of the extract was transferred to NMR tube for detection. $^1$H-NMR experiments were performed on a JEOL ECS 400 spectrometer, with spectroscopic data referenced to the solvent used. According to standard formic acid ¹H-NMR spectrum, the unique singlet of the aldehyde proton should appear at $\delta_H$ 8.02. Contact Toxicity Assays: (1) The impacts of acetone and ethanol extracts of the red imported fire ants on the fire ants: the experiment includes nine treatments and each treatment had the total 150 workers of the red imported fire ant with 50 ants in each of the three 100 mL beakers (as three replications). The ants in each beaker were topically sprayed with a total 1 mL of 0.1%, 1%, 5%, or 10% solutions of either acetone or ethanol extract, respectively. The control group was sprayed with 1 mL pure water. The beakers in all treatments were covered by cloth to prevent the escape of the fire ants. The surviving number of the fire ants in each treatment was counted by 1 h interval for 7 h. (2) The impacts of formic and acetic acids on the fire ants: the experiment had seven treatments and each treatment had the total 150 workers of the red imported fire ant with 50 ants in each of the three 100 mL beakers (as three replications). The ants in each beaker were topically sprayed with a total 1 mL of 0.1%, 1%, or 5% solutions of either formic or acetic acids, respectively. The control group was sprayed with 1 mL pure water. The beakers in all treatments were covered by cloth to prevent the escape of fire ants. The surviving number of the fire ants in each treatment was counted by 1 h interval for 7 h. For extracts and acids, $LD_{50}$ (the dose required to kill half of the exposed fire ants) and $LD_{90}$ (the dose required to kill 90% of the exposed fire ants) were calculated by the PROBIT procedure of SPSS 13.0 for Windows. (3) The impacts of combined application of ethanol extract and formic acid on the fire ants: The experiment had the total 720 workers of the red imported fire ants with 30 ants in each of the 24 Petri Dishes (85 mm in diameter). Control: the ants in three dishes had no treatment; Water treatment: the ants in each of the three dishes were in contact with 1 mL water for 10 sec; 2.5% ethanol extract treatment: the ants in each of the three dishes were in contacted with 1 mL of 2.5% ethanol extract for 10 sec; 2.5% formic acid treatment: the ants in each of the three dishes were in contacted with 1 mL of 2.5% formic acid for 10 sec; mixture of ethanol extract (2.5%) and formic acid (2.5%) treatment: the ants in each of the three dishes were in contacted with 1 mL of a mixture of ethanol extract and formic acid (each had 2.5% in concentration in the mixture) for 10 sec; 5% ethanol extract treatment: the ants in each of the three dishes were in contacted with 1 mL of 5% ethanol extract for 10 sec; 5% formic acid treatment: the ants in each of the three dishes were in contacted with 1 mL of 5% formic acid for 10 sec; and mixture of ethanol extract (5%) and formic acid (5%) treatment: the ants in each of the three dishes were in contacted with 1 mL of a mixture of ethanol extract and formic acid (each had 5% in concentration in the mixture) for 10 sec. The surviving number of the fire ants in each treatment was counted by 15 min interval for 90 min. (4) The impacts of combined application of ethanol extract and formic acid on the injured fire ants: The 450 workers of the red imported fire ants were placed in 15 Petri Dishes (85 mm in diameter) with 30 in each dish. The ants were anesthetized by $CO_2$ and then each ant was injured in its gaster by pin. Control: the ants in three dishes had no treatment; Water treatment: the ants in each of the three dishes were in contact with 1 mL water for 10 sec; 1.25% ethanol extract treatment: the ants in each of the dishes were in contacted with 1 mL of 1.25% ethanol extract for 10 sec; 1.25% formic acid treatment: the ants in each of the dishes were in contact with 1 mL of 1.25% formic acid for 10 sec; and mixture of ethanol extract (1.25%) and formic acid (1.25%) treatment: the ants in each of the three dishes were in contacted with 1 mL of a mixture of ethanol extract and formic acid (each had 1.25% in concentration in the mixture) for 10 sec. The surviving number of the fire ants in each treatment was counted by 15 min interval for 90 min. (5) The impacts of ethanol extract of the red imported fire ants on subterranean termite (*Reticulitermes flavipes* (Kollar)) (family Rhinotermitidae): the experiment included five treatments and each treatment had 150 subterranean termites with 20 workers, 10 soldiers and 5 winged reproductive ants in each of the three 100 mL beakers (as three replications). The termites in each beaker were topically sprayed with a total 1 mL of 0.1%, 1%, 5%, or 10% solutions of ethanol extract, respectively. The control group was sprayed with 1 mL pure water. The beakers in all treatments were covered by cloth to prevent the escape of fire ants. The surviving number of the fire ants in each treatment was counted by 1 h interval for 7 h. Fumigation Toxicity Assays of Formic Acid: The experiment included approximately 300 workers of the fire ants in each container with the filter paper treated with 10 mL of 0.1%, 1%, or 5% formic acid, respectively. The surviving number of the fire ants in each treatment was counted by 1 h interval for 2 h. $LD_{50}$ (the dose required to kill half of the exposed fire ants) and $LD_{90}$ (the dose required to kill 90% of the exposed fire ants) were calculated by the PROBIT procedure of SPSS 13.0 for Windows.

Figure 37:
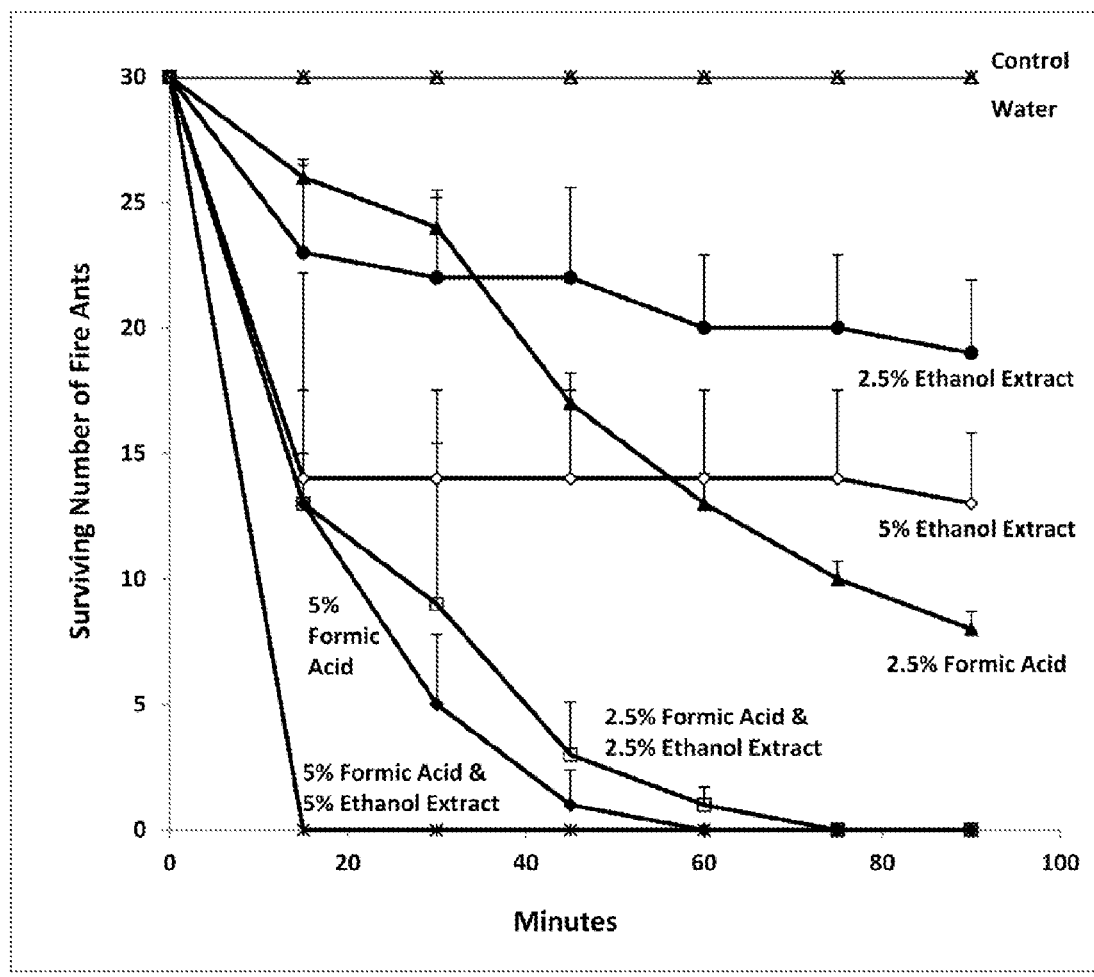
FIG. 37—The diagram shows the impacts of ethanol extract of the red imported fire ants and formic acid on the workers of the red imported fire ant (*Solenopsis invicta* Buren). During the 90 min of contact toxicity bioassays, the combined applications of ethanol extract and formic acid had more significant effects than the use of either ethanol extract or formic acid alone (with bars presenting standard deviations).
Figure 38:
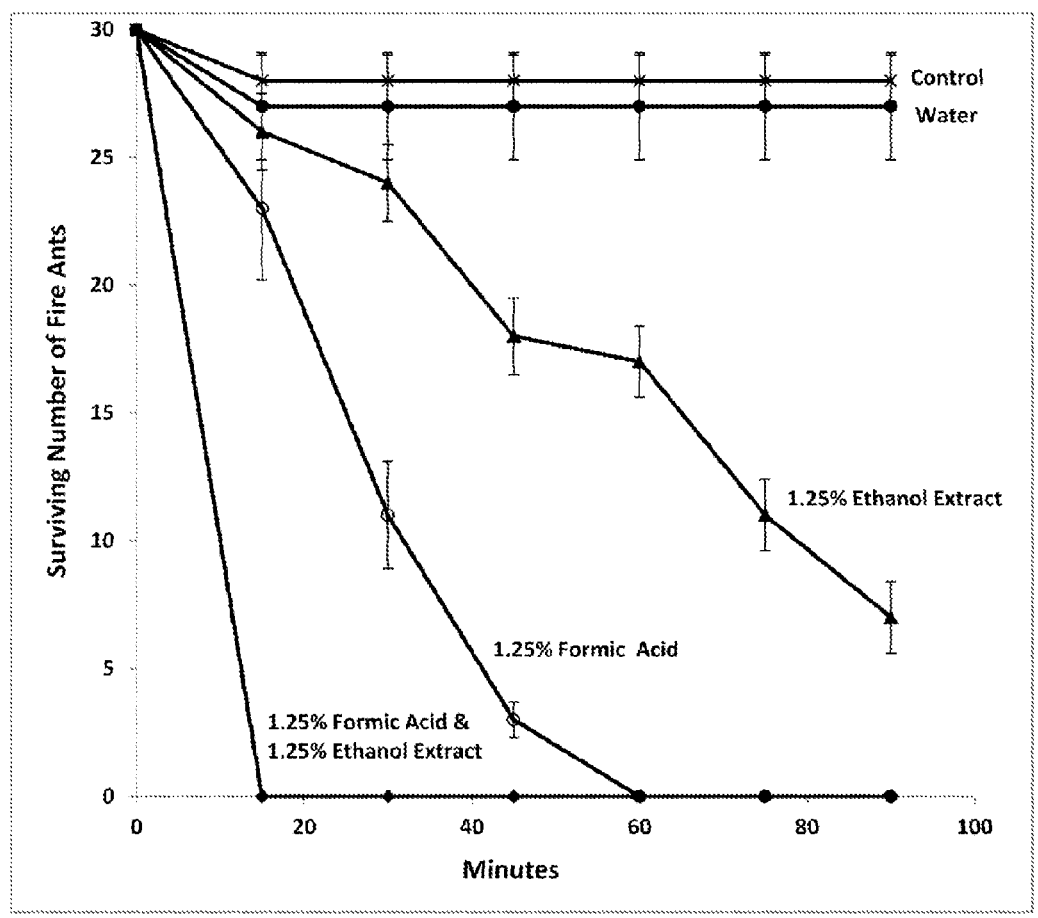
FIG. 38—The diagram shows the impacts of ethanol extract of the red imported fire ant (*Solenopsis invicta* Buren) and formic acid on the injured workers of the red imported fire ants. During the 90 min of contact toxicity bioassays, the combined applications of ethanol extract and formic acid had more significant effects than the use of either ethanol extract or formic acid alone (with bars presenting standard deviations).

Results:

The topical applications of both the extracts of the red imported fire ants and the organic acids inhibited the fire ants. Both formic acid and acetic acid were not detected in chloroform, acetone, or ethanol extract according to the NMR analysis. The ethanol extract showed more significant toxicity against the fire ants than the acetone extract. During the 7 h contact toxicity bioassays, an average of approximately 60%, 70%, or 80% of the fire ants in contact with 1%, 5%, or 10% ethanol extract were dead, respectively (FIG. 36). In contact toxicity bioassays, 7 h $LD_{50}$ and $LD_{90}$ of formic acid, acetic acid, ethanol extract, and acetone extract for the fire ants was 1.9% and 5.09%, 6.42% and 9.96%, 1.81% and 15.58%, and 18.67% and 34.18%, respectively. Formic acid had a more significant impact on survival of fire ants than acetic acid. During the 90 min of contact toxicity bioassay, the average mortality with 2.5% and 5% formic acid was more than 70% or 100%, respectively (FIG. 37). In fumigation bioassays, 2 h $LD_{50}$ and $LD_{90}$ of formic acid for the fire ants was 0.5% and 0.9%, respectively. The combined application of ethanol extract of the fire ants and formic acid had more significant effects on fire ant survival than use of either ethanol extract or formic acid alone (FIGS. 37 and 38). However, the ethanol extract of the fire ants had no impacts on subterranean termite.

Example 21

Elimination and Prohibition of the Subterranean Termite (*Reticulitermes flavipes* (Kollar)) by Formic Acid General Experimental Procedures:

Formic acid (90.4%, certified ACS reagent grade, Fisher Scientific Company, Fair Lawn, N.J., USA) was prepared as solutions at the concentration of 0.1%, 1%, and 5% immediately before the bioassay experiments. Detection of formic acid by NMR analysis: Approximately 100 termites were anesthetized by $CO_2$ and dissolved in 1 mL deuterated $CHCl_3$ (chroroform). The mixture was put under ultrasound for 30 min extraction. The termites were then removed and the extract was dried with anhydrous magnesium sulfate. 500 μL of the extract was transferred to NMR tube for detection. ¹H-NMR experiments were performed on a JEOL ECS 400 spectrometer, with spectroscopic data referenced to the solvent used. According to standard formic acid ¹H-NMR spectrum, the unique singlet of the aldehyde proton should appear at $\delta_H$ 8.02. Contact Toxicity Assays: The experiment included five treatments and each treatment had total 105 subterranean termite (*Reticulitermes flavipes* (Kollar)) (family Rhinotermitidae) including 20 workers, 10 soldiers and 5 winged reproductives (alates) in each of the three 100 mL beakers (as three replications). The termites in each beaker were topically sprayed with a total 1 mL of 0.1%, 1%, 5%, or 10% solutions of formic acid, respectively. The control group was sprayed with 1 mL pure water. The beakers in all treatments were covered by cloth to prevent the escape of termites. The surviving number of the termites in each treatment was counted by 1 h interval for 7 h.

Figure 39:
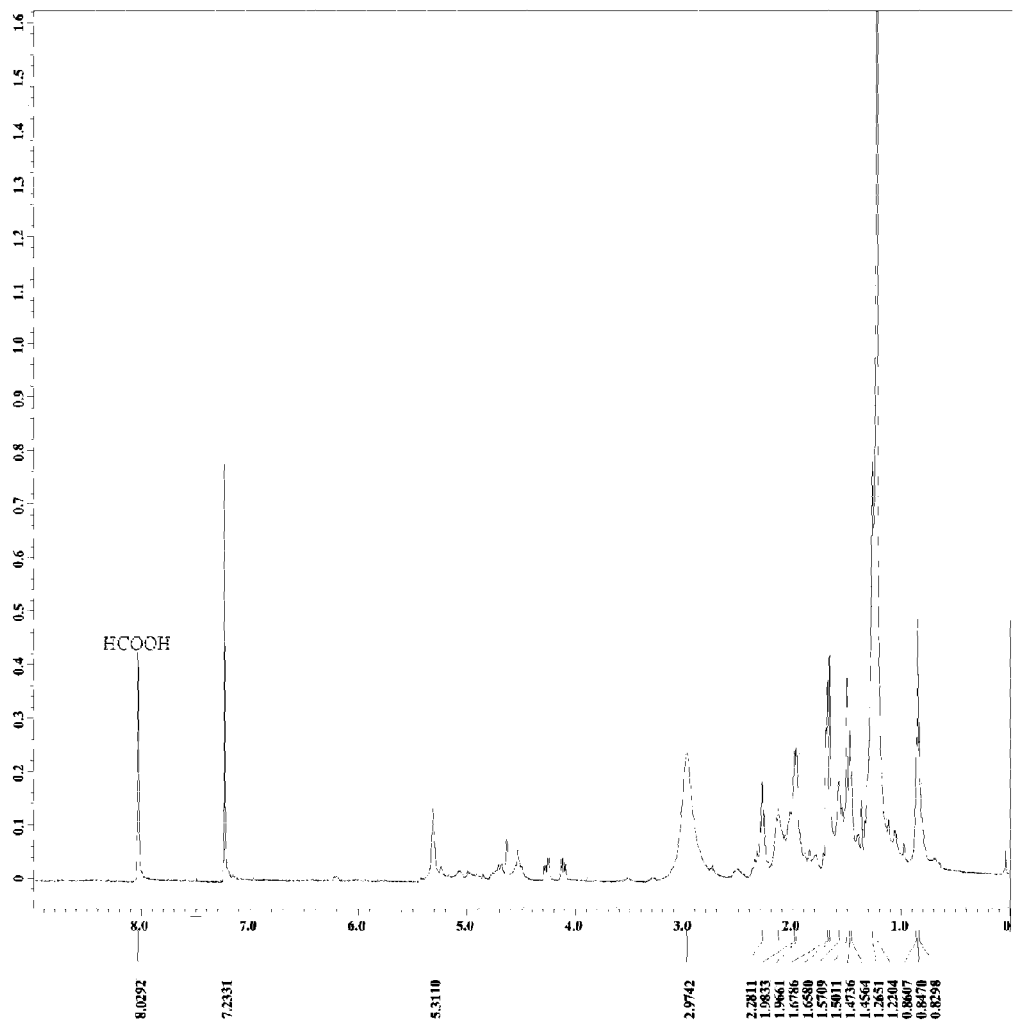
FIG. 39—The diagram shows the occurrence of formic acid (HCOOH) in chroroform ($CHCl_3$) extract of the subterranean termite (*Reticulitermes flavipes* (Kollar)) by NMR analysis. $^1$H-NMR experiments were performed on a JEOL ECS 400 spectrometer, with spectroscopic data referenced to the solvent used. According to standard formic acid $^1$H-NMR spectrum, the unique singlet of the aldehyde proton should appear at $\delta_H$ 8.02.
Figure 40:
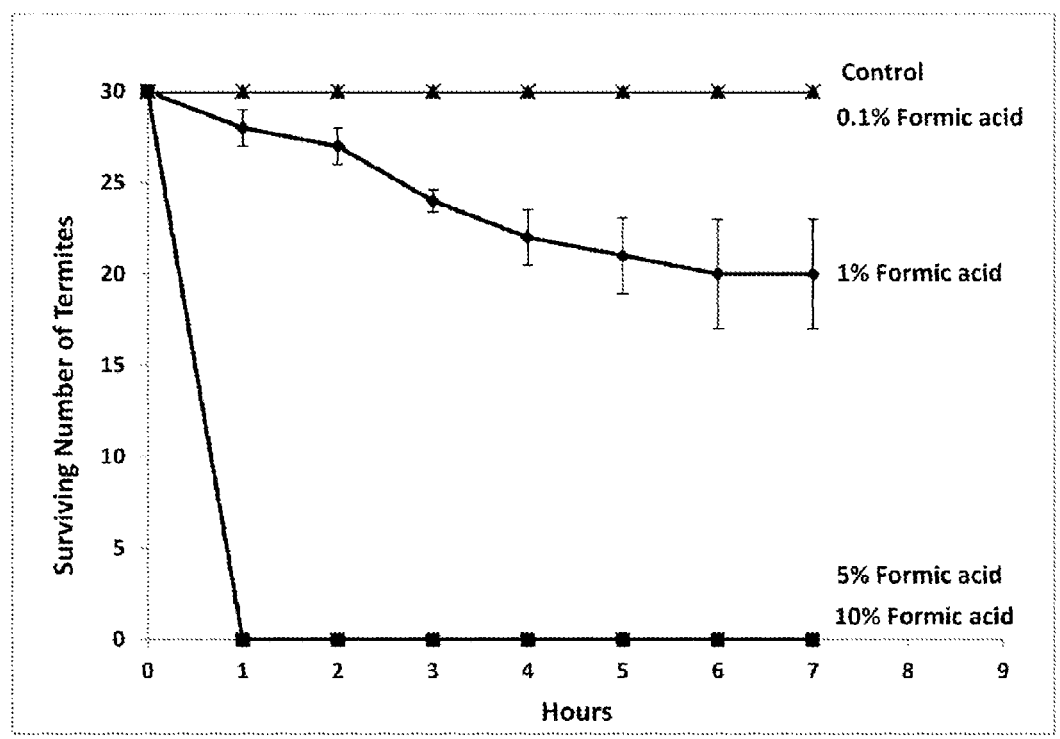
FIG. 40—The diagram shows the impacts of formic acid on the subterranean termite (*Reticulitermes flavipes* (Kollar)). Formic acid at higher concentrations (5 or 10%) killed all termites (including workers, soldiers, and reproductive) during the first hour of contact experiment. More than 40% of the termites were killed by the 1% formic acid during the 7 h of contact toxicity bioassays. However, formic acid at 0.1% concentration had no impact on the termites (with bars presenting standard deviations).

Results:

The NMR analysis indicated that the subterranean termites contained significant amount of formic acid (FIG. 39). Formic acid at higher concentrations (5 or 10%) killed all termites (including workers, soldiers, and reproductive) during the first hour of contact experiment. During the 7 h of contact toxicity bioassays, formic acid at 1% concentration killed more than 40% of the termites (FIG. 40). However, formic acid at 0.1% concentration had no impact on the termites. In the contact toxicity bioassays, 7 h $LD_{50}$ and $LD_{90}$ of formic acid for the termite was 4.71% and 9.08%, respectively.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbasi & Nipaney, *Environ. Conserv.* 13: 235-241, 1986.
Abdul-Rahman and Habib, *J. Chem. Ecol.* 15: 2289-2300, 1989.
Ascune, et al., *Science* 331: 1066-1068, 2011.
Baldwin & Callahan, *Oecologia* 94: 534-541, 1993.
Barrett, *Sci. Amer.* 260: 90-97, 1989.
Barthlott, et al., *Botany.* 87: 830-836, 2009.
Batish, et al., *Environ. Exp. Bot.* 47: 149-155, 2002.
Beck, et al., *Invasive Pl. Sci. Manag.* 1: 414-421, 2008.
Chen, et al., *J. Agric. Food Chem.* 57: 3128-3133, 2009.
Chon, et al., *Crop Protect.* 21(10): 1077-1082, 2002.
Chou & Kuo, *J. Chem. Ecol.* 12(6): 1431-1448, 1986.
Chou & Lin, *J. Chem. Ecol.* 2: 353-367, 1976.
Choudhary, et al., *Phytochemistry* 69: 1018-1023, 2008.
Ding, et al., *Chem. Pharm. Bull.* 47: 652-655, 1999.
Finlayson, *Aquat. Bot.* 18: 257-262, 1984.
Fowden & Lea, In: Herbivores: their interaction with secondary plant metabolites. Academic Press, New York, pp 135-160, 1979.
Gog, et al., *Chemoecology* 15: 115-119, 2005.
Hedge and Miller, *Crop Sci.* 30(6): 1255-1259, 1990.
Heisey, In: Biological active natural products: agrochemicals. CRC Press, Florida, pp. 57-68, 1999.
Hoffman, *Curr. Opin. Allergy Clin. Immunol.* 10: 342-346, 2010.
Javaid, et al., *Pak. J. Bot.* 39(7): 2611-2618, 2007.
Jubinsky & Anderson, *Catanea* 61(3): 226-231, 1996.
Julien, et al., In Biological control of tropical weeds using arthropods. Cambridge University Press, 2009.
Kato-Noguchi & Ota, *J. Rice Res.* 1: 108, 2013
Li, A system for increasing the production of indole and quinoline alkaloids, particularly camptothecins and related compounds, from plants, 2002.
Li, et al., *Front. Biosci.* E2: 1196-1210, 2010.
Maurya, et al., *Phytochemistry* 65: 915-920, 2004.
McKey, *Am. Nat.* 108: 305-320, 1974.
Morgan, *Myrmecol. News* 11: 79-90, 2008.
Morrison, et al., *Biol. Invasions* 6: 193-191, 2004.
Narasimhulua, et al., *Nat. Prod. Res.* 24: 1390-1394, 2010.
Paudel, *J. Plant Sci.* 6: 85-92, 2009.
Picman & Picman, *Biochem. Syst. Ecol.* 12(3): 287-292, 1984.
Pimentel, et al. Environmental and economic costs associated with nonindigenous species in the United States, 1999.
Quintana, et al., *Phytochemistry* 69: 2572-2578, 2008.
Room, et al., *Trends Ecol. Evol.* 5: 74-79, 1990.
Room & Thomas, *J. Appl. Ecol.* 23: 1013-1028, 1986.
Schooler, et al., *Nature* 470: 86-89, 2011.
Singh, et al., *Crit. Rev. Plant Sci.* 18: 757-772, 1999.
Sirikantaramas, et al., *Phytochem. Rev.* 7: 467-477, 2008a.
Sirikantaramas, et al., *PNAS.* 105: 6782-6786, 2008b.
USDA Animal and Plant Health Inspection Service. Giant *Salvinia*—Pest Alert, 2000.
Wang, *Ann. Rev. Biochem.* 65: 635-692, 1996.
Wu, et al., *J. Nat. Prod.* 74: 989-996, 2011.
Wyman-Simpson, et al., *Plant Soil* 135: 83-94, 1991.
Xuan, et al. *Agron. Sustain. Dev.* 26: 89-97, 2006.

The invention claimed is:

1. A method of controlling an invasive plant species, the method comprising applying a composition to a plant of the invasive species, the composition comprising 0.01 to about 0.5% by weight of a natural pesticide, wherein the natural pesticide is a compound of formula:

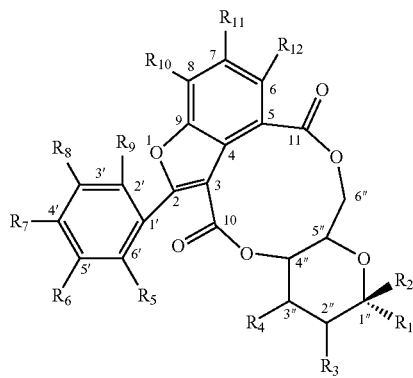

wherein:
each of $R_1$, $R_2$, $R_3$, $R_4$ is independently —H, —OH, -halogen, —NH$_2$, —COOH, —C(O)NH$_2$, —SH, —S(O)NH$_2$, —S(O)$_2$NH$_2$, —OCH$_2$OR$_{13}$, —OC(O)R$_{13}$, —OC(O)OR$_{13}$, —OC(O)NR$_{13}$, —OP(O)(OR$_{13}$)$_2$, —SR$_{13}$, —S(O)$_2$NHR$_{13}$, —OP(O)(OR$_{13}$)$_2$, —SOR$_{13}$, —S(O)$_2$R$_{13}$, —NHC(O)R$_{13}$, —NHSOR$_{13}$, NHS(O)$_2$R$_{13}$, —OPO(OR$_{14}$)$_2$—O-arylPO(OR$_{14}$)$_2$, or —O-alkylarylPO(OR$_{14}$)$_2$, —NHR$_{13}$, —N(R$_{13}$)$_2$, —C(S) R$_{13}$, —OR$_{13}$, each of $R_5$, $R_6$, $R_7$, $R_8$, $R_9$, $R_{10}$, $R_{11}$, $R_{12}$ is independently —H, —OH, -halogen, —CN, —NH$_2$, —NO$_2$, —COOH, —C(O)NH$_2$, —SH, —S(O)NH$_2$, —S(O)$_2$NH$_2$, —C$_1$-C$_{10}$ (oxy)alkyl, —C$_1$-C$_{10}$ alky, —C$_1$-C$_{10}$ alkoxy, —C$_1$-C$_{10}$ (hydroxyl)alkyl, —C$_1$-C$_{10}$ (amino)alkyl, —C$_1$-C$_{10}$ (halo)alkyl, —C$_2$-C$_{10}$ alkenyl, —C$_2$-C$_{10}$ (aryl)alkyl, —CH$_2$OR$_{13}$, —OCH$_2$OR$_{13}$, —OC(O)R$_{13}$, —C(O)R$_{13}$, —OC(O)OR$_{13}$, —OC(O)NR$_{13}$, —C(O)O R$_{13}$, —C(O)NR$_{13}$, —OP(O)(OR$_{13}$)$_2$, —SR$_{13}$, —S(O)$_2$NHR$_{13}$, —C(O)NR$_{13}$, —OP(O)(OR$_{13}$)$_2$, —SR$_{13}$, —S(O$_2$)NHR$_{13}$, —SOR$_{13}$, —S(O)$_2$R$_{13}$, —NHC(O)R$_{13}$, —NHSOR$_{13}$, NHS(O)$_2$R$_{13}$, —OPO(OR$_{14}$)$_2$, —O-arylPO(OR$_4$)$_2$, or —O-alkylarylPO(OR$_{14}$)$_2$, -isocyanate, -azido, and $R_{14}$ is —H, —C$_1$-C$_{10}$ alkyl, C$_7$-C$_{13}$ arylalkyl, C$_1$-C$_{10}$aminoalkyl, haloalkyl, C$_1$-C$_{10}$ hydroxyalkyl, C$_1$-C$_{10}$ alkoxy, isocyanate, azido, imino, thio, and $R_{13}$ is —H, —C$_1$-C$_{10}$ alkyl, —(C$_3$-C$_7$) cycloalkyl, —C$_1$-C$_{10}$ (halo)alkyl, -aryl, —C$_2$-C$_{10}$ alkenyl, —C$_2$-C$_{10}$, —C$_2$-C$_{10}$ alkynyl, —C$_1$-C$_{10}$ (aryl)alkyl, —C$_2$-C$_{10}$ (aryl)alkenyl, —C$_2$-C$_{10}$ (aryl)alkynyl, —C$_1$-C$_{10}$ (hydroxyl)alkyl, —C$_1$-C$_{10}$ alkoxy, —C$_1$-C$_{10}$ (amino) alkyl, -isocyanate, -azido, -imino, -thio, -alkenyloxy, -alkynyloxy, -aryloxy, -aralkoxy, -heteroaryloxy, -acyloxy, -alkoxyamino, -alkenylamino, -alkynylamino, -arylamino, -aralkylamino, -heteroarylamino, -alkylsulfonylamino, -heterocycloalkyl, -heteroaryl.

2. The method of claim 1, wherein the natural pesticide is a compound of formula:

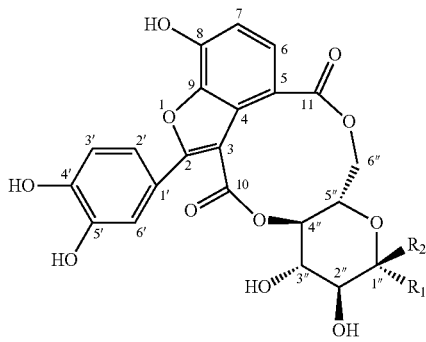

wherein
$R_1$ is OH or α-H; and
$R_2$ is β-H or OH.

3. The method of claim 2, wherein $R_1$=OH, $R_2$=β-H.

4. The method of claim 2, wherein $R_1$=α-H, $R_2$=OH.

5. The method of claim 2, wherein $R_1$=OH, $R_2$=OH.

6. The method of claim 2, wherein $R_1$=α-H, $R_2$=β-H.

7. The method of claim 1, wherein the invasive species is a terrestrial plant.

8. The method of claim 1, wherein the invasive species is an aquatic plant.

9. The method of claim 1, wherein the invasive species is *Salvinia adnata, S. auriculata, S. biloba, S. cucullata, S. cyathiformis, S. hastata, S. herzogii, S. martynii, S. minima, S. molesta, S. natans, S. nymphellula, S. oblongifolia, S. radula, S. rotundifolia, S. sprucei, Azolla caroliniana, A. circinata, A. cristata, A. filiculoides, A. japonica, A mexicana, A. microphylla, A. nilotica, A. pinnata, A. rubra, Lemna minuta, Eichharnia crassipes*, and/or *Pistia stratiotes*.

10. The method of claim 1, wherein the invasive species is *Salvinia molesta, Salvinia minima, Azolla caroliniana, Lemna minuta, Eichharnia crassipes*, and/or *Pistia stratiotes*.

11. The method of claim 1, wherein growth of the plant of the invasive species is halted within 1 week and/or 1 month.

12. The method of claim 1, wherein the growth of the plant of the invasive species is halted for at least 1 year.

13. The method of claim 1, wherein the composition comprising the natural pesticide is applied topically to the plant of the invasive species; sprayed onto the plant of the invasive species, spread around the plant of the invasive species; and/or dissolved in water surrounding the plant of the invasive species.

14. The method of claim 13, wherein the composition is applied to the trichomes of the plant of the invasive species.

15. The method of claim 13, wherein the composition is sprayed onto the plant of the invasive species.

16. The method of claim 13, wherein the composition is spread around the plant of the invasive species.

17. The method of claim 13, wherein the composition is dissolved in water surrounding the plant of the invasive species.

18. The method of claim 1, wherein the composition further comprises a surfactant.

19. The method of claim 18, wherein the composition contains about 0.1% by weight of the natural pesticide.

20. The method of claim 1, further comprising applying a secondary agent.

* * * * *